United States Patent
Kekec et al.

(10) Patent No.: US 11,530,250 B2
(45) Date of Patent: Dec. 20, 2022

(54) TYROSINE-SPECIFIC FUNCTIONALIZED INSULIN AND INSULIN ANALOGS

(71) Applicants: Merck Sharp & Dohme Corp., Rahway, NJ (US); Ahmet Kekec, Hoboken, NJ (US); Nancy Jo Kevin, East Brunswick, NJ (US); Bing Li, Towaco, NJ (US); Songnian Lin, Holmdel, NJ (US); Craig A. Parish, Tenafly, NJ (US); Weijuan Tang, Scotch Plains, NJ (US)

(72) Inventors: Ahmet Kekec, Hoboken, NJ (US); Nancy Jo Kevin, East Brunswick, NJ (US); Bing Li, Towaco, NJ (US); Songnian Lin, Holmdel, NJ (US); Craig A. Parish, Tenafly, NJ (US); Weijuan Tang, Scotch Plains, NJ (US)

(73) Assignee: MERCK SHARP & DOHME LLC, Rahway, NJ (US)

( * ) Notice: Subject to any disclaimer, the term of this patent is extended or adjusted under 35 U.S.C. 154(b) by 0 days.

(21) Appl. No.: 16/980,579

(22) PCT Filed: Mar. 18, 2019

(86) PCT No.: PCT/US2019/022684
§ 371 (c)(1),
(2) Date: Sep. 14, 2020

(87) PCT Pub. No.: WO2019/182942
PCT Pub. Date: Sep. 26, 2019

(65) Prior Publication Data
US 2021/0002345 A1    Jan. 7, 2021

Related U.S. Application Data

(60) Provisional application No. 62/646,424, filed on Mar. 22, 2018.

(51) Int. Cl.
*C07K 14/62* (2006.01)
*C07K 1/107* (2006.01)

(52) U.S. Cl.
CPC ............ *C07K 14/62* (2013.01); *C07K 1/1077* (2013.01)

(58) Field of Classification Search
None
See application file for complete search history.

(56) References Cited

U.S. PATENT DOCUMENTS

| 8,765,920 B2 * | 7/2014 | Barbas, III | ........... C07D 249/12 |
| | | | 548/263.6 |
| 9,149,541 B2 | 10/2015 | Adamo et al. | |
| 2012/0289682 A1 | 11/2012 | Barbas, III et al. | |

FOREIGN PATENT DOCUMENTS

| WO | 2015051052 A2 | 4/2015 | |
| WO | 2016066749 A1 | 5/2016 | |
| WO | 2017205309 A1 | 11/2017 | |
| WO | WO-2017205309 A1 * | 11/2017 | ............. A61K 38/28 |

OTHER PUBLICATIONS

Alvarez-Dorta, Dimitri et al., Electrochemically Promoted Tyrosine-Click-Chemistry for Protein Labeling, J. Am. Chem. Soc., 2018, 17120-17126, 140.
Supplementary European Search Report in corresponding EP 19 772613.6 dated Jan. 4, 2022.
Ban, Hitoshi et al., Facile and Stabile Linkages through Tyrosine: Bioconjugation Strategies with the Tyrosine-Click Reaction, Bioconjugate Chem., 2013, 520-532, 24.
Ban, Hitoshi, Tyrosine Bioconjugation through Aqueous Ene-Type Reactions: A Click-Like Reaction for Tyrosine, Journal of the American Chemical Society, 2010, 1523-1525, vol. 132, No. 5.
Hu, Qi-Ying et al., Synthesis of a well-defined glycoconjugate vaccine by a tyrosine-selective conjugation strategy, Chem. Sci., 2013, 3827-3832, 4.
Jessica, Flagothier et al., Synthesis of [18F]4-(4-fluorophenyl)-1,2,4-triazole-3,5-dione: an agent for specific radiolabelling of tyrosine, RSC Adv., 2013, 24936-24940, 3.
Montanari, Elita, Tyrosinase-Mediated Bioconjugation. A Versatile Approach to Chimeric Macromolecules, Bioconjugate Chemistry, 2018, 2550-2560, vol. 29, No. 8.

* cited by examiner

*Primary Examiner* — Christina Bradley

(57) ABSTRACT

The present invention relates to tyrosine-specific functionalized insulin analogs and processes of making such tyrosine-specific functionalized insulin analogs using R-3H-1,2,4-triazoline-3,5-(4H)diones (PTAD).

1 Claim, No Drawings

Specification includes a Sequence Listing.

SEQUENCE LISTING

<160> NUMBER OF SEQ ID NOS: 45

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Insulin aspart B chain

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Insulin lispro B Chain

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Insulin glargine A chain

```
<400> SEQUENCE: 5

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Insulin glargine B chain

<400> SEQUENCE: 6

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Insulin A chain muteins
<220> FEATURE:
<221> NAME/KEY: MOD_RES
<222> LOCATION: (8)..(8)
<223> OTHER INFORMATION: threonine or histidine
<220> FEATURE:
<221> NAME/KEY: MOD_RES
<222> LOCATION: (17)..(17)
<223> OTHER INFORMATION: glutamic acid or glutamine
<220> FEATURE:
<221> NAME/KEY: MOD_RES
<222> LOCATION: (19)..(19)
<223> OTHER INFORMATION: tyrosine, 4-methoxy-phenylalanine, or 4-amino
      phenylalanine
<220> FEATURE:
<221> NAME/KEY: MOD_RES
<222> LOCATION: (21)..(21)
<223> OTHER INFORMATION: asparagine or glycine

<400> SEQUENCE: 7

Gly Ile Val Glu Gln Cys Cys Xaa Ser Ile Cys Ser Leu Tyr Gln Leu
1               5                   10                  15

Xaa Asn Xaa Cys Xaa
            20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: histidine or threonine
<220> FEATURE:
<221> NAME/KEY: MOD_RES
<222> LOCATION: (5)..(5)
<223> OTHER INFORMATION: alanine, glycine or serine
```

```
<220> FEATURE:
<221> NAME/KEY: MOD_RES
<222> LOCATION: (6)..(6)
<223> OTHER INFORMATION: histidine, aspartic acid, glutamic acid,
      homocysteic acid, or cysteic acid
<220> FEATURE:
<221> NAME/KEY: MOD_RES
<222> LOCATION: (24)..(24)
<223> OTHER INFORMATION: proline or lysine
<220> FEATURE:
<221> NAME/KEY: MOD_RES
<222> LOCATION: (25)..(25)
<223> OTHER INFORMATION: proline or lysine

<400> SEQUENCE: 8

Xaa Leu Cys Gly Xaa Xaa Leu Val Glu Ala Leu Tyr Leu Val Cys Gly
1               5                   10                  15

Glu Arg Gly Phe Phe Tyr Thr Xaa Xaa
            20                  25

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: phenylalanine and desamino-phenylalanine
<220> FEATURE:
<221> NAME/KEY: MOD_RES
<222> LOCATION: (5)..(5)
<223> OTHER INFORMATION: histidine or threonine
<220> FEATURE:
<221> NAME/KEY: MOD_RES
<222> LOCATION: (9)..(9)
<223> OTHER INFORMATION: alanine, glycine, or serine
<220> FEATURE:
<221> NAME/KEY: MOD_RES
<222> LOCATION: (10)..(10)
<223> OTHER INFORMATION: histidine, aspartic acid, glutamic acid,
      homocysteic acid, or cysteic acid
<220> FEATURE:
<221> NAME/KEY: MOD_RES
<222> LOCATION: (28)..(28)
<223> OTHER INFORMATION: aspartic acid, proline, or lysine
<220> FEATURE:
<221> NAME/KEY: MOD_RES
<222> LOCATION: (29)..(29)
<223> OTHER INFORMATION: lysine or proline
<220> FEATURE:
<221> NAME/KEY: MOD_RES
<222> LOCATION: (30)..(30)
<223> OTHER INFORMATION: threonine, alanine, or absent
<220> FEATURE:
<221> NAME/KEY: MOD_RES
<222> LOCATION: (31)..(31)
<223> OTHER INFORMATION: arginine or absent
<220> FEATURE:
<221> NAME/KEY: MOD_RES
<222> LOCATION: (32)..(32)
<223> OTHER INFORMATION: arginine or absent

<400> SEQUENCE: 9

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Xaa Xaa Xaa Xaa Xaa
                20                  25                  30

<210> SEQ ID NO 10
<211> LENGTH: 21
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Urea

<400> SEQUENCE: 10

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 11
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea

<400> SEQUENCE: 11

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (29)..(29)
<223> OTHER INFORMATION: Lys-Urea

<400> SEQUENCE: 12

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Oxopropoxyl acetic acid
<220> FEATURE:
<221> NAME/KEY: MOD_RES
<222> LOCATION: (29)..(29)
```

<223> OTHER INFORMATION: Lys-Oxopropoxyl acetic acid

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Acyl

<400> SEQUENCE: 14

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 15
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Lys-Acyl

<400> SEQUENCE: 15

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 16
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Phenyl acetone

<400> SEQUENCE: 16

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 17
<211> LENGTH: 30
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Phenyl acetone
<220> FEATURE:
<221> NAME/KEY: MOD_RES
<222> LOCATION: (29)..(29)
<223> OTHER INFORMATION: Lys-Phenyl acetone

<400> SEQUENCE: 17

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 18
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Urea
<220> FEATURE:
<221> NAME/KEY: MOD_RES
<222> LOCATION: (14)..(14)
<223> OTHER INFORMATION: Tyr-4-(4-(prop-2-yn-1-yloxy)phenyl)-3H-1,2,4-
      triazole-3,5(4H)-dione

<400> SEQUENCE: 18

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (29)..(29)
<223> OTHER INFORMATION: Lys-Urea

<400> SEQUENCE: 19

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (26)..(26)
<223> OTHER INFORMATION: Tyr-4-(4-(prop-2-yn-1-yloxy)phenyl)-3H-1,2,4-
      triazole-3,5(4H)-dione
<220> FEATURE:
<221> NAME/KEY: MOD_RES
<222> LOCATION: (29)..(29)
<223> OTHER INFORMATION: Lys-Urea

<400> SEQUENCE: 20

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Acyl
<220> FEATURE:
<221> NAME/KEY: MOD_RES
<222> LOCATION: (14)..(14)
<223> OTHER INFORMATION: Tyr-4-(4-(prop-2-yn-1-yloxy)phenyl)-3H-1,2,4-
      triazole-3,5(4H)-dione

<400> SEQUENCE: 21

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Lys-Acyl

<400> SEQUENCE: 22

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (26)..(26)
```

```
<223> OTHER INFORMATION: Tyr-4-(4-(prop-2-yn-1-yloxy)phenyl)-3H-1,2,4-
      triazole-3,5(4H)-dione
<220> FEATURE:
<221> NAME/KEY: MOD_RES
<222> LOCATION: (29)..(29)
<223> OTHER INFORMATION: Lys-Acyl

<400> SEQUENCE: 23

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Urea

<400> SEQUENCE: 24

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (16)..(16)
<223> OTHER INFORMATION: Tyr-4-(4-(prop-2-yn-1-yloxy)phenyl)-3H-1,2,4-
      triazole-3,5(4H)-dione

<400> SEQUENCE: 25

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (26)..(26)
<223> OTHER INFORMATION: Tyr-4-(4-(prop-2-yn-1-yloxy)phenyl)-3H-1,2,4-
      triazole-3,5(4H)-dione
```

<400> SEQUENCE: 26

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea

<400> SEQUENCE: 27

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Urea
<220> FEATURE:
<221> NAME/KEY: MOD_RES
<222> LOCATION: (16)..(16)
<223> OTHER INFORMATION: Tyr-4-(4-(prop-2-yn-1-yloxy)phenyl)-3H-1,2,4-
      triazole-3,5(4H)-dione
<220> FEATURE:
<221> NAME/KEY: MOD_RES
<222> LOCATION: (29)..(29)
<223> OTHER INFORMATION: Lys-Urea

<400> SEQUENCE: 28

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Acyl

<400> SEQUENCE: 29

Gly Ile Val Glu Gln Cys Cys Thr Ser Ile Cys Ser Leu Tyr Gln Leu
1               5                   10                  15

Glu Asn Tyr Cys Asn

```
                                  20

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Tyr-4-(4-(prop-2-yn-1-yloxy)phenyl)-3H-1,2,4-
      triazole-3,5(4H)-dione
<220> FEATURE:
<221> NAME/KEY: MOD_RES
<222> LOCATION: (29)..(29)
<223> OTHER INFORMATION: Lys-Acyl

<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 31
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Tyr-4-(4-(prop-2-yn-1-yloxy)phenyl)-3H-1,2,4-
      triazole-3,5(4H)-dione

<400> SEQUENCE: 31

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Tyr-phenyl-3H-1,2,4-triazoline-3,5-(4H)dione-
      methyl

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MOD_RES
<222> LOCATION: (14)..(14)
<223> OTHER INFORMATION: Tyr-phenyl-3H-1,2,4-triazoline-3,5-(4H)dione-
      methyl

<400> SEQUENCE: 33

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Oxopropoxyl acetic acid
<220> FEATURE:
<221> NAME/KEY: MOD_RES
<222> LOCATION: (29)..(29)
<223> OTHER INFORMATION: Lys-Oxopropoxyl acetic acid

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 35
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Phenyl acetone
<220> FEATURE:
<221> NAME/KEY: MOD_RES
<222> LOCATION: (14)..(14)
<223> OTHER INFORMATION: Tyr-4-(4-(prop-2-yn-1-yloxy)phenyl)-3H-1,2,4-
      triazole-3,5(4H)-dione

<400> SEQUENCE: 35

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe-Phenyl acetone
<220> FEATURE:
```

```
<221> NAME/KEY: MOD_RES
<222> LOCATION: (29)..(29)
<223> OTHER INFORMATION: Lys-Phenyl acetone

<400> SEQUENCE: 36

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 37
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Urea
<220> FEATURE:
<221> NAME/KEY: MOD_RES
<222> LOCATION: (14)..(14)
<223> OTHER INFORMATION: Tyr-4-(4-(trifluoromethoxy)phenyl)-3H-1,2,4-
      triazole-3,5(4H)-dione

<400> SEQUENCE: 37

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 38
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly-Urea
<220> FEATURE:
<221> NAME/KEY: MOD_RES
<222> LOCATION: (14)..(14)
<223> OTHER INFORMATION: Tyr-4-(4-(trifluoromethoxy)phenyl)-3H-1,2,4-
      triazole-3,5(4H)-dione
<220> FEATURE:
<221> NAME/KEY: MOD_RES
<222> LOCATION: (19)..(19)
<223> OTHER INFORMATION: Tyr-4-(4-(prop-2-yn-1-yloxy)phenyl)-3H-1,2,4-
      triazole-3,5(4H)-dione

<400> SEQUENCE: 38

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gly-Urea
<220> FEATURE:
<221> NAME/KEY: MOD_RES
<222> LOCATION: (14)..(14)
<223> OTHER INFORMATION: Tyr-4-(4-(pentyloxy)phenyl)-3H-1,2,4-triazole-
      3,5(4H)-dione

<400> SEQUENCE: 39

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 40
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Tyr-4-(4-(pentyloxy)phenyl)-3H-1,2,4-triazole-
      3,5(4H)-dione

<400> SEQUENCE: 40

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Tyr-4-(4-(2-azidoethoxy)phenyl)-3H-1,2,4-
      triazole-3,5(4H)-dione

<400> SEQUENCE: 41

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly with side group H, CONH2, COCH3, or
      COCH2(C6H5)

<400> SEQUENCE: 42

Gly Ile Val Glu Gln Cys Cys Thr Ser Ile Cys Ser Leu Tyr Gln Leu
1               5                   10                  15
```

Glu Asn Tyr Cys Asn
        20

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Phe with side group H, CONH2, COCH2OCH2CO2H, or
      COCH2(C6H5)
<220> FEATURE:
<221> NAME/KEY: MOD_RES
<222> LOCATION: (29)..(29)
<223> OTHER INFORMATION: Lys with side group H, CONH2, COCH2OCH2CO2H,
      COCH3, or COCH2(C6H5)

<400> SEQUENCE: 43

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 44
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly with side group H, CONH2, COCH3, or
      COCH2(C6H5)
<220> FEATURE:
<221> NAME/KEY: MOD_RES
<222> LOCATION: (14)..(14)
<223> OTHER INFORMATION: Tyr-3H-1,2,4-Triazole-3,5(4H)-dione
<220> FEATURE:
<221> NAME/KEY: MOD_RES
<222> LOCATION: (19)..(19)
<223> OTHER INFORMATION: Tyr-3H-1,2,4-Triazole-3,5(4H)-dione

<400> SEQUENCE: 44

Gly Ile Val Glu Gln Cys Cys Thr Ser Ile Cys Ser Leu Tyr Gln Leu
1               5                   10                  15

Glu Asn Tyr Cys Asn
        20

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (1)..(1)
<223> OTHER INFORMATION: Phe with side group H, CONH2, COCH2OCH2CO2H, or
      COCH2(C6H5)
<220> FEATURE:
<221> NAME/KEY: MOD_RES
<222> LOCATION: (16)..(16)
<223> OTHER INFORMATION: Tyr-3H-1,2,4-Triazole-3,5(4H)-dione
<220> FEATURE:
<221> NAME/KEY: MOD_RES
<222> LOCATION: (26)..(26)
<223> OTHER INFORMATION: Tyr-3H-1,2,4-Triazole-3,5(4H)-dione
<220> FEATURE:
<221> NAME/KEY: MOD_RES
<222> LOCATION: (29)..(29)
<223> OTHER INFORMATION: Lys with side group H, CONH2, COCH2OCH2CO2H,
      COCH3, or COCH2(C6H5)

<400> SEQUENCE: 45

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

TYROSINE-SPECIFIC FUNCTIONALIZED INSULIN AND INSULIN ANALOGS

REFERENCE TO SEQUENCE LISTING SUBMITTED ELECTRONICALLY

The sequence listing of the present application is submitted electronically via EFS-Web as an ASCII formatted sequence listing with a file name 24576-US-PCT_SL.txt, creation date of Dec. 10, 2021, and size of 23,964 bytes. This sequence listing submitted via EFS-Web is part of the specification and is herein incorporated by reference in its entirety.

FIELD

The present invention relates to tyrosine-specific functionalized insulin analogs and processes of making such tyrosine-specific functionalized insulin analogs using R-3H-1,2,4-triazoline-3,5-(4H)diones (RTADs). The present invention further relates to utilization of tyrosine-specific functionalization through R-3H-1,2,4-trizoline-3,5-(4H)diones (RTADs) to modify insulin and insulin analogs for use in imaging or preparing insulin conjugates (such as PEG, glycosylate) or dimers.

BACKGROUND

Late Stage Functionalization (LSF) of both "small" and "large" molecules focuses on the derivatization of a drug molecule in a very specific and selective way. This strategy allows modification of the molecule in a few steps without the need for de novo synthesis. LSF tools include C—H functionalization for halogenation, borylation, oxidation, or alkylation/arylation. Applying these techniques to target amino acid residues in native peptides and proteins, however, is challenging due to the potential for many reactive sites and complicated purification and analysis. The most common functional groups for modification on a protein are amine (from Lys and the N-terminus), sulfhydryl (from Cys), carboxylic acid (from C-terminus or Asp and Glu) and hydroxyl (from Thr, Ser or Tyr). The ability to achieve site-specific modification provides better control for protein labeling (fluorophores, biotins) and bioconjugation (dimerization, PEGylation).

Therefore, there is a need for methods to selectively functionalize a tyrosine amino acid in the presence of other amino acids. Functionalization of the phenol side chain of tyrosine by RTADs allows for many possibilities: modifications for X-ray and NMR studies, expansion of chemical SAR, alteration of PKPD properties, tools for biochemical assays or bioconjugation/linker installation.

BRIEF SUMMARY OF THE INVENTION

The present invention provides tyrosine functionalized insulin analogs and processes for making such analogs using R-3H-1,2,4-triazoline-3,5-(4H)diones (RTADs), wherein R is methyl,

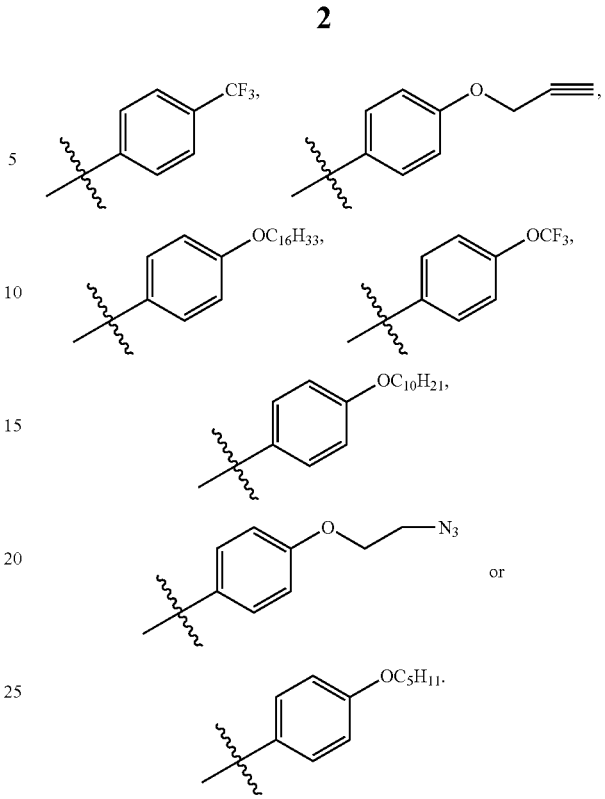

Thus, the present invention provides the following embodiments, a process of making a tyrosine functionalized insulin analog comprising modifying a tyrosine amino acid on an insulin or insulin analog using R-3H-1,2,4-triazoline-3,5-(4H)diones. In other embodiments of the processes described herein, the process described herein includes the following steps introducing insulin or an insulin analog to a solvent system; cooling the insulin or insulin analog and solvent system; and adding a R-3H-1,2,4-triazoline-3,5-(4H)diones. In certain embodiments of the processes described herein, comprise the steps of introducing the insulin or insulin analog to a solvent system; cooling the insulin or insulin analog and solvent system between below room temperature and −10° C.; and adding a R-3H-1,2,4-triazoline-3,5-(4H)dione. In certain embodiments the process described herein includes the following steps introducing insulin or an insulin analog to a solvent system, wherein the solvent system has a pH between 7-9; cooling the insulin or insulin analog and solvent system to a temperature between below room temperature and −10° C.; adding a R-3H-1,2,4-triazoline-3,5-(4H)dione; and raising the pH of the mixture to between 2-5.

In certain embodiments of the processes described herein, the insulin or insulin analog is

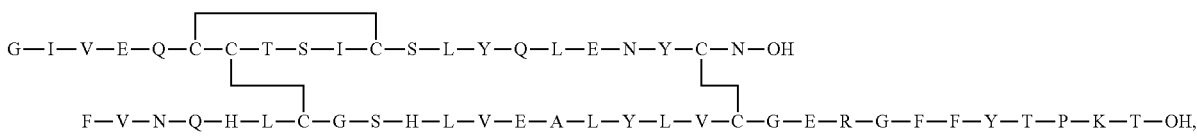

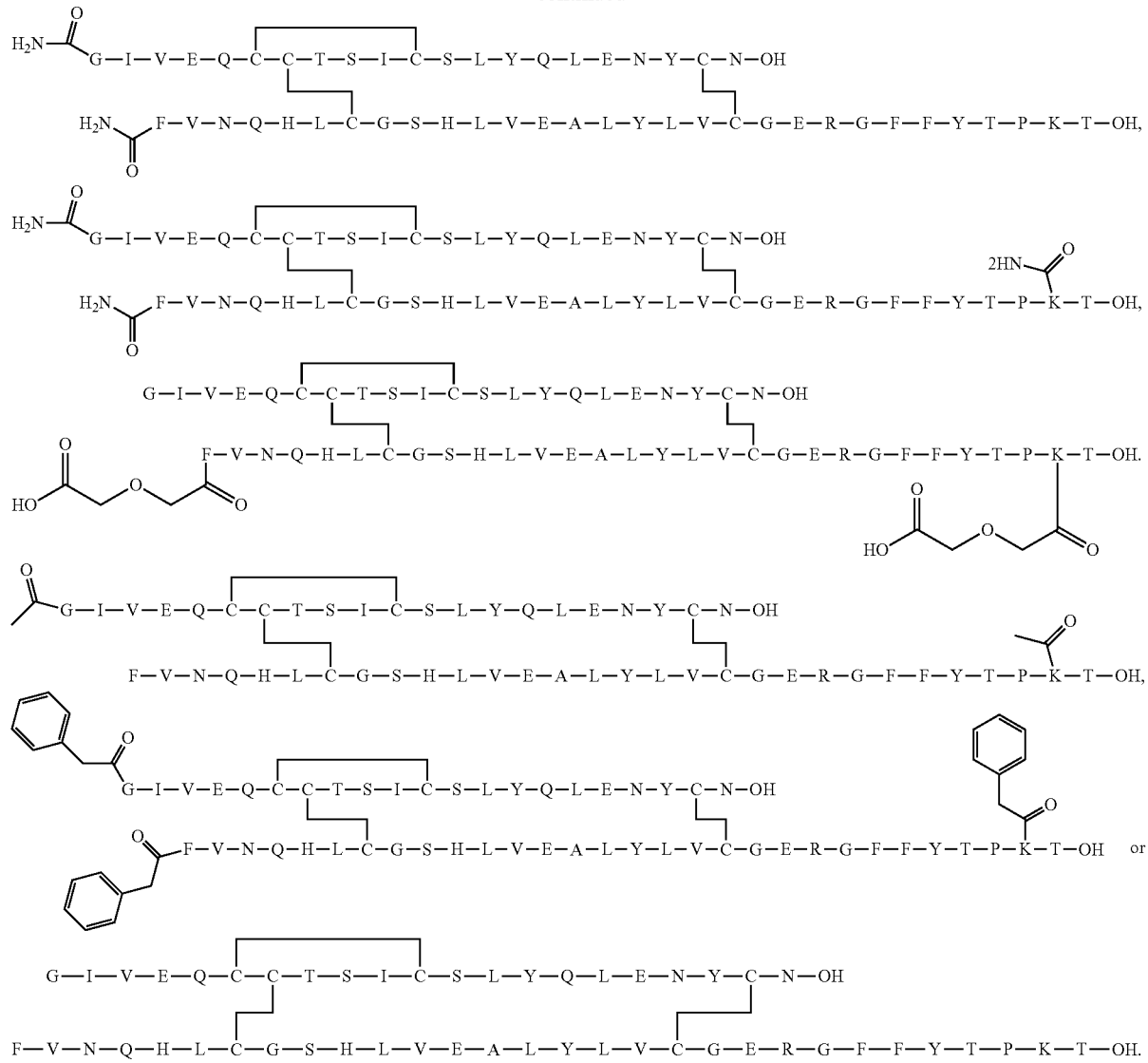

SEQ ID NOS 1, 2, 10, 11, 10, 12, 1, 13-17, 1, and 4 are disclosed above, respectively, in order of appearance.

In certain embodiments of the processes described herein, the insulin or insulin analog is recombinant human insulin.

Human insulin, in its native form, and certain insulin analogs have a total of four tyrosine amino acids, two on the A chain, at A14 and A19 and two on the B chain, at B16 and B26. In certain embodiments of the processes described herein, the A14 tyrosine on the human insulin or insulin analog is functionalized. In certain embodiments of the processes described herein, the A19 tyrosine on the human insulin or insul1in analog is functionalized. In certain embodiments of the processes described herein, the B16 tyrosine on the human insulin or insulin analog is functionalized. In certain embodiments of the processes described herein, the B26 tyrosine on the human insulin or insulin analog is functionalized.

In certain embodiments of the processes described herein, the A14 and A19 tyrosine on the human insulin or insulin analog are functionalized. In certain embodiments of the processes described herein, the A14 and B16 tyrosine on the human insulin or insulin analog are functionalized. In certain embodiments of the processes described herein, the A14 and B26 tyrosine on the human insulin or insulin analog are functionalized. In certain embodiments of the processes described herein, the A19 and B16 tyrosine on the human insulin or insulin analog are functionalized. In certain embodiments of the processes described herein, the A19 and B26 tyrosine on the human insulin or insulin analog are functionalized. In certain embodiments of the processes described herein, the A19 and B26 tyrosine on the human insulin or insulin analog are functionalized. In certain embodiments of the processes described herein, the B16 and B26 tyrosine on the human insulin or insulin analog are functionalized.

In certain embodiments of the processes described herein, the A14, B16 and B26 tyrosine on the human insulin or insulin analog are functionalized. In certain embodiments of the processes described herein, the A19, B16 and B26 tyrosine on the human insulin or insulin analog are functionalized. In certain embodiments of the processes described herein, the A14, A19 and B26 tyrosine on the human insulin or insulin analog are functionalized. In certain embodiments of the processes described herein, the A14, A19 and B16 tyrosine on the human insulin or insulin analog are functionalized.

In certain embodiments of the processes described herein, the R-3H-1,2,4-triazoline-3,5-(4H)dione is a compound of Formula I.

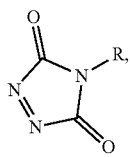

wherein R is methyl,

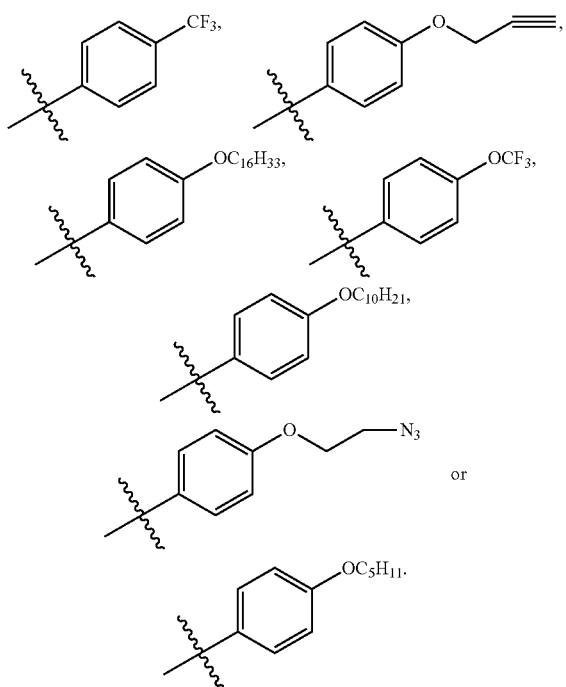

In certain processes described herein, the solvent system is a mixture of acetonitrile and sodium phosphate buffer. In certain embodiments of the processes described herein, the pH is maintained between 7-9.

DESCRIPTION

Definitions

Insulin—as used herein, the term means the active principle of the pancreas that affects the metabolism of carbohydrates in the animal body and which is of value in the treatment of diabetes mellitus. The term includes synthetic and biotechnologically derived products that are the same as, or similar to, naturally occurring insulins in structure, use, and intended effect and are of value in the treatment of diabetes mellitus. The term is a generic term that designates the 51 amino acid heterodimer comprising the A-chain peptide having the amino acid sequence shown in SEQ ID NO: 1 and the B-chain peptide having the amino acid sequence shown in SEQ ID NO: 2, wherein the cysteine residues at positions 6 and 11 of the A chain are linked in a disulfide bond, the cysteine residues at position 7 of the A chain and position 7 of the B chain are linked in a disulfide bond, and the cysteine residues at position 20 of the A chain and 19 of the B chain are linked in a disulfide bond.

Insulin analog or analogue—the term as used herein includes any heterodimer analogue or single-chain analogue that comprises one or more modification(s) of the native A-chain peptide and/or B-chain peptide. Modifications include but are not limited to substituting an amino acid for the native amino acid at a position selected from A4, A5, A8, A9, A10, A12, A13, A14, A15, A16, A17, A18, A19, A21, B1, B2, B3, B4, B5, B9, B10, B13, B14, B15, B16, B17, B18, B20, B21, B22, B23, B26, B27, B28, B29, and B30; deleting any or all of positions B1-4 and B26-30; or conjugating directly or by a polymeric or non-polymeric linker one or more acyl, polyethylglycine (PEG), or saccharide moiety (moieties); or any combination thereof. Examples of insulin analogues include but are not limited to the heterodimer and single-chain analogues disclosed in published international application WO2010/080606, WO2009/099763, and WO2010/080609, the disclosures of which are incorporated herein by reference. Examples of single-chain insulin analogues also include but are not limited to those disclosed in published International Applications WO96/34882, WO95/516708, WO2005/054291, WO2006/097521, WO2007/104734, WO2007/104736, WO2007/104737, WO2007/104738, WO2007/096332, WO2009/132129; U.S. Pat. Nos. 5,304,473 and 6,630,348; and Kristensen et al., Biochem. J. 305: 981-986 (1995), the disclosures of which are each incorporated herein by reference.

The term further includes single-chain and heterodimer polypeptide molecules that have little or no detectable activity at the insulin receptor but which have been modified to include one or more amino acid modifications or substitutions to have an activity at the insulin receptor that has at least 1%, 10%, 50%, 75%, or 90% of the activity at the insulin receptor as compared to native insulin. In particular aspects, the insulin analogue is a partial agonist that has less than 80% (or 70%) activity at the insulin receptor as does native insulin. These insulin analogues, which have reduced activity at the insulin growth hormone receptor and enhanced activity at the insulin receptor, include both heterodimers and single-chain analogues.

Single-chain insulin or single-chain insulin analog—as used herein, the term encompasses a group of structurally-related proteins wherein the A-chain peptide or functional analogue and the B-chain peptide or functional analogue are covalently linked by a peptide or polypeptide of 2 to 35 amino acids or non-peptide polymeric or non-polymeric linker and which has at least 1%, 10%, 50%, 75%, or 90% of the activity of insulin at the insulin receptor as compared to native insulin. The single-chain insulin or insulin analogue further includes three disulfide bonds: the first disulfide bond is between the cysteine residues at positions 6 and 11 of the A-chain or functional analogue thereof, the second disulfide bond is between the cysteine residues at position 7 of the A-chain or functional analogue thereof and position 7 of the B-chain or functional analogue thereof, and the third disulfide bond is between the cysteine residues at position 20 of the A-chain or functional analogue thereof and position 19 of the B-chain or functional analogue thereof.

Heterodimer: as used herein, the term includes any protein composed of two polypeptide chains differing in composition in the order, number, or kind of their amino acid residues Tyrosine functionalized insulin analog—as used herein, the term encompasses insulin analogs that were made according to the processes described herein.

Pharmaceutically acceptable carrier—as used herein, the term includes any of the standard pharmaceutical carriers, such as a phosphate buffered saline solution, water, emulsions such as an oil/water or water/oil emulsion, and various types of wetting agents suitable for administration to or by an individual in need. The term also encompasses any of the agents approved by a regulatory agency of the US Federal government or listed in the US Pharmacopeia for use in animals, including humans.

Pharmaceutically acceptable salt—as used herein, the term refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium, zinc, and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include, but are not limited to, hydrochloric acid, hydrobromic acid, sulfuric acid, nitric acid, phosphoric acid, and the like. Salts derived from organic acids include, but are not limited to, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Effective or therapeutically effective amount—as used herein refers to a nontoxic but sufficient amount of an insulin analog to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." It is not always possible to determine the optimal effective amount prior to administration to or by an individual in need thereof. However, an appropriate "effective" amount in any individual case may be determined by one of ordinary skill in the art using routine experimentation.

Parenteral—as used herein, the term means not through the alimentary canal but by some other route such as intranasal, inhalation, subcutaneous, intramuscular, intraspinal, or intravenous.

Tyrosine Functionalization Process

The present invention is directed to tyrosine functionalized insulin analogs and processes of making such tyrosine functionalized insulin analogs. The processes described herein include functionalization of a tyrosine amino acid of insulin or an insulin analog using R-3H-1,2,4-triazoline-3,5-(4H)dione wherein R is methyl,

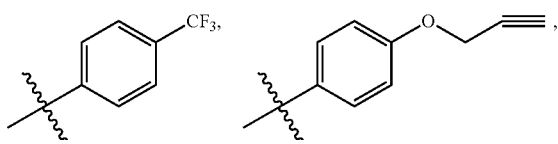

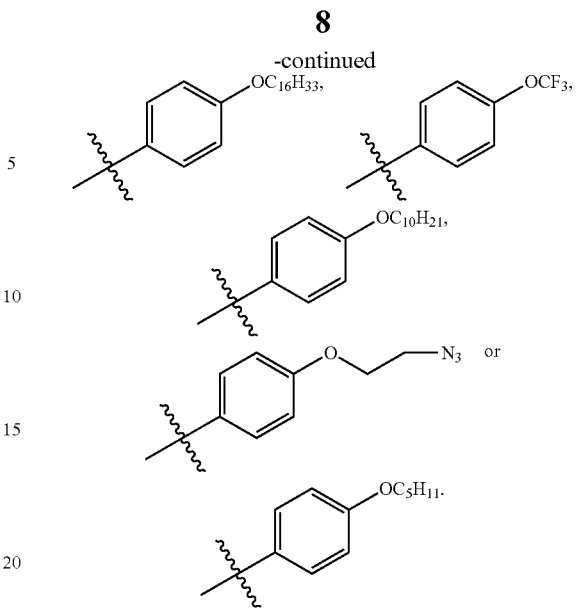

In certain embodiments the process described herein includes the following steps:
  introducing insulin or an insulin analog to a solvent system;
  cooling the insulin or insulin analog and solvent system to a temperature between below room temperature and −10° C.; and
  adding a R-3H-1,2,4-triazoline-3,5-(4H)dione to the cooled mixture of insulin or insulin analog and solvent system.

In certain embodiments the process described herein includes the following steps:
  introducing insulin or an insulin analog to a solvent system;
  cooling the insulin or insulin analog and solvent system; and
  adding a R-3H-1,2,4-triazoline-3,5-(4H)dione to the cooled mixture of insulin or insulin analog and solvent system.

In certain embodiments the process described herein includes the following steps:
  introducing insulin or an insulin analog to a solvent system, wherein the solvent system has a pH between 7-9;
  cooling the insulin or insulin analog and solvent system to a temperature between below room temperature and −10° C.;
  adding a R-3H-1,2,4-triazoline-3,5-(4H)dione to the cooled mixture of insulin or insulin analog and solvent system; and
  raising the pH of the mixture to between 2-5.

In the processes described herein, the R-3H-1,2,4-triazoline-3,5-(4H)dione can be a compound of Formula I:

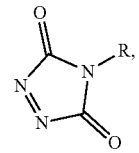

wherein R is methyl

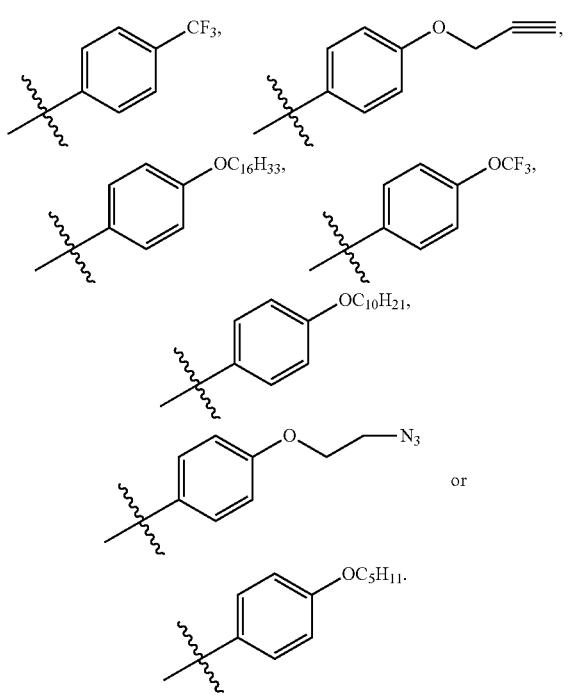

In the process described herein, the solvent system can comprise of any suitable solvent including, but not limited to, water, acetonitrile, methanol (MeOH), isopropyl alcohol (iPrOH), tert-butanol (tBuOH), tert-amyl alcohol (tAmylOH) and dimethylacetamide (DMAc), or a combination thereof.

In certain embodiments, the solvent system of the processes described herein can be a combination of two or more solvents in optimal rations. Suitable ratios include, but are not limited to, 9:1, 4:1, 7:3, 3:2, 1:1, 2:3, 3:7; 1:4 and 1:9.

In certain embodiments, the solvent system is a combination of acetonitrile and water/salt buffer. A suitable ratio of acetonitrile and water/salt buffer can include, but is not limited to, 9:1, 8:2, 7:3, 6:4, 5:5, 4:6, 3:7; 2:8 and 1:9. In certain embodiments, the solvent system is a combination of acetonitrile and water/salt buffer in a ratio of 9:1.

In certain embodiments, the solvent system is acetonitrile.

In the processes described herein the solvent system is at a pH between 5-10. In certain embodiments the solvent system used in the processes described herein is at a pH between 6-10. In certain embodiments the solvent system used in the processes described herein is at a pH between 7-10. In certain embodiments the solvent system used in the processes described herein is at a pH between 8-10. In certain embodiments the solvent system used in the processes described herein is at a pH between 9-10. In certain embodiments the solvent system used in the processes described herein is at a pH between 6-9. In certain embodiments the solvent system used in the processes described herein is at a pH between 6-8. In certain embodiments the solvent system used in the processes described herein is at a pH between 6-7. In certain embodiments the solvent system used in the processes described herein is at a pH between 8-9.

In certain embodiments the solvent system used in the processes described herein is at a pH of 6. In certain embodiments the solvent system used in the processes described herein is at a pH of 7. In certain embodiments the solvent system used in the processes described herein is at a pH of 8. In certain embodiments the solvent system used in the processes described herein is at a pH of 9. In certain embodiments the solvent system used in the processes described herein is at a pH of 10.

In certain embodiments the solvent system used in the processes described herein is at a pH of 6.5. In certain embodiments the solvent system used in the processes described herein is at a pH of 7.5. In certain embodiments the solvent system used in the processes described herein is at a pH of 8.5. In certain embodiments the solvent system used in the processes described herein is at a pH of 9.5. In certain embodiments the solvent system used in the processes described herein is at a pH of 10.5.

The solvent system can be adjusted or kept at the desired pH by using pH buffers. Buffers can be added at the beginning of the reaction or during the reaction, as needed, to keep the pH of the system at the desired pH. Suitable buffers include, but are not limited to, sodium bicarbonate, sodium phosphate, sodium potassium phosphate, sodium acetate, or sodium bicarbonate/sodium carbonate ($Na_2CO_3$/$NaHCO_3$).

In certain embodiments of the processes described herein, once the reaction is complete, the mixture is concentrated by reducing the volume of the mixture and the pH lowered. The pH of the reaction mixture is lowered by adding in an acid or other proton donating compound. Suitable acids include, but are not limited to, trifluoroacetic acid (TFA), hydrochloric acid (HCl) or phosphoric acid.

Though the chemistry processes described herein can be used on any peptide or protein with a free amine, the processes and examples described herein are used in conjunction with insulin or insulin analogs.

Suitable types of insulin that can be used in the processes described herein include, but are not limited to, recombinant human insulin (RHI) and native human insulin.

As for insulin analogs, one type of insulin analog that can be used in the processes described herein, "monomeric insulin analog," is well known in the art. These are fast-acting analogs of human insulin, including, for example, insulin analogs wherein:

(a) the amino acyl residue at position B28 is substituted with Asp, Lys, Leu, Val, or Ala, and the amino acyl residue at position B29 is Lys or Pro;

(b) the amino acyl residues at any of positions B27 and B30 are deleted or substituted with a nonnative amino acid.

In one embodiment an insulin analog that can be used in the processes described herein, is provided comprising an Asp substituted at position B28 (e.g., insulin aspart (NOVOLOG); see SEQ ID NO:3) or a Lys substituted at position 28 and a proline substituted at position B29 (e.g., insulin lispro (HUMALOG); see SEQ ID NO:4). Additional monomeric insulin analogs are disclosed in Chance, et al., U.S. Pat. No. 5,514,646; Chance, et al., U.S. patent application Ser. No. 08/255,297; Brems, et al., Protein Engineering, 5:527-533 (1992); Brange, et al., EPO Publication No. 214,826 (published Mar. 18, 1987); and Brange, et al., Current Opinion in Structural Biology, 1:934-940 (1991). These disclosures are expressly incorporated herein by reference for describing monomeric insulin analogs.

Insulin analogs that can be used in the processes described herein may also have replacements of the amidated amino acids with acidic forms. For example, Asn may be replaced with Asp or Glu. Likewise, Gln may be replaced with Asp or Glu. In particular, Asn(A18), Asn(A21), or Asp(B3), or any combination of those residues, may be replaced by Asp or Glu. Also, Gln(A15) or Gln(B4), or both, may be replaced by either Asp or Glu.

In one embodiment the insulin analogs that can be used in the processes described herein have the A chain comprising amino acid sequence GIVEQCCTSICSLYQLENYCN (SEQ ID NO: 1 and the B chain comprising amino acid sequence FVNQHLCGSHLVEALYLV CGERGFFYTPKT (SEQ ID NO: 2) or a carboxy shortened sequence thereof having B30 deleted, and analogs of those sequences wherein each sequence is modified to comprise one to five amino acid substitutions at positions corresponding to native insulin positions selected from A5, A8, A9, A10, A14, A15, A17, A18, A21, B1, B2, B3, B4, B5, B9, B10, B13, B14, B20, B22, B23, B26, B27, B28, B29 and B30, with the proviso that at least one of B28 or B29 is lysine. In one embodiment the amino acid substitutions of the insulin analogs that can be used in the processes described herein are conservative amino acid substitutions. Suitable amino acid substitutions at these positions that do not adversely impact insulin's desired activities are known to those skilled in the art, as demonstrated, for example, in Mayer, et al., Insulin Structure and Function, Biopolymers. 2007; 88(5):687-713, the disclosure of which is incorporated herein by reference.

In accordance with one embodiment the insulin analog peptides that can be used in the processes described herein may comprise an insulin A chain and an insulin B chain or analogs thereof, wherein the A chain comprises an amino acid sequence that shares at least 70% sequence identity (e.g., 70%, 75%, 80%, 85%, 90%, 95%) over the length of the native peptide, with GIVEQCCTSICSLYQLENYCN (SEQ ID NO: 1) and the B chain comprises an amino acid sequence that shares at least 60% sequence identity (e.g., 60%, 65%, 70%, 75%, 80%, 85%, 90%, 95%) over the length of the native peptide, with FVNQHLCGSHLVEALYLVC GERGFFYTPKT (SEQ ID NO: 2) or a carboxy shortened sequence thereof having B30 deleted.

Additional amino acid sequences can be added to the amino terminus of the B chain or to the carboxy terminus of the A chain of the insulin polypeptides of insulin analogs that can be used in the processes described herein. For example, a series of negatively charged amino acids can be added to the amino terminus of the B chain, including for example a peptide of 1 to 12, 1 to 10, 1 to 8 or 1 to 6 amino acids in lengt1h and comprising one or more negatively charged amino acids including for example glutamic acid and aspartic acid. In one embodiment the B chain amino terminal extension comprises 1 to 6 charged amino acids. In accordance with one embodiment the insulin polypeptides disclosed comprise a C-terminal amide or ester in place of a C-terminal carboxylate on the A chain.

In various embodiments, the insulin analogs that can be used in the processes described herein have an isoelectric point that has been shifted relative to human insulin. In some embodiments, the shift in isoelectric point is achieved by adding one or more arginine, lysine, or histidine residues to the N-terminus of the insulin A-chain peptide and/or the C-terminus of the insulin B-chain peptide. Examples of such insulin polypeptides include $Arg^{A0}$-human insulin, $Arg^{B31}Arg^{B32}$-human insulin, $Gly^{A21}Arg^{B31}Arg^{B32}$-human insulin, $Arg^{A0}Arg^{B31}Arg^{B32}$-human insulin, and $Arg^{A0}Gly^{A21}Arg^{B31}Arg^{B32}$-human insulin. By way of further example, insulin glargine (LANTUS; see SEQ ID NOs: 5 and 6) is an exemplary long-acting insulin analog in which $Asn^{A21}$ has been replaced by glycine, and two arginine residues have been covalently linked to the C-terminus of the B-peptide. The effect of these amino acid changes was to shift the isoelectric point of the molecule, thereby producing a molecule that is soluble at acidic pH (e.g., pH 4 to 6.5) but insoluble at physiological pH. When a solution of insulin glargine is injected into the muscle, the pH of the solution is neutralized and the insulin glargine forms microprecipitates that slowly release the insulin glargine over the 24 hour period following injection with no pronounced insulin peak and thus a reduced risk of inducing hypoglycemia. This profile allows a once-daily dosing to provide a patient's basal insulin. Thus, in some embodiments, the insulin analogs that can be used in the processes described herein comprise an A-chain peptide wherein the amino acid at position A21 is glycine and a B-chain peptide wherein the amino acids at position B31 and B32 are arginine. The present disclosure encompasses all single and multiple combinations of these mutations and any other mutations that are described herein (e.g., $Gly^{A21}$-human insulin, $Gly^{A21}Arg^{B31}$-human insulin, $Arg^{B31}Arg^{B32}$-human insulin, $Arg^{B31}$-human insulin).

In certain embodiments of the insulin analogs that can be used in the processes described herein, one or more amidated amino acids of the insulin analog are replaced with an acidic amino acid, or another amino acid. For example, asparagine may be replaced with aspartic acid or glutamic acid, or another residue. Likewise, glutamine may be replaced with aspartic acid or glutamic acid, or another residue. In particular, $Asn^{A18}$, $Asn^{A21}$, or $Asn^{B3}$, or any combination of those residues, may be replaced by aspartic acid or glutamic acid, or another residue. $Gln^{A15}$ or $Gln^{B4}$, or both, may be replaced by aspartic acid or glutamic acid, or another residue. In particular aspects of the insulin receptor partial agonists, the insulin analogs have an aspartic acid, or another residue, at position A21 or aspartic acid, or another residue, at position B3, or both.

One skilled in the art will recognize that it is possible to replace yet other amino acids in the insulin analog that can be used in the processes described herein with other amino acids while retaining biological activity of the molecule. For example, without limitation, the following modifications are also widely accepted in the art: replacement of the histidine residue of position B10 with aspartic acid ($His^{B10}$ to $Asp^{B10}$); replacement of the phenylalanine residue at position B1 with aspartic acid ($Phe^{B1}$ to $Asp^{B1}$); replacement of the threonine residue at position B30 with alanine ($Thr^{B30}$ to $Ala^{B30}$); replacement of the tyrosine residue at position B26 with alanine ($Tyr^{B26}$ to $Ala^{B26}$); and replacement of the serine residue at position B9 with aspartic acid ($Ser^{B9}$ to $Asp^{B9}$).

In certain embodiments, the insulin analogs that can be used in the processes described herein may be acylated with a fatty acid. That is, an amide bond is formed between an amino group on the insulin analog and the carboxylic acid group of the fatty acid. The amino group may be the alpha-amino group of an N-terminal amino acid of the insulin analog, or may be the epsilon-amino group of a lysine residue of the insulin analog. The insulin analog may be acylated at one or more of the three amino groups that are present in wild-type human insulin may be acylated on lysine residue that has been introduced into the wild-type human insulin sequence. In certain embodiments, the insulin analogs that can be used in the processes described herein may be acylated at position A1, B1, or $Lys^{B29}$ or both A1 and B1. In certain embodiments, the fatty acid is selected from myristic acid ($C_{14}$), pentadecylic acid ($C_{15}$), palmitic acid ($C_{16}$), heptadecylic acid ($C_{17}$) and stearic acid ($C_{18}$).

Examples of insulin analogs that can be used in the processes described herein can be found for example in published International Application WO9634882, WO95516708; WO2010/0080606, WO2009/099763, and WO2010/080609, U.S. Pat. No. 6,630,348, and Kristensen et al., Biochem. J. 305: 981-986 (1995), the disclosures of which are incorporated herein by reference). In further embodiments, the in vitro glycosylated or in vivo N-glycosylated insulin analogs may be acylated and/or pegylated.

In certain embodiments, an insulin analog that can be used in the processes described herein is provided wherein the A chain of the insulin peptide comprises the sequence GIVEQCCX$_8$SICSLYQLX$_{17}$NX$_{19}$CX$_{23}$ (SEQ ID NO: 7) and the B chain comprising the sequence X$_{25}$LCGX$_{29}$X$_{30}$LVEALYLVCGERGFFYTX$_{31}$X$_{32}$ (SEQ ID NO: 8) wherein $X_8$ is threonine or histidine;
$X_{17}$ is glutamic acid or glutamine;
$X_{19}$ is tyrosine, 4-methoxy-phenylalanine, or 4-amino phenylalanine;
$X_{23}$ is asparagine or glycine;
$X_{25}$ is histidine or threonine;
$X_{29}$ is alanine, glycine or serine;
$X_{30}$ is histidine, aspartic acid, glutamic acid, homocysteic acid, or cysteic acid;
$X_{31}$ is proline or lysine; and
$X_{32}$ is proline or lysine, with the proviso that at least one of $X_{31}$ or $X_{32}$ is lysine.

In a further embodiment, an insulin analog that can be used in the processes described herein the B chain comprises the sequence (SEQ ID NO: 9)
X$_{22}$VNQX$_{25}$LCGX$_{29}$X$_{30}$LVEALYLVCGERGFFYT-X$_{31}$X$_{32}$X$_{33}$X$_{34}$
X$_{35}$ wherein
$X_{22}$ is phenylalanine or desamino-phenylalanine;
$X_{25}$ is histidine or threonine;
$X_{29}$ is alanine, glycine, or serine;
$X_{30}$ is histidine, aspartic acid, glutamic acid, homocysteic acid, or cysteic acid;
$X_{31}$ is aspartic acid, proline, or lysine;
$X_{32}$ is lysine or proline;
$X_{33}$ is threonine, alanine, or absent;
$X_{34}$ is arginine or absent; and
$X_{35}$ is arginine or absent;
With the proviso at least one of $X_{31}$ or $X_{32}$ is lysine.

In certain embodiments, the processes described herein include: combining insulin or an insulin analog with 1:1/Acetonitrile:1001 mM Sodium Phosphate buffer pH 7.5; cooling the reaction mixture in a salt/ice bath to −5° C.; adding a solution of R-3H-1,2,4-triazole-3,5(4H)-dione in anhydrous acetonitrile (0.045 M), wherein R is described above.

In certain embodiments the processes described herein, further comprise further reducing the reaction mixture and adjusting the pH to 2-2.5 with TFA.

In certain embodiments, one or all of existing free amines on the insulin or insulin analog can be protected. Various protection methods are known in the art.

Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, NN'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Processes of Making Tyrosine Functionalized Insulin Analogs with Recombinant Human Insulin (RHI)

In certain embodiments, the present invention relates to tyrosine functionalized RHI and processes of making such tyrosine functionalized insulin analogs using a R-3H-1,2,4-triazoline-3,5-(4H)dione.

In certain embodiments described herein, one, two, three or four of the tyrosines on RHI are functionalized. In certain embodiments described herein, one of the tyrosines on RHI is functionalized. In certain embodiments described herein, two of the tyrosines on RHI are functionalized. In certain embodiments described herein, three of the tyrosines on RHI are functionalized. In certain embodiments described herein, all four of the tyrosines on RHI are functionalized.

RHI has a total of four tyrosine amino acids, two on the A chain, at A14 and A19, and two on the B chain, at B16 and B26. In certain embodiments of the processes described herein, the A14 tyrosine on RHI is functionalized. In certain embodiments of the processes described herein, the A19 tyrosine on RHI is functionalized. In certain embodiments of the processes described herein, the B16 tyrosine on RHI is functionalized. In certain embodiments of the processes described herein, the B26 tyrosine on RHI is functionalized.

In certain embodiments of the processes described herein, the A14 and A19 tyrosine on RHI are functionalized. In certain embodiments of the processes described herein, the A14 and B16 tyrosine on RHI are functionalized. In certain embodiments of the processes described herein, the A14 and B26 tyrosine on RHI are functionalized. In certain embodiments of the processes described herein, the A19 and B16 tyrosine on RHI are functionalized. In certain embodiments of the processes described herein, the A19 and B26 tyrosine on RHI are functionalized. In certain embodiments of the processes described herein, the A19 and B26 tyrosine on RHI are functionalized. In certain embodiments of the processes described herein, the B16 and B26 tyrosine on RHI are functionalized.

In certain embodiments of the processes described herein, the A14, B16 and B26 tyrosine on RHI are functionalized. In certain embodiments of the processes described herein, the A19, B16 and B26 tyrosine on RHI are functionalized. In certain embodiments of the processes described herein, the A14, A19 and B26 tyrosine on RHI are functionalized. In certain embodiments of the processes described herein, the A14, A19 and B16 tyrosine on RHI are functionalized.

In certain embodiments, the present invention is directed to tyrosine functionalized RHI and processes of making such tyrosine functionalized RHI. The processes described herein include functionalization of a tyrosine amino acid of RHI using R-3H-1,2,4-triazoline-3,5-(4H)dione.

In certain embodiments the process described herein includes the following steps:
  introducing RHI to a solvent system;
  cooling the RHI and solvent system to a temperature between below room temperature and −10° C.; and
  adding a R-3H-1,2,4-triazoline-3,5-(4H)dione to the cooled mixture of insulin or insulin analog and solvent system.

In certain embodiments the process described herein includes the following steps:
  introducing RHI to a solvent system;
  cooling the RHI and solvent system; and
  adding a R-3H-1,2,4-triazoline-3,5-(4H)dione to the cooled mixture of insulin or insulin analog and solvent system.

In certain embodiments the process described herein includes the following steps:
  introducing RHI to a solvent system, wherein the solvent system has a pH between 7-9;
  cooling the RHI and solvent system to a temperature between below room temperature and −10° C.;
  adding a R-3H-1,2,4-triazoline-3,5-(4H)dione to the cooled mixture of insulin or insulin analog and solvent system; and
  raising the pH of the mixture to between 2-5.

In the processes described herein, the R-3H-1,2,4-triazoline-3,5-(4H)dione can be a compound of Formula I:

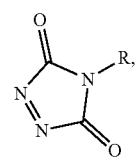

wherein R is methyl,

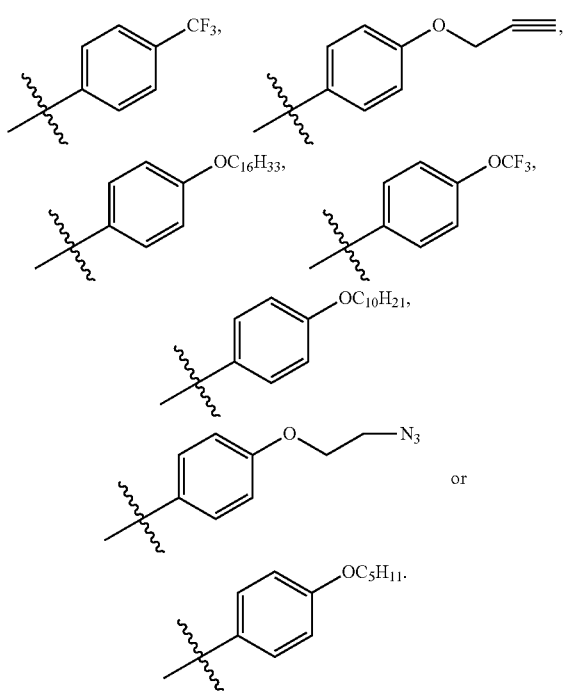

In the process described herein, the solvent system can be comprised of any suitable solvent including, but not limited to, water, acetonitrile, methanol (MeOH), isopropyl alcohol (iPrOH), tert-butanol (tBuOH), tert-amyl alcohol (tAmylOH) and dimethylacetamide (DMAc), or a combination thereof.

In certain embodiments, the solvent system of the processes described herein can be a combination of two or more solvents in optimal ratios. Suitable ratios for two solvent systems include, but are not limited to, 9:1, 4:1, 7:3, 3:2, 1:1, 2:3, 3:7; 1:4 and 1:9.

In certain embodiments, the solvent system is a combination of acetonitrile and water/salt buffer. A suitable ratio of acetonitrile and water/salt buffer can include, but is not limited to, 9:1, 8:2, 7:3, 6:4, 5:5, 4:6, 3:7; 2:8 and 1:9. In certain embodiments, the solvent system is a combination of acetonitrile and water/salt buffer in a ratio of 9:1.

In certain embodiments, the solvent system is acetonitrile.

In the processes described herein the solvent system is at a pH between 5-10. In certain embodiments the solvent system used in the processes described herein is at a pH between 6-10. In certain embodiments the solvent system used in the processes described herein is at a pH between 7-10. In certain embodiments the solvent system used in the processes described herein is at a pH between 8-10. In certain embodiments the solvent system used in the processes described herein is at a pH between 9-10. In certain embodiments the solvent system used in the processes described herein is at a pH between 6-9. In certain embodiments the solvent system used in the processes described herein is at a pH between 6-8. In certain embodiments the solvent system used in the processes described herein is at a pH between 6-7. In certain embodiments the solvent system used in the processes described herein is at a pH between 8-9.

In certain embodiments the solvent system used in the processes described herein is at a pH of 6. In certain embodiments the solvent system used in the processes described herein is at a pH of 7. In certain embodiments the solvent system used in the processes described herein is at a pH of 8. In certain embodiments the solvent system used in the processes described herein is at a pH of 9. In certain embodiments the solvent system used in the processes described herein is at a pH of 10.

In certain embodiments the solvent system used in the processes described herein is at a pH of 6.5. In certain embodiments the solvent system used in the processes described herein is at a pH of 7.5. In certain embodiments the solvent system used in the processes described herein is at a pH of 8.5. In certain embodiments the solvent system used in the processes described herein is at a pH of 9.5. In certain embodiments the solvent system used in the processes described herein is at a pH of 10.5.

The solvent system can be adjusted or kept at the desired pH by using pH buffers. Buffers can be added at the beginning of the reaction or during the reaction, as needed, to keep the pH of the system at the desired pH. Suitable buffers include, but are not limited to, sodium bicarbonate, sodium phosphate, sodium potassium phosphate, sodium acetate, or sodium bicarbonate/sodium carbonate ($Na_2CO_3$/$NaHCO_3$).

In certain embodiments of the processes described herein, once the reaction is complete, the mixture is concentrated by reducing the volume of the mixture and the pH lowered. The pH of the reaction mixture is lowered by adding in an acid or other proton donating compound. Suitable acids include, but are not limited to, trifluoroacetic acid (TFA), hydrochloric acid (HCl) or phosphoric acid.

In embodiments, the free amines in RHI can be protected prior to undergoing the chemistry described herein. Various protection methods are known in the art.

Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pme), methanesulfonamide (Ms), 0-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Methods of Treatment

The present invention provides a method for treating diabetes comprising administering to an individual with diabetes a therapeutically effective amount of a composition comprising a tyrosine functionalized insulin analog described herein. In particular aspects the diabetes is Type 1 diabetes, Type 2 diabetes, or gestational diabetes.

The present invention provides for the use of a composition for the treatment of diabetes comprising a tyrosine functionalized insulin analog described herein. In particular aspects the diabetes is Type 1 diabetes, Type 2 diabetes, or gestational diabetes.

The present invention provides for the use of a tyrosine functionalized insulin analog described herein for the manufacture of a medicament for the treatment of diabetes. In particular aspects the diabetes is Type 1 diabetes, Type 2 diabetes, or gestational diabetes.

The present invention provides a method for treating diabetes comprising forming an insulin dimer that was made using a tyrosine functionalized insulin analog described herein and administering to an individual with diabetes a therapeutically effective amount of a composition comprising the insulin dimer. In particular aspects the diabetes is Type 1 diabetes, Type 2 diabetes, or gestational diabetes.

The present invention provides for the use of a composition for the treatment of diabetes comprising an insulin dimer that was made using a tyrosine functionalized insulin analog described herein. In particular aspects the diabetes is Type 1 diabetes, Type 2 diabetes, or gestational diabetes.

The present invention provides for the use of an insulin dimer that was made using a tyrosine functionalized insulin analog described herein for the manufacture of a medicament for the treatment of diabetes. In particular aspects the diabetes is Type 1 diabetes, Type 2 diabetes, or gestational diabetes.

Tyrosine Functionalized Insulin Analogs Made in Accordance with the Processes Described Herein Also described herein are the following compounds made using the processes described herein.

The present invention also provides tyrosine functionalized insulin analogs selected from:

COMPOUND 1
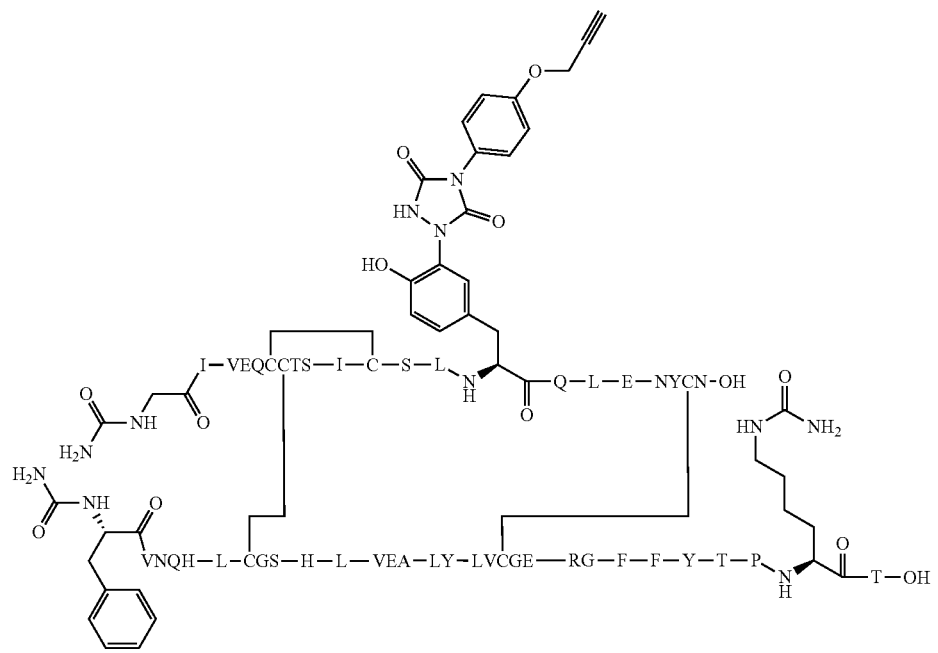
(SEQ ID NOS 18 and 19, respectively)
COMPOUND 2
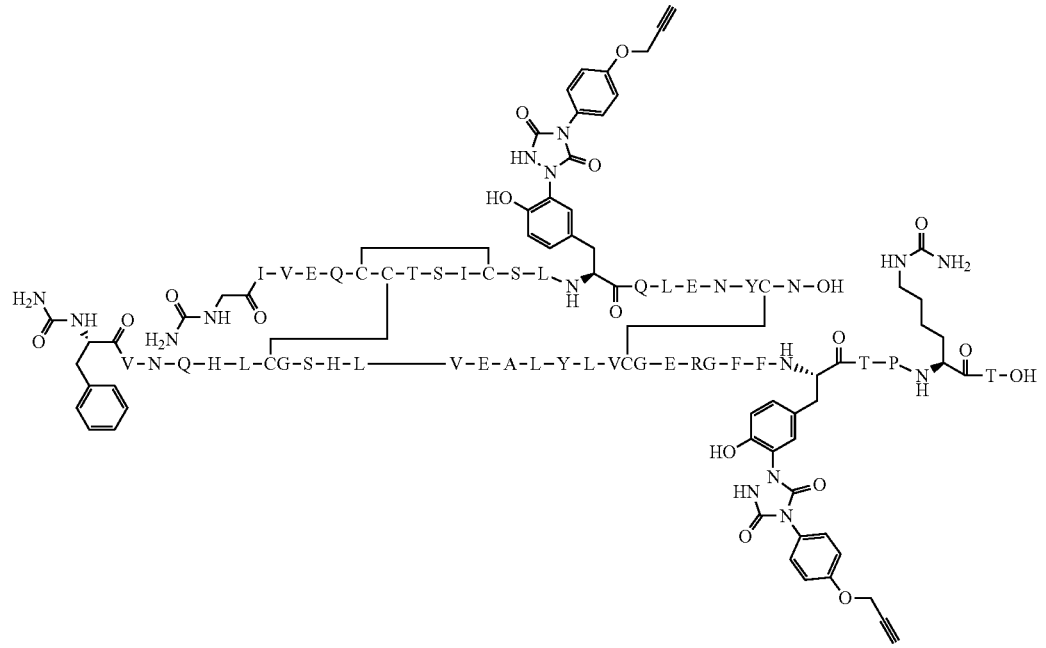
(SEQ ID NOS 18 and 20, respectively)

COMPOUND 3
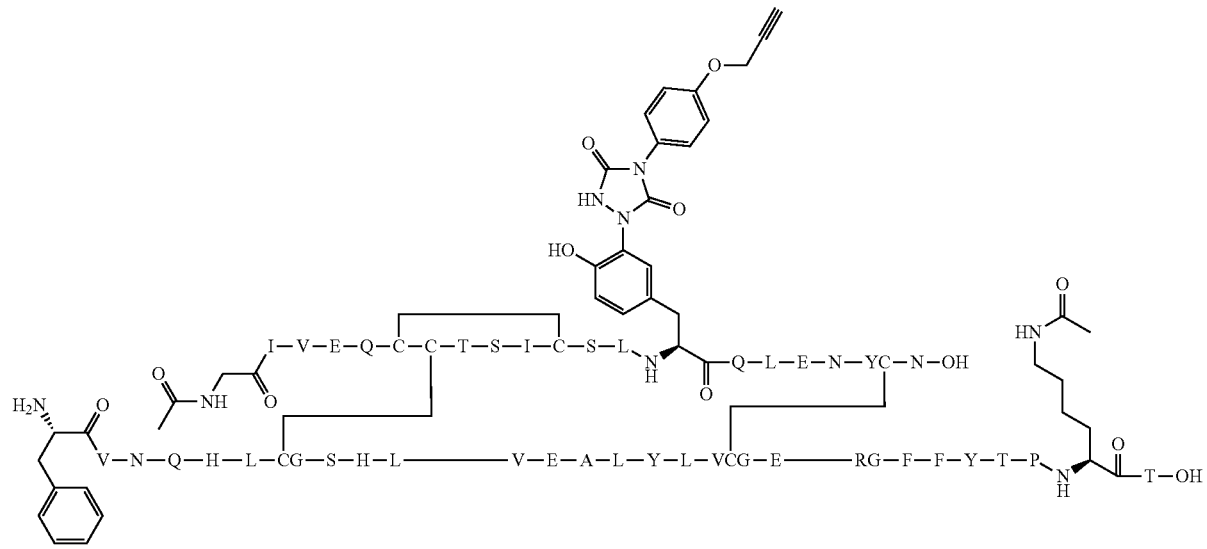
(SEQ ID NOS 21 and 22, respectively)
COMPOUND 4
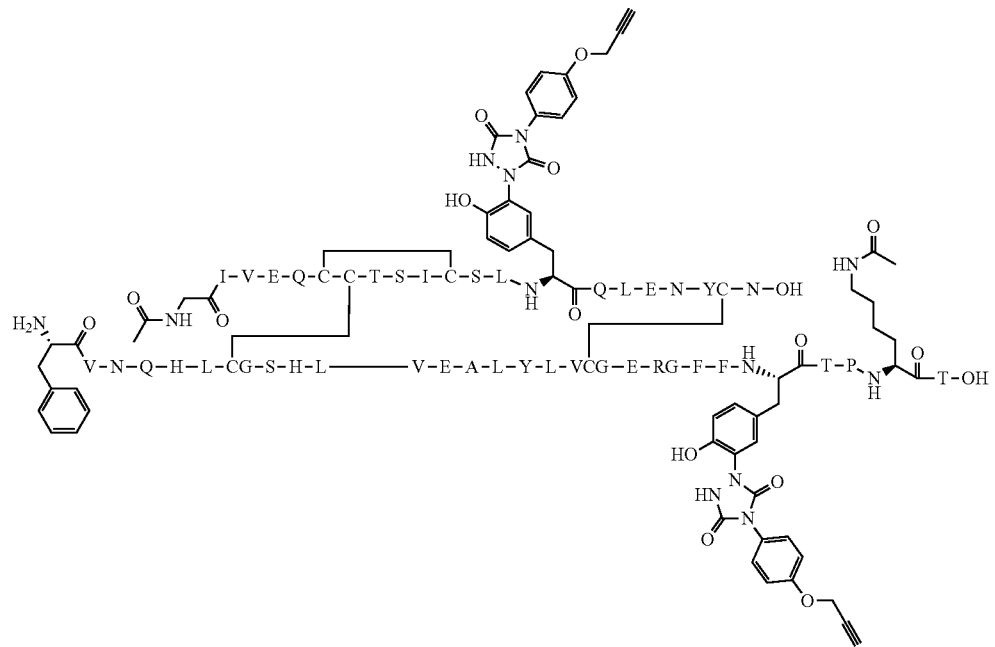
(SEQ ID NOS 21 and 23, respectively)

COMPOUND 5
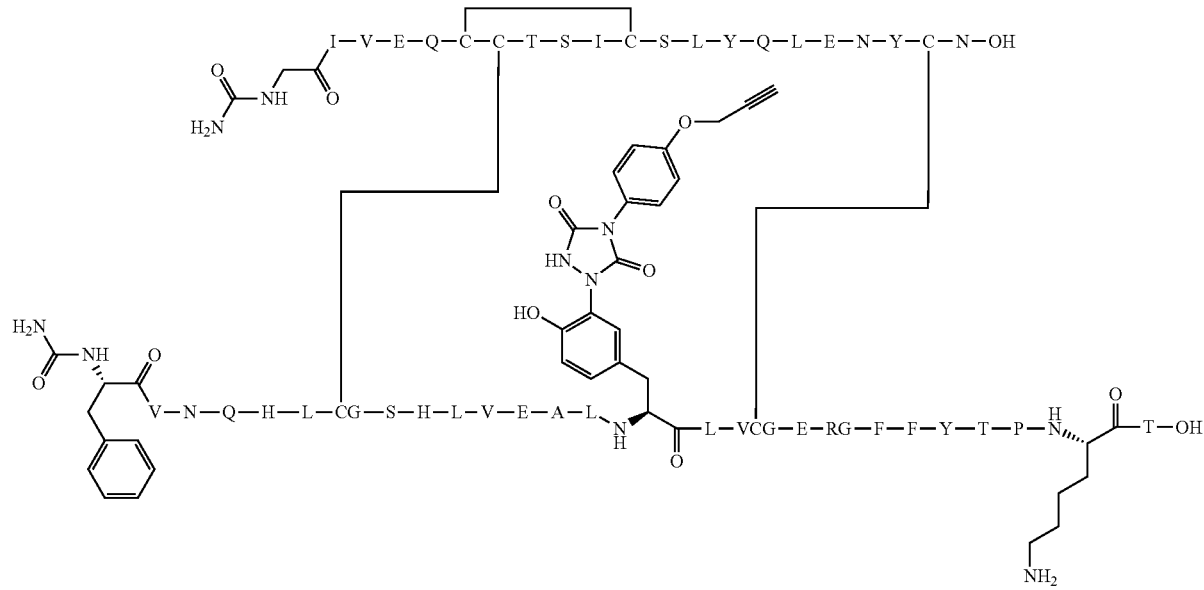
(SEQ ID NOS 24 and 25, respectively)
COMPOUND 6
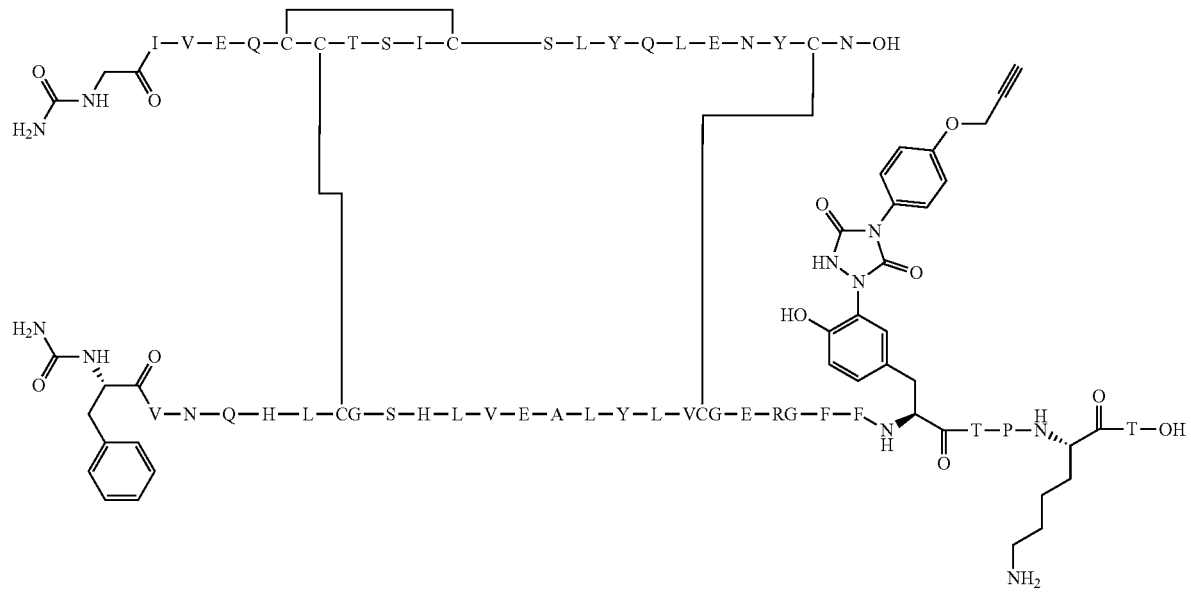
(SEQ ID NOS 24 and 26, respectively)

COMPOUND 7
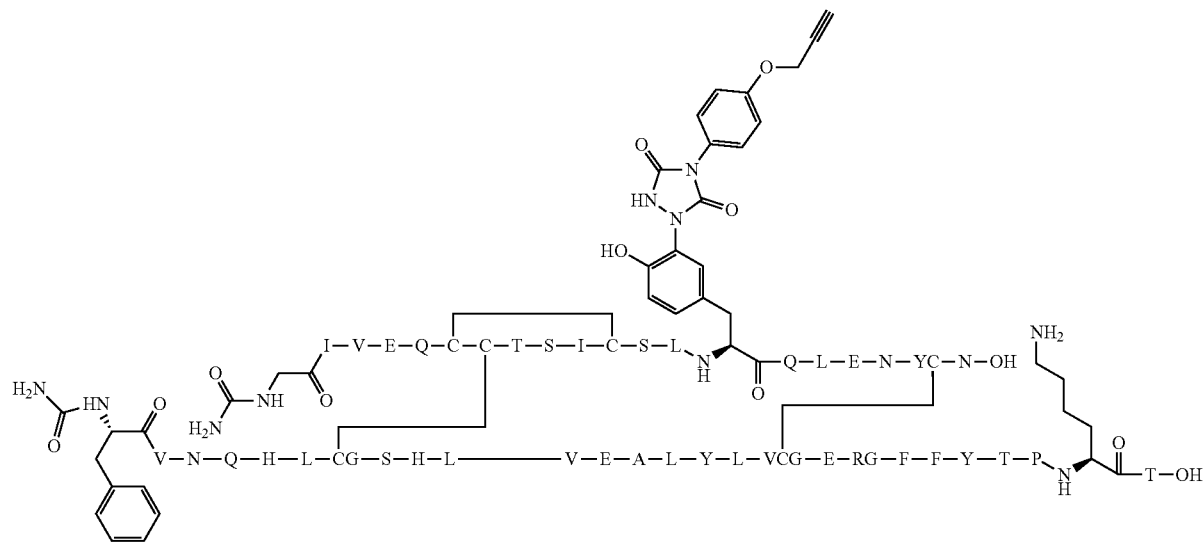
(SEQ ID NOS 18 and 27, respectively)
COMPOUND 8
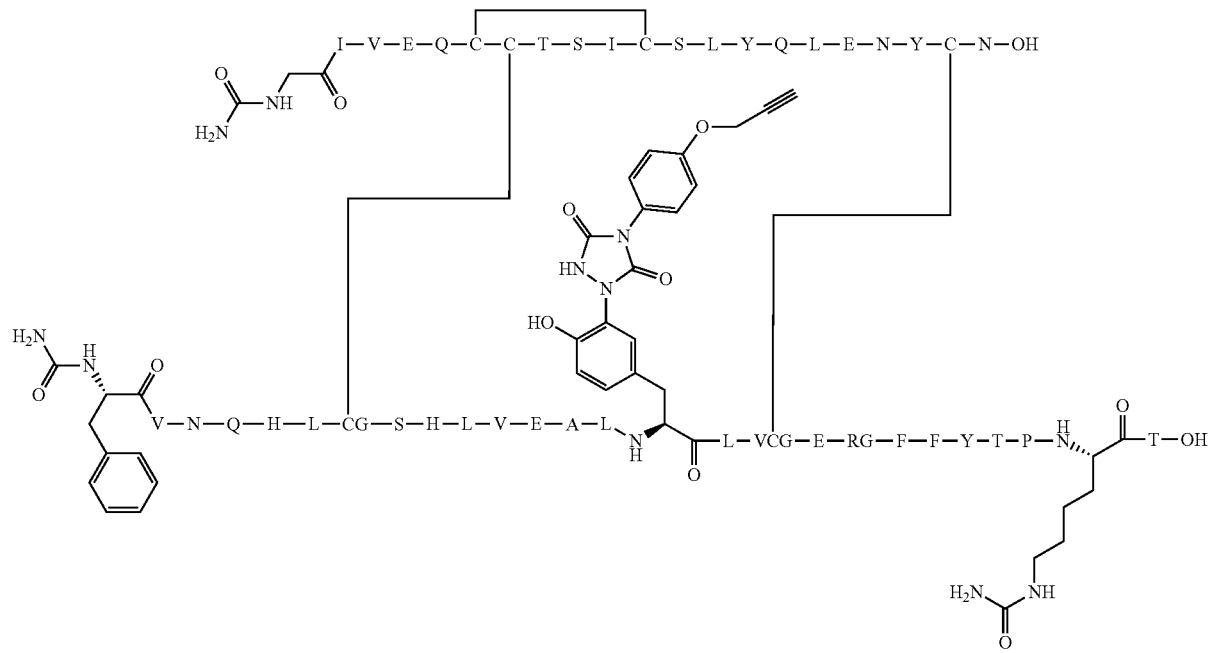
(SEQ ID NOS 24 and 28, respectively)

COMPOUND 9
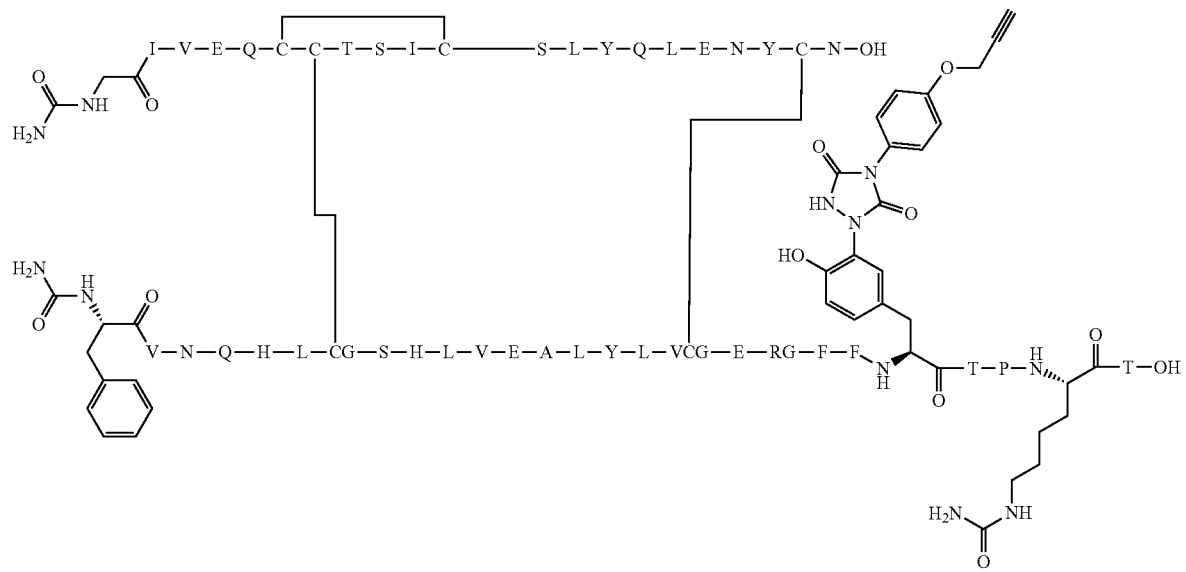
(SEQ ID NOS 24 and 20, respectively)
COMPOUND 10
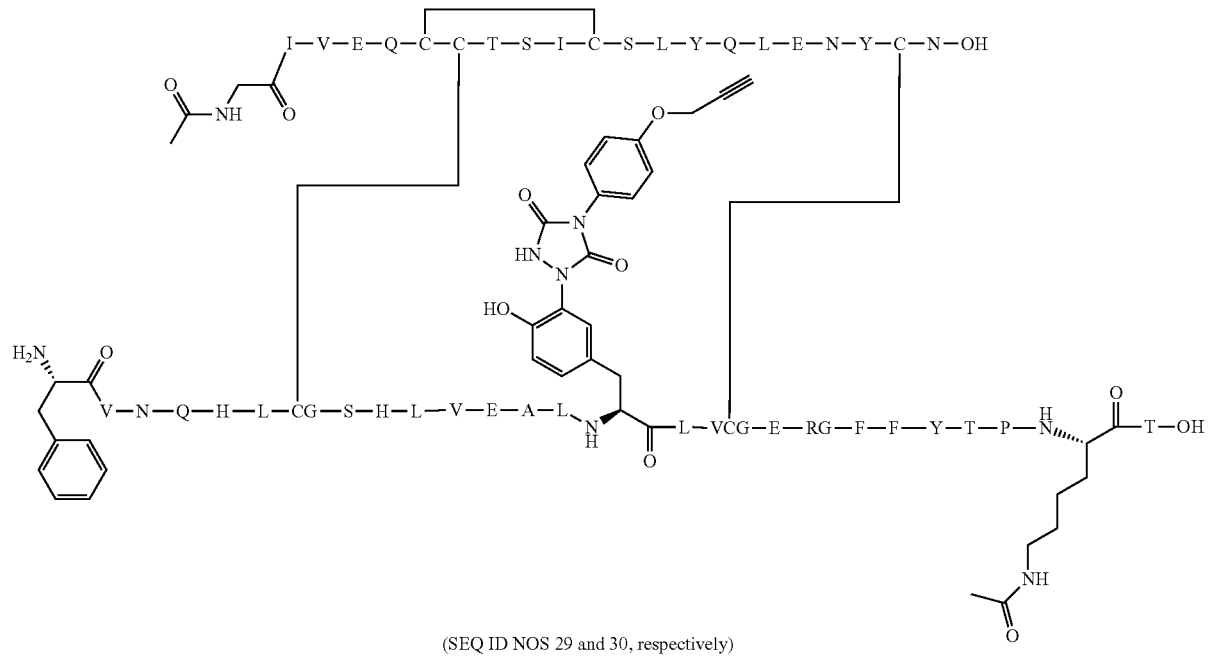
(SEQ ID NOS 29 and 30, respectively)

COMPUND 11
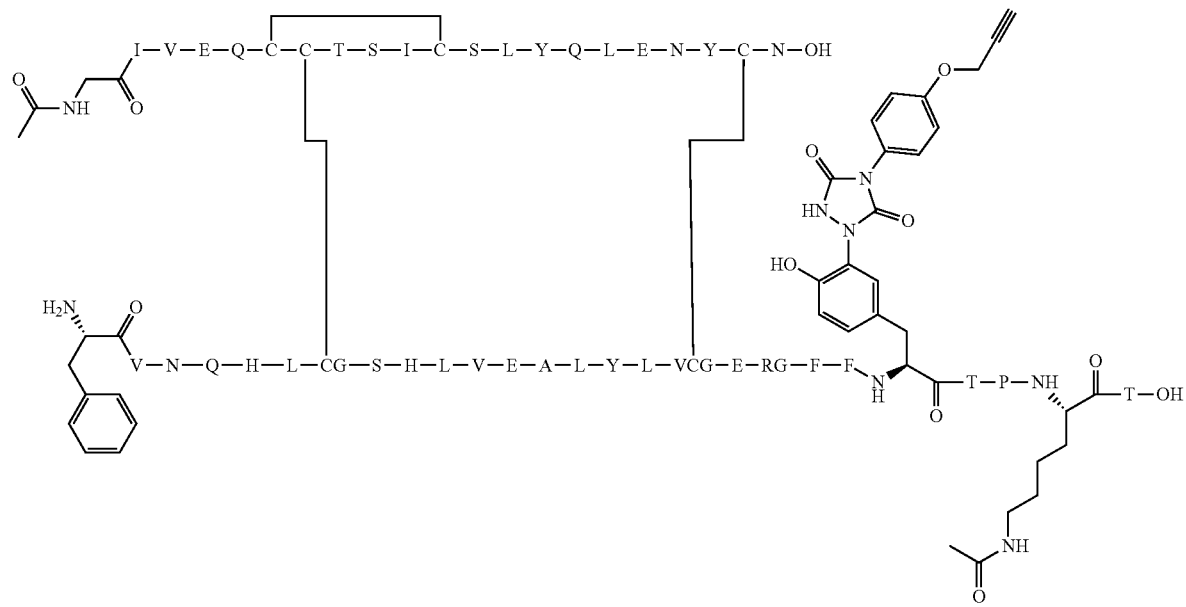
(SEQ ID NOS 29 and 23, respectively)
COMPOUND 12
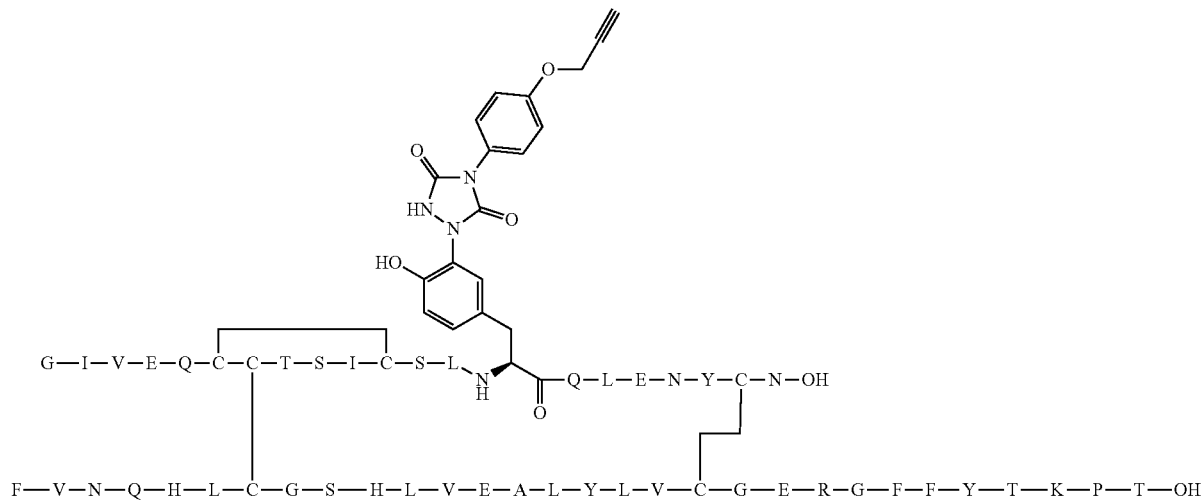
(SEQ ID NOS 31 and 4, respectively)

COMPOUND 13
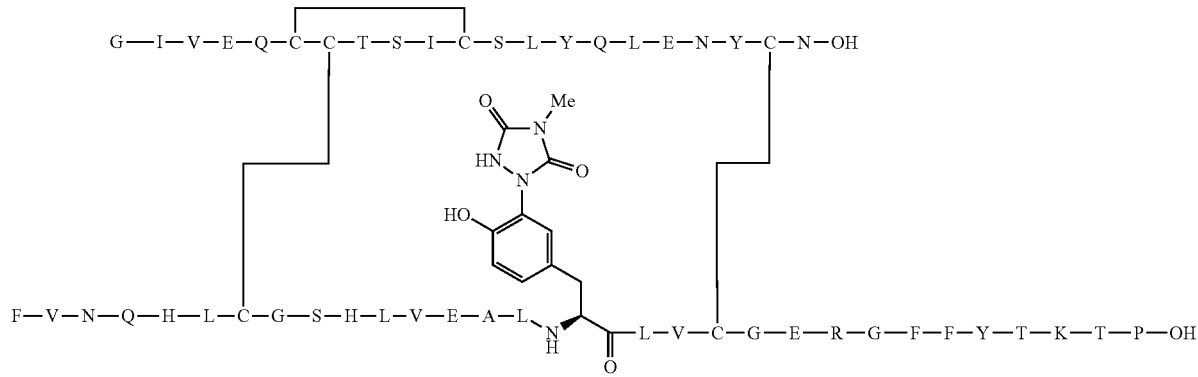
(SEQ ID NOS 1 and 32, respectively)
COMPOUND 14
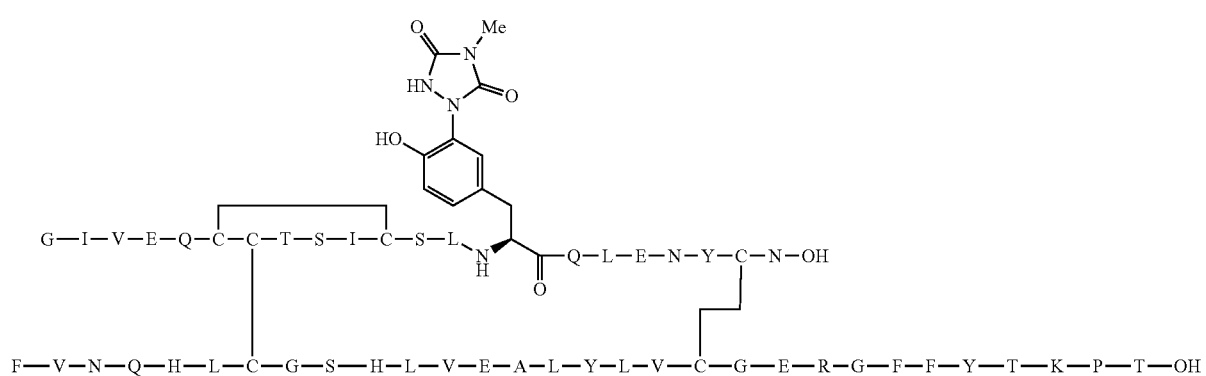
(SEQ ID NOS 33 and 4, respectively)
COMPOUND 15
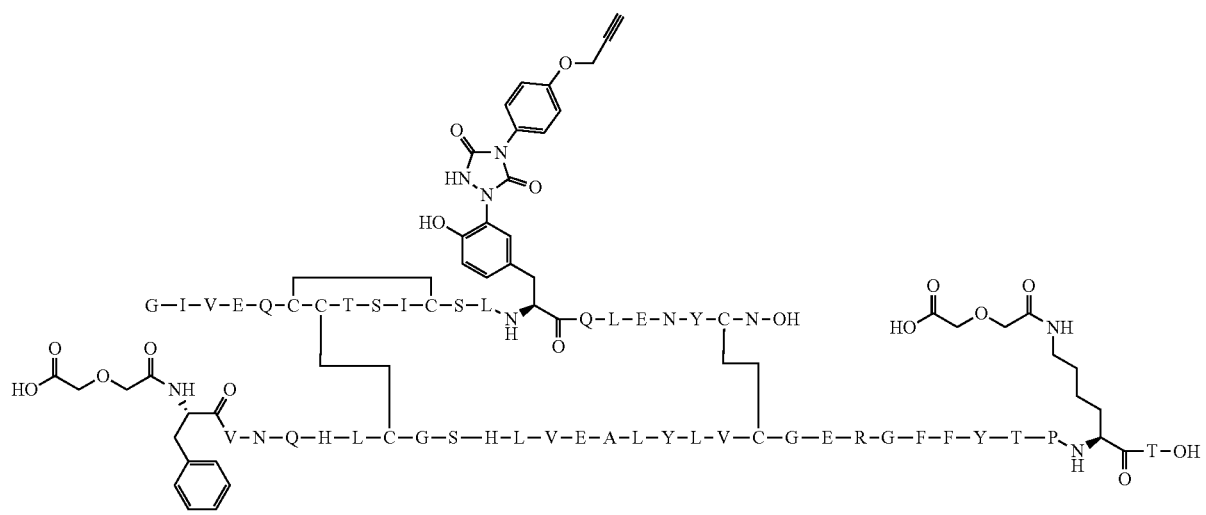
(SEQ ID NOS 31 and 34, respectively)

COMPOUND 16
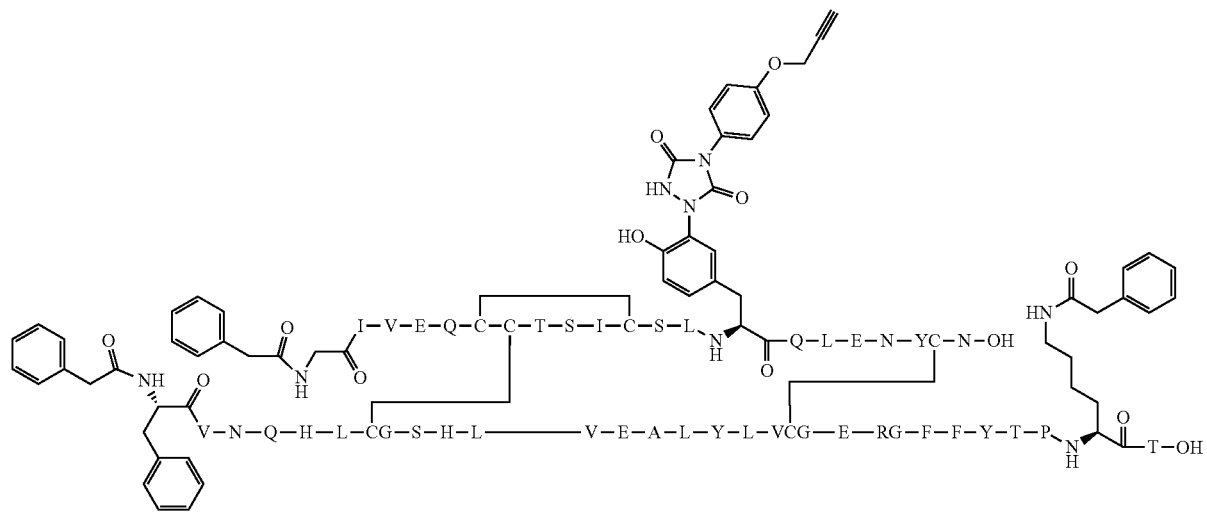
(SEQ ID NOS 35 and 36, respectively)
COMPOUND 17
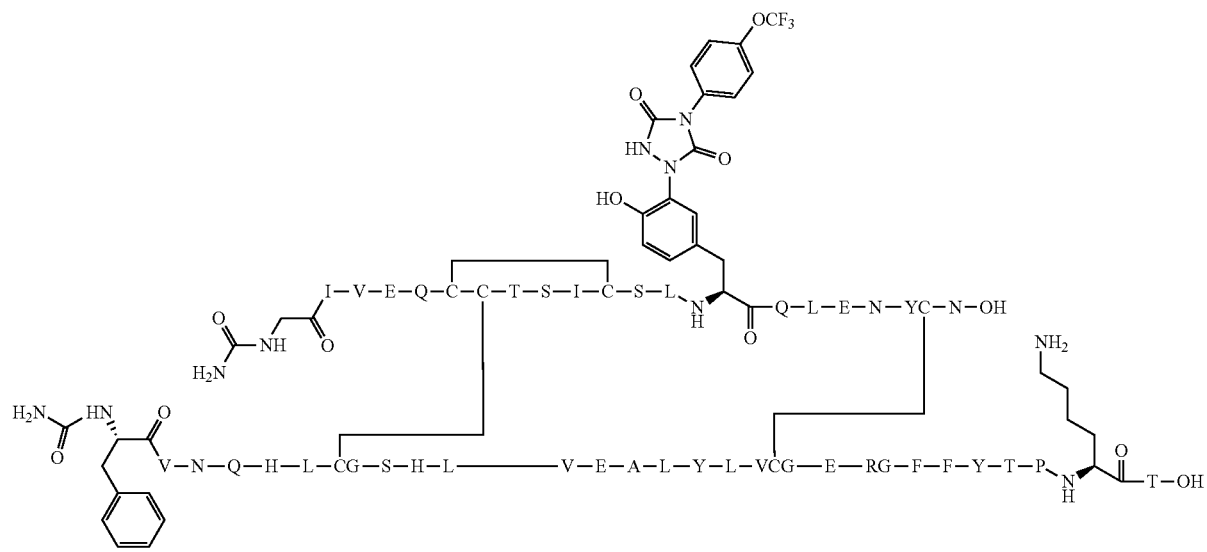
(SEQ ID NOS 37 and 27, respectively)

COMPOUND 18
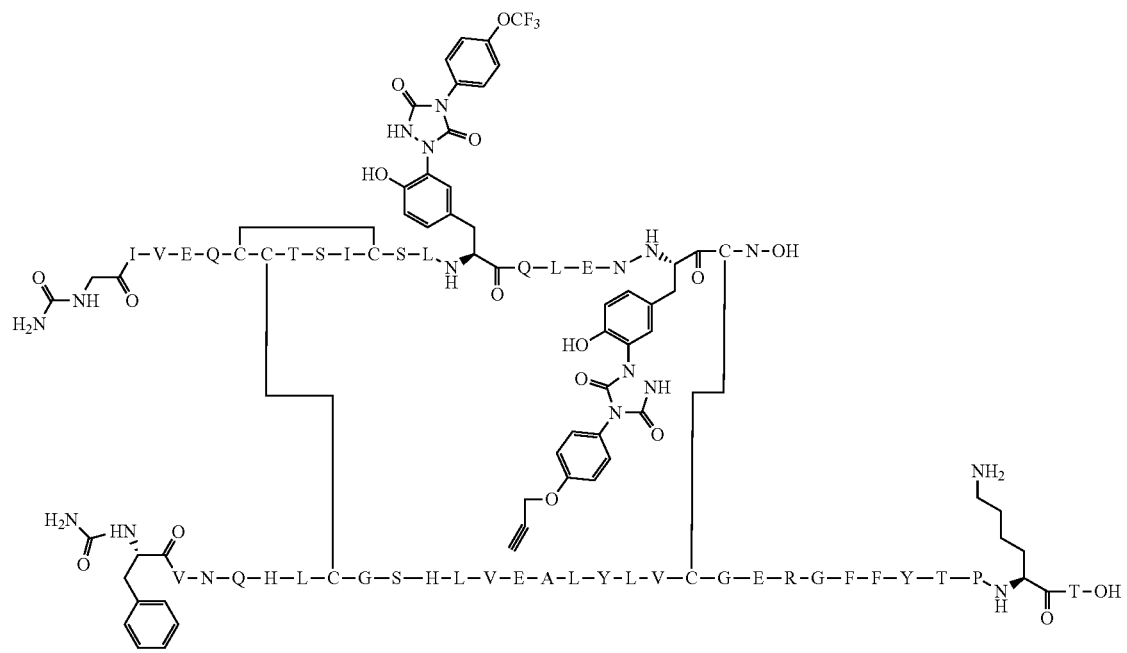
(SEQ ID NOS 38 and 27, respectively)
COMPOUND 19
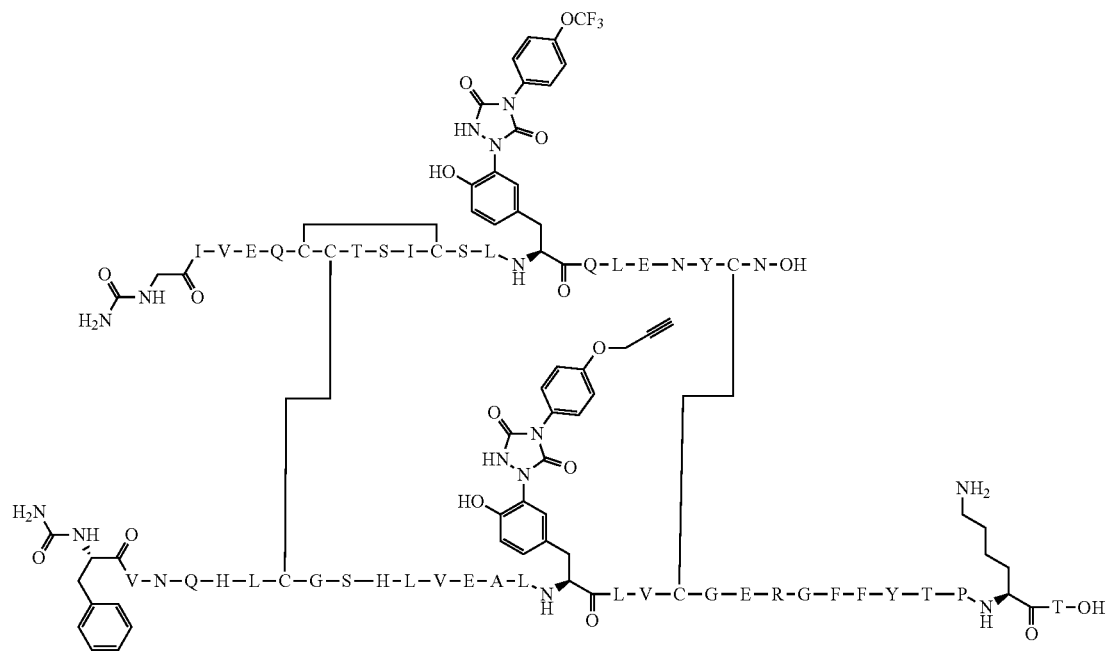
(SEQ ID NOS 37 and 25, respectively)

COMPOUND 20
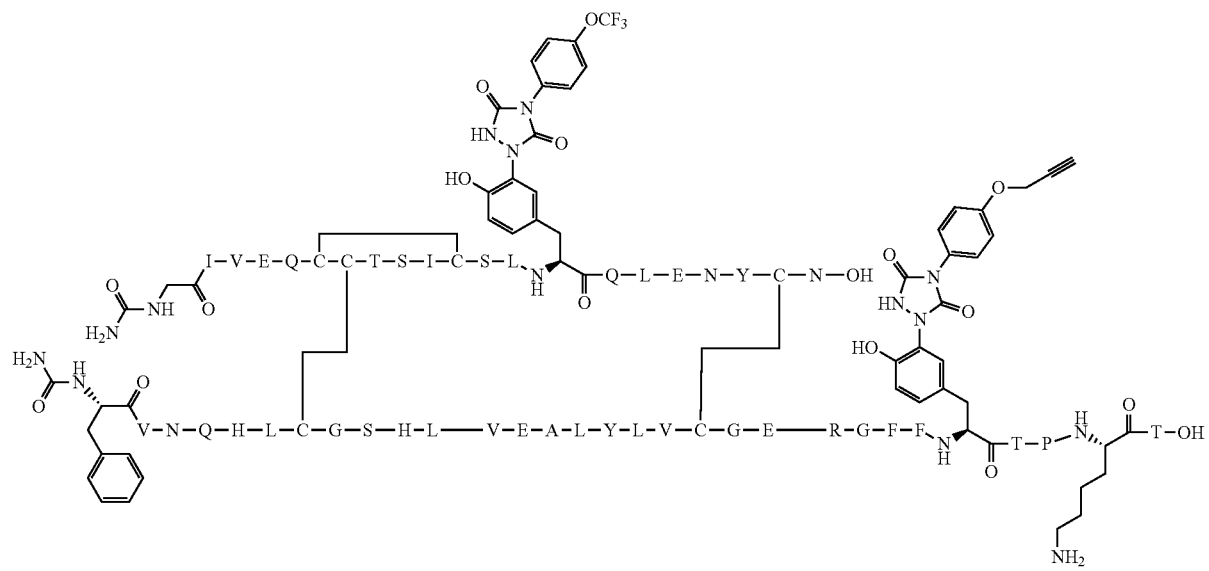
(SEQ ID NOS 37 and 26, respectively)
COMPOUND 21
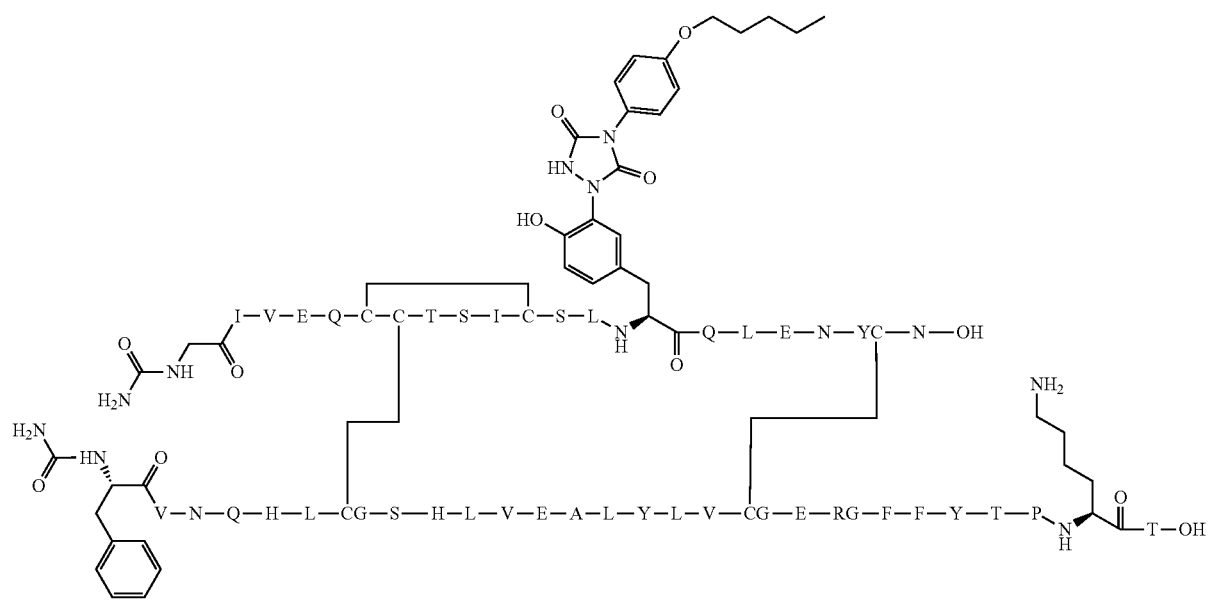
(SEQ ID NOS 39 and 27, respectively)

COMPOUND 22
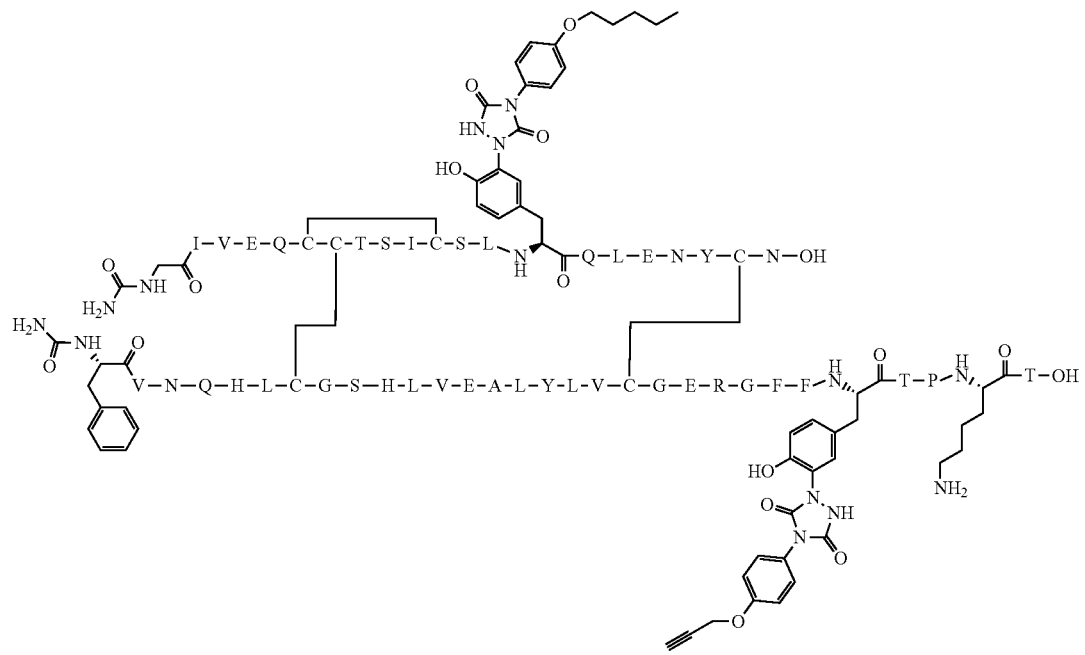
(SEQ ID NOS 39 and 26, respectively)
COMPOUND 23
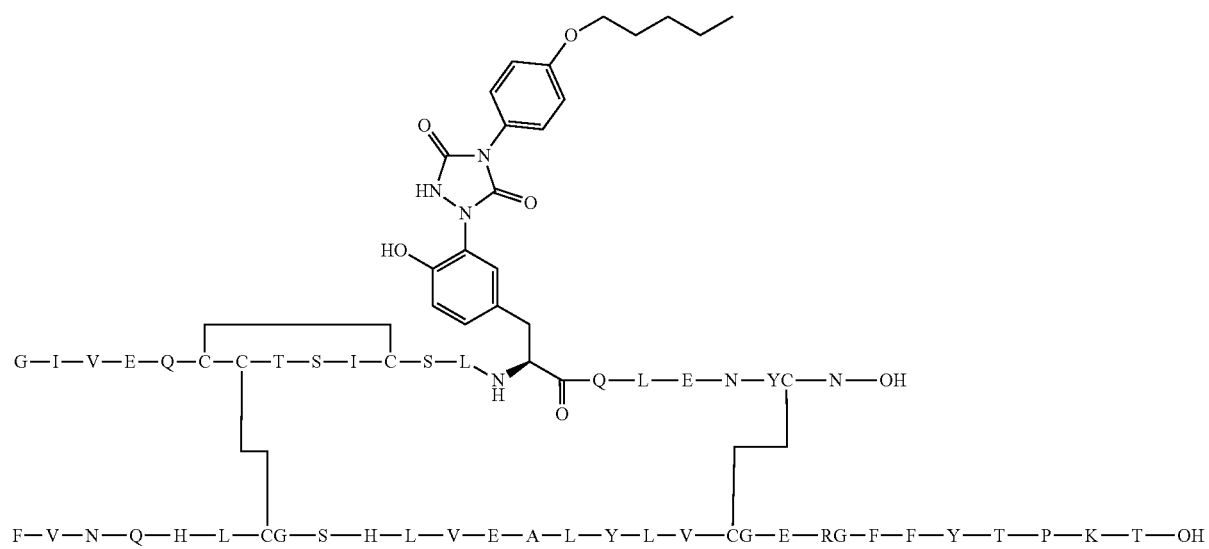
(SEQ ID NOS 40 and 2, respectively)

COMPOUND 24

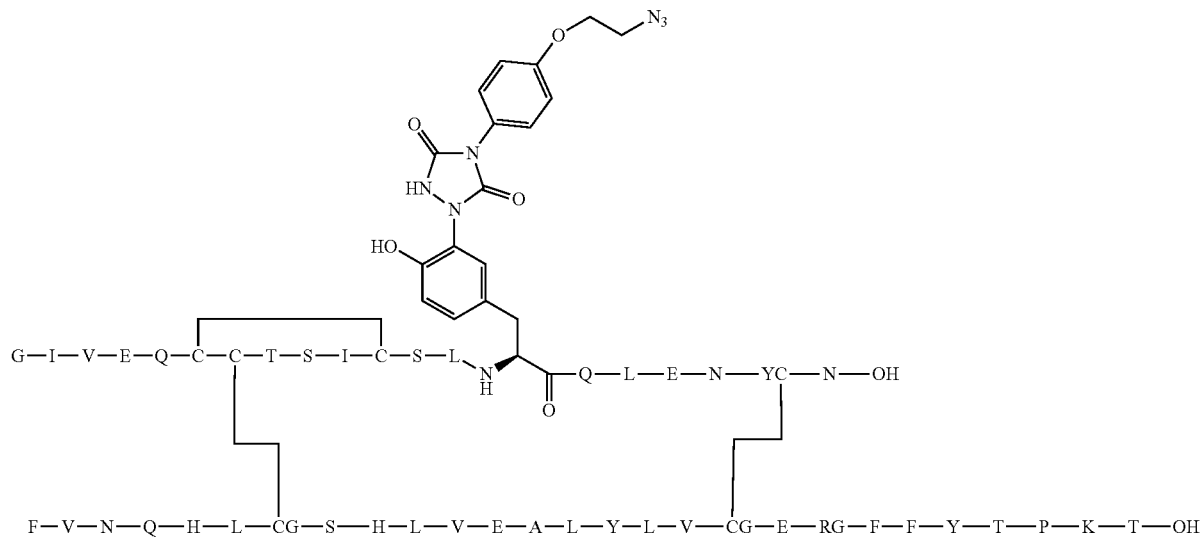

(SEQ ID NOS 41 and 2, respectively)

COMPOUND 25

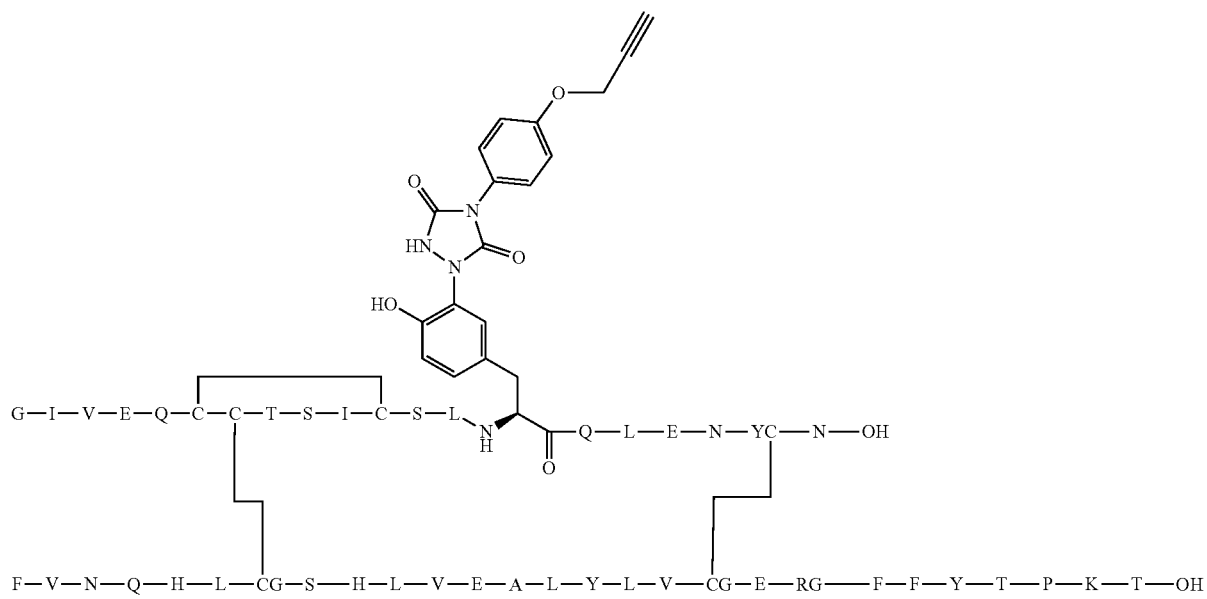

(SEQ ID NOS 31 and 2, respectively)

Pharmaceutical Compositions

In accordance with one embodiment a pharmaceutical composition is provided comprising any of the tyrosine functionalized insulin analogs described herein, preferably at a purity level of at least 90%, 91%, 92%, 93%, 94%, 95%, 96%, 97%, 98% or 99%, and a pharmaceutically acceptable diluent, carrier or excipient. Such compositions may contain a tyrosine functionalized insulin analog described herein or insulin analog dimers that were made using a tyrosine functionalized insulin analog described herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

The disclosed tyrosine functionalized insulin analogs described herein or insulin analog dimers that were made using a tyrosine functionalized insulin analog described herein are believed to be suitable for any use that has previously been described for insulin peptides. Accordingly, the tyrosine insulin analogs described herein or insulin analog dimers that were made using a tyrosine functionalized insulin analog disclosed herein can be used to treat hyperglycemia, or treat other metabolic diseases that result from high blood glucose levels. Accordingly, the present invention encompasses pharmaceutical compositions comprising a tyrosine functionalized insulin analog described herein or insulin analog dimers that were made using a tyrosine functionalized insulin analog as disclosed herein and a pharmaceutically acceptable carrier for use in treating a patient suffering from high blood glucose levels. In accordance with one embodiment the patient to be treated using a tyrosine functionalized insulin analog described herein or insulin analog dimers that were made using a tyrosine functionalized insulin analog disclosed herein is a domesticated animal, and in another embodiment the patient to be treated is a human.

One method of treating hyperglycemia in accordance with the present disclosure comprises the steps of administering the presently disclosed tyrosine functionalized insulin analogs described herein or insulin analog dimers that were made using a tyrosine functionalized insulin analog described herein to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the tyrosine functionalized insulin analogs described herein or insulin analog dimers that were made using a tyrosine functionalized insulin analog described herein, or prodrug derivative thereof, is prepackaged in a syringe.

The tyrosine functionalized insulin analogs described herein or insulin analog dimers that were made using a tyrosine functionalized insulin analog described herein may be administered alone or in combination with other anti-diabetic agents. Anti-diabetic agents known in the art or under investigation include native insulin, native glucagon and functional analogs thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as sitagliptin, vildagliptin, saxagliptin, linagliptin, gemigliptin, anagliptin, teneligliptin, alogliptin, trelagliptin, omarigliptin, evogliptin, gosogliptin and dutogliptin; SGLT2 (sodium-dependent glucose transporter) inhibitors such as dapagliflozin, empagliflozin, canagliflozin, ipragliflozin, tofogliflozin, sergliflozin, remogliflozin, ertugliflozin and sotagliflozin; or FBPase (fructose 1,6-bisphosphatase) inhibitors.

Pharmaceutical compositions comprising the tyrosine functionalized insulin analogs or insulin analog dimers that were made using a tyrosine functionalized insulin analog described herein can be formulated and administered to patients using standard pharmaceutically acceptable carriers and routes of administration known to those skilled in the art. Accordingly, the present disclosure also encompasses pharmaceutical compositions comprising one or more of the tyrosine functionalized insulin analogs or insulin analog dimers that were made using a tyrosine functionalized insulin analog described herein, or a pharmaceutically acceptable salt thereof, in combination with a pharmaceutically acceptable carrier. For example, the pharmaceutical compositions comprising the tyrosine functionalized insulin analogs described herein or insulin analog dimers that were made using a tyrosine functionalized insulin analog described herein may optionally contain zinc ions, preservatives (e.g., phenol, cresol, parabens), isotonicizing agents (e.g., mannitol, sorbitol, lactose, dextrose, trehalose, sodium chloride, glycerol), buffer substances, salts, acids and alkalis and also further excipients. These substances can in each case be present individually or alternatively as mixtures. Glycerol, dextrose, lactose, sorbitol and mannitol are customarily present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e., 2-amino-2-hydroxymethyl-1,3-propanediol) buffer and corresponding salts, are present in a concentration of 5-250 mM, commonly from about 10-100 mM. Further excipients can be, inter alia, salts or arginine.

In one embodiment the pharmaceutical composition comprises a 1 mg/mL concentration of the tyrosine functionalized insulin analogs described herein or insulin analog dimers that were made using a tyrosine functionalized insulin analog described herein at a pH of about 4.0 to about 7.0 in a phosphate buffer system. The pharmaceutical compositions may comprise the tyrosine insulin analogs or insulin analog dimers that were made using a tyrosine functionalized insulin analog described herein as the sole pharmaceutically active component, or the tyrosine functionalized insulin analogs described herein or insulin analog dimers that were made using a tyrosine functionalized insulin analog described herein can be combined with one or more additional active agents.

All therapeutic methods, pharmaceutical compositions, kits and other similar embodiments described herein contemplate that tyrosine functionalized insulin analogs described herein or insulin analog dimers that were made using a tyrosine functionalized insulin analog described herein include all pharmaceutically acceptable salts thereof.

In one embodiment the kit is provided with a device for administering the tyrosine functionalized insulin analogs described herein or insulin analog dimers that were made using a tyrosine functionalized insulin analog composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the tyrosine functionalized insulin analogs described herein or insulin analog dimers that were made using a tyrosine functionalized inculin analog composition is prepackaged within the syringe.

The following examples are intended to promote a further understanding of the present invention.

EXAMPLES

General Procedures

All chemicals were purchased from commercial sources, unless otherwise noted. Reactions were usually carried out at ambient temperature or at room temperature unless otherwise noted. Reactions sensitive to moisture or air were performed under nitrogen using anhydrous solvents and reagents. The progress of reactions was monitored by ultra-performance liquid chromatography-mass spectrometry (UPLC-MS). Ultra-performance liquid chromatography (UPLC) was performed on a Waters Acquity™ UPLC® system.
Analytical method A Waters Acquity™ UPLC® BEH C8, 1.7 μm particle size, 2.1×100 mm column with gradient 10:90-55:45 v/v $CH_3CN/H_2O$+v 0.05% TFA over 4.0 min and 55:45-95:5 v/v $CH_3CN/H_2O$+v 0.05% TFA over 40 sec; flow rate 0.3 mL/min, UV wavelength 200-300 nm;
Analytical method B Waters Acquity™ UPLC® BEH C8 1.7 μm particle size, 2.1×100 mm column with gradient 20:80-90:10 v/v $CH_3CN/H_2O$+v 0.1% TFA over 4.0 min and 90:10-95:5 v/v $CH_3CN/H_2O$+v 0.1% TFA over 0.4 min; flow rate 0.3 mL/min, UV wavelength 200-300 nm.
Analytical method C Waters Acuity™ UPLC®, HSS C18, 1.8 μm particle size, 2.1×50 mm column length, with gradient 10-100% v/v $CH_3CN/H_2O$+v 0.1% TFA over 5 min, flow rate 1 mL/min. UV wavelength 200-300 nm.
Analytical method D Waters Acuity™ UPLC®, XSelect CSH C18, 2.5 μm particle size, 2.1×50 mm column length, with gradient 5-50% v/v $CH_3CN/H_2O$+v 0.1% TFA over 15 min, flow rate 1 ml/min. UV wavelength 200-300 nm.

Mass analysis was performed on a Waters SQ Detector with electrospray ionization in positive ion detection mode and the scan range of the mass-to-charge ratio was 300-2000. The identification of the produced insulin analogs was confirmed by comparing the theoretical molecular weight to the experimental value that was measured using UPLC-MS, generally finding the [(M+4)/4] mass. For the determination of the linkage positions, compounds were subjected to DTT (dithiothreitol) treatment (for A/B chain) and/or Glu-C digestion (with or without reduction and alkylation) and/or Chymotrypsin digestion, and then the resulting peptides were analyzed by LC-MS. Based on the measured masses, the linkage positions were deduced.

Preparative scale HPLC was performed on Waters Acuity system with conditions as noted. Concentration of solutions was carried out on a rotary evaporator under reduced pressure or freeze-dried on a VirTis Freezemobile 25EL Sentry 2.0 Freeze Dryer (SP Scientific), aLabconco Freezone 2.5Plus Freeze Dryer or a Virtis Genesis 25EL Pilot Freeze Dryer (SP Scientific).

Abbreviations: acetonitrile (ACN), aqueous (aq), dichloromethane (DCM), diisopropylethylamine (DIPEA), isopropyl acetate (IPAc), methyl t-butyl ether (MTBE), trifluoroacetic acid (TFA), mass spectrum (ms or MS), microgram(s) (μg), microliter(s) (μL), micromole (μmol), milligram(s) (mg), milliliter(s) (mL), millimole (mmol), minute(s) (min), phenyl (Ph), phenyl-3H-1,2,4-triazoline-3,5-(4H)dione (PTAD), dimethyl sulfoxide ((DMSO) retention time ($R_t$), room temperature (rt), and trifluoroacetic acid (TFA).

The term "RHI" refers to recombinant human insulin and is used to indicate that the insulin has the amino acid sequence characteristic of native, wild-type human insulin. As used herein in the tables, the term indicates that the amino acid sequence of the insulin is that of native, wild-type human insulin.

Scheme 1
(Scheme 1 discloses SEQ ID NOS 42-45, respectively, in order of appearance)

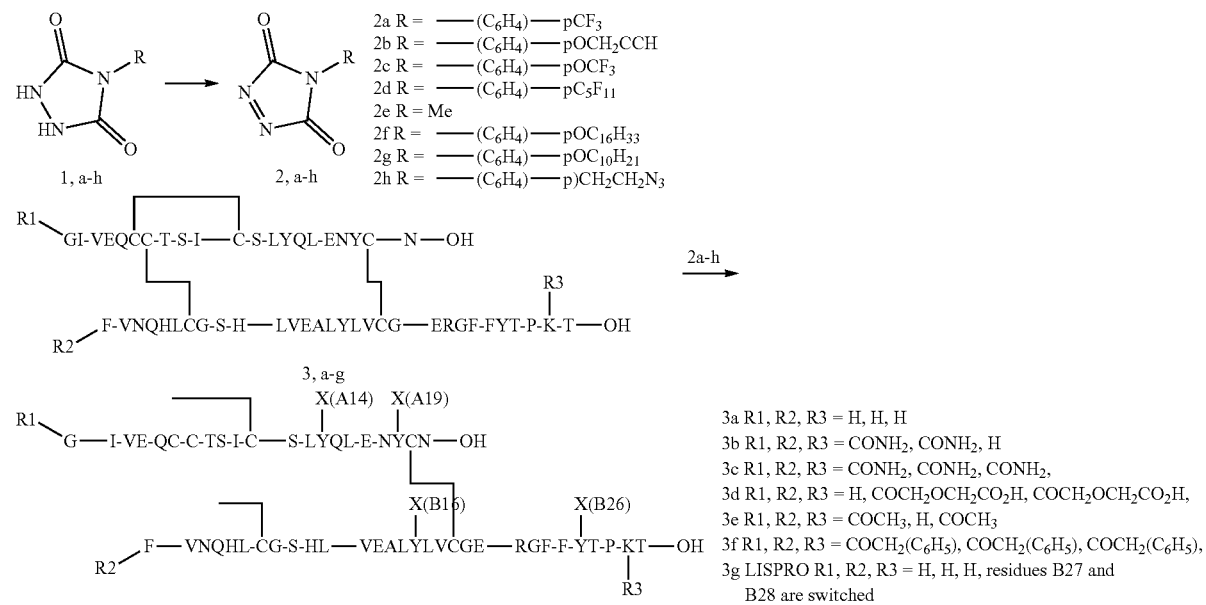

LISPRO reference:
A. Pfutzner, E. Kustner, T. Forst, Intensive insulin therapy with insulin lispro in patients with type 1 diabetes reduces the frequency of hypoglycemic episodes, Exp. Clin. Endocrinol. Diabetes 104 (1996) 25-30.

General Procedure for the Preparation of Activated PTAD Reagents

Nitric acid (1.00 ml, 70%) was added to a 20 mL vial containing silica gel (1.0 g, 230-400 mesh). The contents were mixed with a spatula and let sit for at least 10 min. The acid absorbed into the silica gel resulting in a slightly moist solid.

The activated HNO$_3$-silica gel (100-250 mg) was added to a solution of 4R-1,2,4-triazolidine-3,5-dione (100 mg) in anhydrous DCM (5 ml) at room temperature and the resulting reaction was mixed for 30-90 min until the reaction was complete, yielding a clear and highly colored solution. The reaction was then filtered through a frit removing the silica gel. The silica gel was washed with DCM and the filtrate collected and dried by rotovap to a highly colored solid.

Example 1

PTAD 2a

Synthesis of 4-(4-(trifluoromethyl)phenyl)-3H-1,2,4-triazole-3,5(4H)-dione

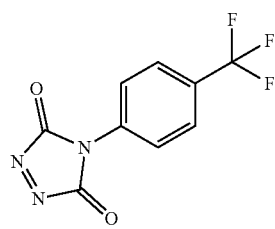 [SMILES: O=C1N=NC(=O)N1c1ccc(C(F)(F)F)cc1]

Using the appropriate starting material, the general procedure was followed to obtain a red solid. NMR indicates loss of amine protons. HNMR CDCl$_3$, 2H (d, 7.73 m 7.75), 2H (d,7.86, 7.88)

Example 2

PTAD 2b

Synthesis of 4-(4-(prop-2-yn-1-yloxy)phenyl)-3H-1,2,4-triazole-3,5(4H)-dione

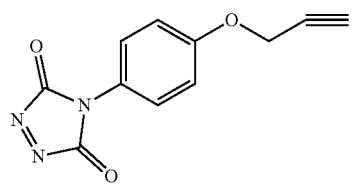 [SMILES: C#CCOc1ccc(N2C(=O)N=NC2=O)cc1]

Using the appropriate starting material, the general procedure was followed to obtain a red solid. HNMR CD$_3$CN 2H (d, 7.40, 7.38), 2H (d,7.21, 7.19), 2H (s, 4.84), 1H (s, 2.88)

Example 3

PTAD 2c

Synthesis of 4-(4-(trifluoromethoxy)phenyl)-3H-1,2,4-triazole-3,5(4H)-dione

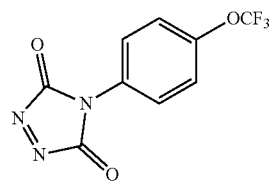 [SMILES: O=C1N=NC(=O)N1c1ccc(OC(F)(F)F)cc1]

Using the appropriate starting material, the general procedure was followed to obtain a red solid. HNMR CD$_3$CN 2H (d, 7.54, 7.55), 2H (d, 7.58, 7.60), FNMR CD$_3$CN 3F (s, -58.9)

Example 4

PTAD 2d

Synthesis of 4-(4-(pentyloxy)phenyl)-3H-1,2,4-triazole-3,5(4H)-dione

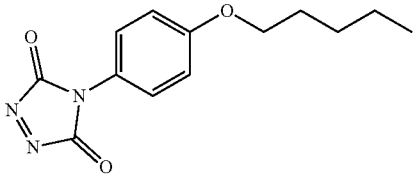 [SMILES: CCCCCOc1ccc(N2C(=O)N=NC2=O)cc1]

Using the appropriate starting material, the general procedure was followed to obtain a red, slightly sticky solid. Further drying was carried out under vacuum. HNMR CD$_3$CN 2H (d, 7.32, 7.34), 2H (d, 7.10, 7.12), 2H (t, 4.08, 4.07, 4.05), 2H (m, 1.81), 4H (m, 1.46), 3H (t, 0.97, 0.96, 0.95)

Example 5

PTAD 2e

Synthesis of 4-methyl-3H-1,2,4-triazole-3,5(4H)-dione

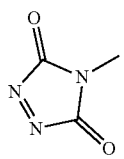

Using the appropriate starting material, the general procedure was followed to obtain a pink solid. HNMR CD$_3$CN, 3H (s, 3.11)

Example 6

PTAD 2f

Synthesis of 4-(4-(hexadecyloxy)phenyl)-1,2,4-tri-
azolidine-3,5-dione

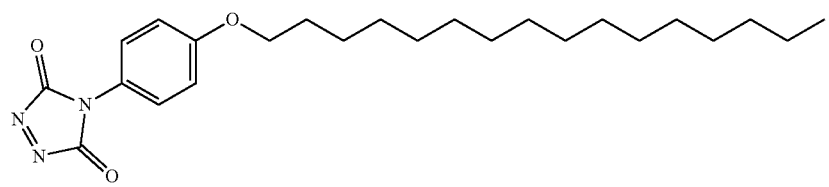 [SMILES: CCCCCCCCCCCCCCCCOc1ccc(N2C(=O)N=NC2=O)cc1]

Using the appropriate starting material, the general procedure was followed to obtain a red-orange solid. HNMR d-acetone 2H (7.42), 2H (7.14), 2H (4.09), 2H (m, 1.81), 2H (m, 1.51), 24H (m, 1.31), 3H (t, 0.90)

Example 7

PTAD 2g

Synthesis of 4-(4-(decyloxy)phenyl)-1,2,4-triazoli-
dine-3,5-dione

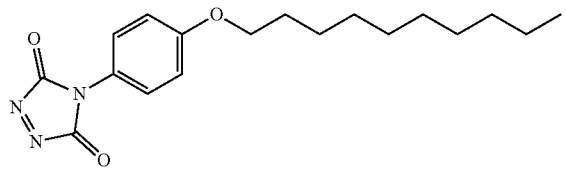 [SMILES: CCCCCCCCCCOc1ccc(N2C(=O)N=NC2=O)cc1]

Using the appropriate starting material, the general procedure was followed to obtain a red solid. HNMR d-acetone 2H (d, 7.42, 7.40), 2H (d, 7.14, 7.13), 2H (t, 4.10, 4.09, 4.08), 2H (m, 1.82), 2H (m, 1.51), 12H (m, 1.32), 3H (t, 0.91, 0.90, 0.88)

Example 8

PTAD 2h

Synthesis of 4-(4-(2-azidoethoxy)phenyl)-3H-1,2,4-
triazole-3,5(4H)-dione

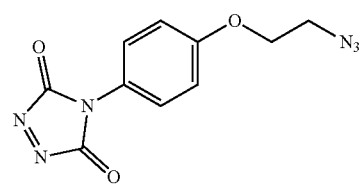 [SMILES: [N-]=[N+]=NCCOc1ccc(N2C(=O)N=NC2=O)cc1]

Using the appropriate starting material, the general procedure was followed to obtain a red solid.

PTAD analogs

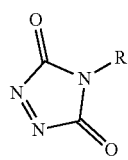

| PTAD | R group |
|---|---|
| 2a | 4-(CF$_3$)phenyl |
| 2b | 4-(prop-2-yn-1-yloxy)phenyl |
| 2c | 4-(OCF$_3$)phenyl |
| 2d | 4-(OC$_5$H$_{11}$)phenyl |
| 2e | Me |
| 2f | 4-(OC$_{16}$H$_{33}$)phenyl |

| PTAD | R group |
|---|---|
| 2g | 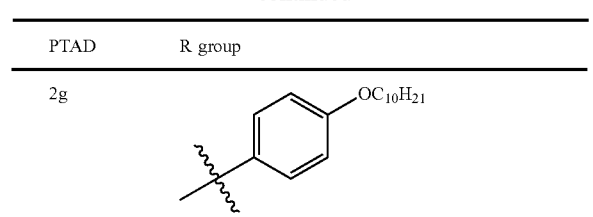 |
| PTAD | R group |
|---|---|
| 2h | 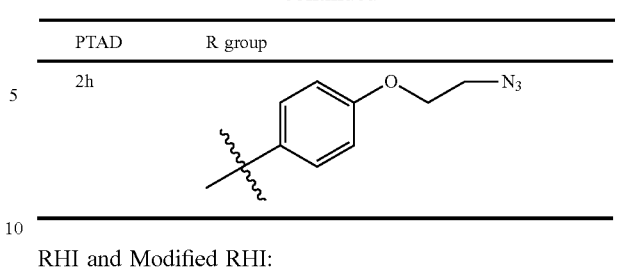 |
RHI and Modified RHI:
3a 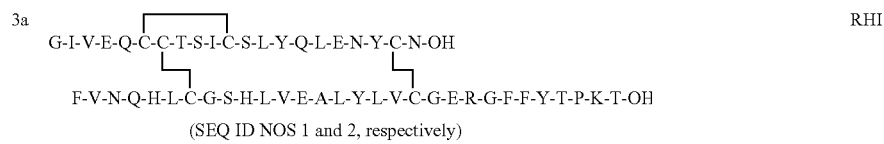 RHI
(SEQ ID NOS 1 and 2, respectively)
3b Bis-urea
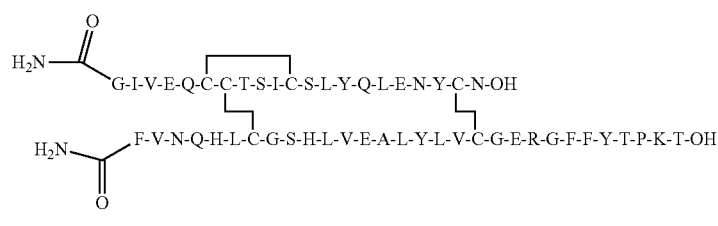
(SEQ ID NOS 10 and 11, respectively)
3c Tris-urea
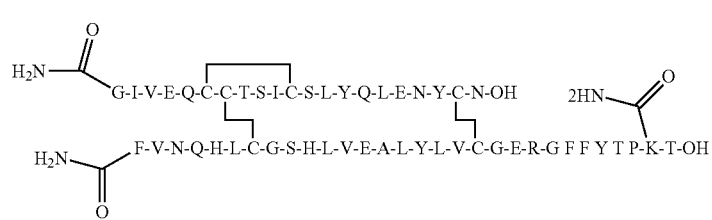
(SEQ ID NOS 10 and 12, respectively)
3d Bis-2-Oxopropoxyl Acetic acid
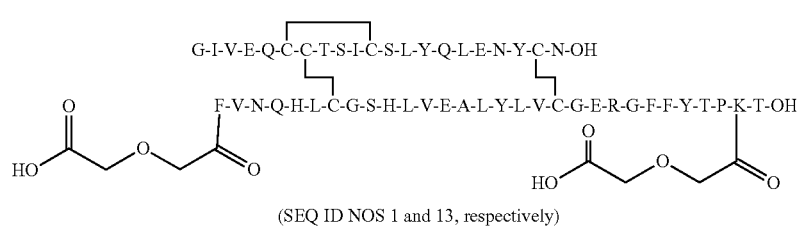
(SEQ ID NOS 1 and 13, respectively)
3e Bis-acyl
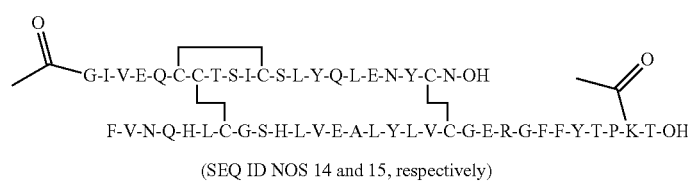
(SEQ ID NOS 14 and 15, respectively)

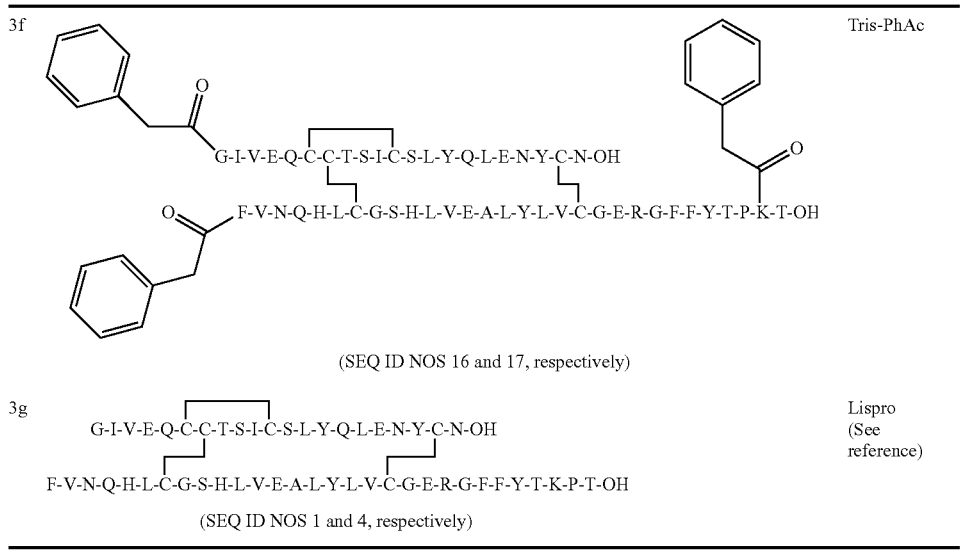

(SEQ ID NOS 16 and 17, respectively)

3g  G-I-V-E-Q-C-C-T-S-I-C-S-L-Y-Q-L-E-N-Y-C-N-OH    Lispro (See reference)

F-V-N-Q-H-L-C-G-S-H-L-V-E-A-L-Y-L-V-C-G-E-R-G-F-F-Y-T-K-P-T-OH (SEQ ID NOS 1 and 4, respectively)

Example 3b and 3c

Synthesis of $N^{2,1A},N^{2,1B},N^{6,29B}$-tris(carbamoyl) Human Insulin 3b (SEQ ID NOS 10 and 11, respectively)

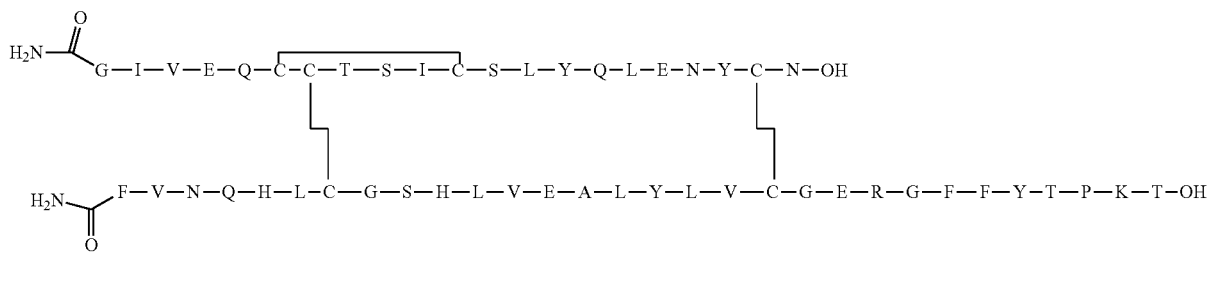

(SEQ ID NOS 10 and 12, respectively)

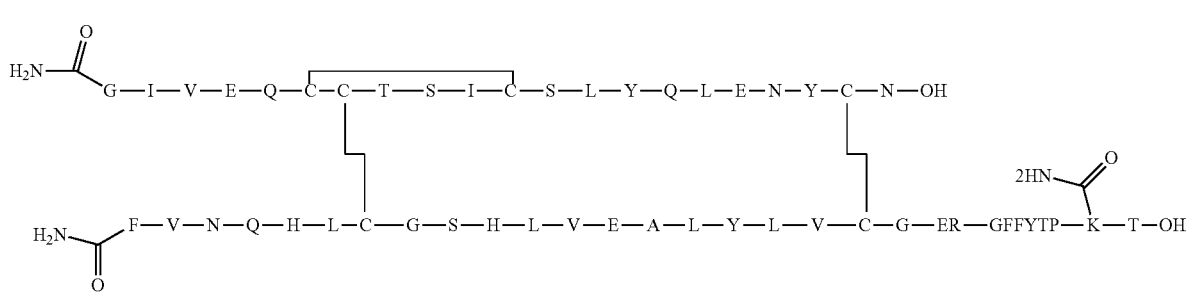

Human insulin-RHI (1.6 g, 0.276 mmol) was dissolved in a mixture of water (75 mL) and potassium phosphate, dibasic (0.398 g, 2.287 mmol) and added potassium cyanate (0.447 g, 5.51 mmol). The reaction was stirred overnight. Additional potassium cyanate (0.447 g, 5.51 mmol) was added and stirred for another 24 hr. More potassium cyanate (0.447 g, 5.51 mmol) was added and the mixture was stirred for another 24 hr. The product was purified by reverse-phase chromatography (Column Kromasil C8, size 250×50 mm, 10 μm, 100 Å column; solvent A=water/0.05% TFA, solvent B=ACN/0.05% TFA), Flow=85 mL/min, gradient B in A 26-34% over 30 min). UPLC-MS Method A: Rt=4.10 min, m/z=1485.00 [(M+4/4)].

Example 3d $N^{2,1B}, N^{6,29B}$-bis-2-(2-oxopropoxy) acetic acid RHI
(SEQ ID NOS 1 and 13, respectively)

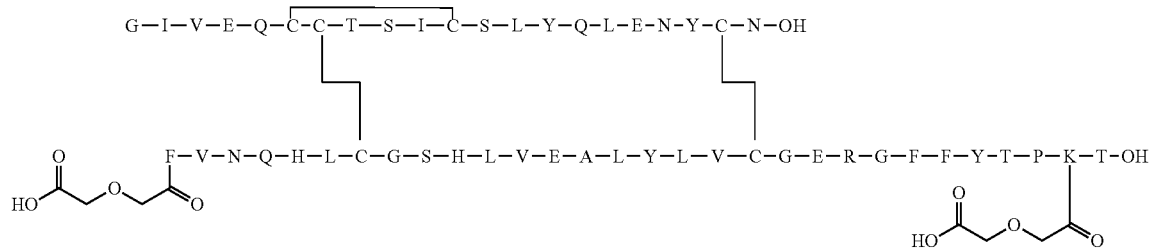

Step 1 Synthesis of $N^{2,1A}$-Trifluoroacetyl-RHI:

DIPEA (400 μl, 2.290 mmol) was added to a solution of RHI (1.0 g, 0.172 mmol) in DMSO (10.0 mL) and the resulting mixture was stirred at room temperature for 5 minutes. Isopropyl 2,2,2-trifluoroacetate (150 μl, 1.065 mmol) was then added dropwise to the reaction mixture and the resulting mixture was stirred at room temperature for 2 h. UPLC-MS Method B: Rt=3.65 min, m/z=1476.42 [(M+4)/4]. The crude reaction mixture was used in the following step without any purification.

Step 2 B1/B29 Bis oxyacetylation on $N^{2,1\ A}$-Trifluoroacetyl-RHI

To the reaction mixture from step 1, a solution of 1,4-dioxane-2,6-dione (40 mg, 0.345 mmol) in 100 μL DMSO was added and the resulting mixture was stirred at room temperature for 2 h. The crude reaction mixture was added dropwise to a round-bottom flask containing 150 mL of IPAc/MTBE (4:1). The resulting suspension was filtered and rinsed with (3×50 mL of IPAc). The material was dried under high vacuum for 1 h and used in the following step without any further purification. UPLC-MS Method B: Rt=3.86 min, m/z=1534.95 [(M+4)/4].

Step 3 Deprotection of trifluoroacetyl:

The crude product of step 2 was dissolved in 5.0 mL of 10% $CH_3CN$ in $H_2O$, then 5.0 mL of commercial $NH_4OH$ (28% m/v) was added dropwise at 0° C., and the mixture was stirred at the same temperature for 2 hours. Upon completion, the crude reaction mixture was concentrated to 5.0 mL using spin-dialysis on a 10K MWCO membrane Amicon tube, and diafiltration was continued using 100 mL water (pH=3.00) to a final volume of about 20 mL. The product was purified by reverse-phase chromatography (Column Kromasil C8, size 250×50 mm, 10 μm, 100 Å column; solvent A=water/0.1% TFA; solvent B=ACN/0.1% TFAcan, Flow=85 mL/min,). Fractions containing the title conjugate were combined and lyophilized to give the title product as a white solid. UPLC-MS Method B: Rt=3.68 min, m/z=1510.64 [(M+4)/4].

Example 3e

Synthesis of $N^{2,1A}, N^{6,29B}$-bis(acetyl) Human Insulin
(SEQ ID NOS 14 and 15, respectively)

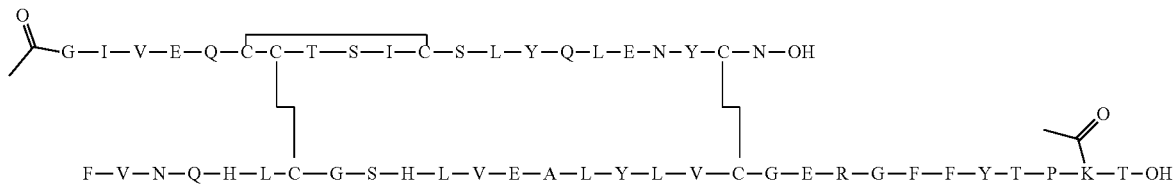

RHI (3 g, 0.517 mmol) was dissolved in a mixture of Na$_2$CO$_3$(0.1M) (18.23 ml) and acetonitrile (12.15 ml) and adjusted to pH=10.5. A solution of N-acetoxysuccinimide (0.106 g, 0.672 mmol) was added to a small (600 µL) volume of acetonitrile. A mixture of mono- and di-conjugated product was observed at the end of the reaction, favoring the mono-conjugated product in a ratio of approximately 3:1. The reaction mixture was pH-adjusted to pH=2.5 with 1M HCl and the product of bis-conjugation was separated from the product of mono-conjugation by reverse-phase chromatography (Column Kromasil C8, size 250×50 mm, 10 µm, 100 Å column solvent A=water/0.05% TFA, solvent B=ACN/0.05% TFA), Flow=85 mL/min, gradient B in A 26-35% in 30 min). UPLC-MS Method A: Rt=3.65 min, m/z=1473.70 [(M+4/4)].

Example 3f

Synthesis of $N^{2,1A}, N^{2,1B}, N^{6,29B}$-tris((C$_6$H$_5$)CH$_2$CO) Human Insulin (SEQ ID NOS 16 and 17, respectively)

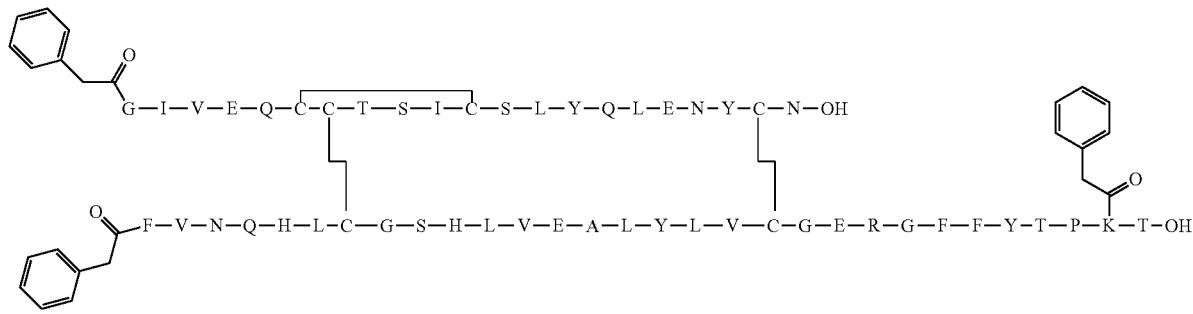

DMSO (200 mL) was added to a 1000 mL three-neck round-bottomed flask with a magnetic stir bar, thermocouple inlet and nitrogen inlet at a temperature of 23.2° C. RHI (45 g, 7.75 mmol) was added portion wise as a solid over two minutes slowly. DMSO (160 mL) was added to wash any solids down the sides of the flask. After all the insulin was dissolved, the temperature was raised to 25.4° C. Hunig's Base (9.00 ml, 51.5 mmol) was added and then 2,5-dioxopyrrolidin-1-yl 2-phenylacetate (9.04 g, 38.7 mmol) was added as a solid in one portion. The funnel was rinsed with 10 mL DMSO. The reaction temperature was adjusted to 25.1° C. and the mixture was stirred at room temperature for 30 min.

The reaction mixture was poured (over 4 minutes) into 5 L 3-neck round bottomed flask containing IPAc (3375 ml) which was stirred at 100 RPM. The reaction flask was rinsed with DMSO (36.0 ml) and the rinsate was poured into the IPAc mixture. The suspension was stirred at room temperature for 30 minutes. The solids were collected via filtration, washed with 3×350 mL IPAc, then dried by pulling vacuum through the filter with a nitrogen bag over the filter overnight to afford A1,B1,B29-tris-PhAc RHI as a solid. UPLC-MS Method C: Rt=2.28 min, m/z=1541.49 [(M+4)/4].

Example 4

General Method: PTAD Modification of Insulin

A solution of RHI analog (180 mg, 0.030 mmol) in 1:1/Acetonitrile:100 mM NaPhosphate buffer pH 7.5 (10 mL, 0.003M solution) was prepared and cooled in a salt/ice bath to −5° C. A solution of R-3H-1,2,4-triazole-3,5(4H)-dione in anhydrous acetonitrile (0.045 M) was prepared and added (1 eq) dropwise to the cold and mixing RHI solution. After 40 min, another 0.5 eq was added to the cold reaction. Three single-addition products are generally observed (A14, B16, B26 positions, A19 also possible) and also bis-addition products. The volume of the reaction mixture was reduced and the pH was adjusted to 2-2.5 with TFA. The product was filtered and purified by reverse phase C18 column chromatography.

For orthogonal bis-PTAD modification (compounds 18-20 and 22 with RHI_A1_B1 bis-Urea) the general procedure above was employed using PTAD 2c (compounds #18-20) and PTAD 2d (compound 22). Isolation of the major product (A14 modification) by reverse phase HPLC was followed by a second PTAD modification using PTAD 2b and following the general procedure for PTAD modification above.

TABLE 2

| | Analogs | | | | | |
|---|---|---|---|---|---|---|
| Compound # | Description | RHI | PTAD | [(M + 4)/4] observed | Analytical method | Analytical Rt |
| 1 | RHI_A1_B1_B29_tris-Urea_A14_PTAD PhO-propyne | 3c | 2b(A14) | 1542.39 | C | 1.85 |

TABLE 2-continued

| | Analogs | | | | | |
|---|---|---|---|---|---|---|
| Compound # | Description | RHI | PTAD | [(M + 4)/4] observed | Analytical method | Analytical Rt |
| 2 | RHI_A1_B1_B29_tris-Urea_A14_B26_PTAD PhO-propyne | 3c | 2b (A14, B26) | 1599.57 | C | 1.93 |
| 3 | RHI_A1_B29_bis-Acyl_B1_H_A14_PTAD PhO-propyne | 3e | 2b(A14) | 1530.93 | C | 1.82 |
| 4 | RHI_A1_B29_bis-Acyl_B1_H_A14_B26_PTAD PhO-propyne | 3e | 2b (A14, B26) | 1587.84 | C | 1.94 |
| 5 | RHI_A1_B1_bis-Urea_B29_H_B16_PTAD PhO-propyne | 3b | 2b(B16) | 1530.89 | C | 1.83 |
| 6 | RHI_A1_B1_bis-Urea_B29_H_B26_PTAD PhO-propyne | 3b | 2b(B26) | 1531.37 | C | 1.85 |
| 7 | RHI_A1_B1_bis-Urea_B29_H_A14_PTAD PhO-propyne | 3b | 2b(A14) | 1531.64 | C | 1.84 |
| 8 | RHI_A1_B1_B29_tris-Urea_B16_PTAD PhO-propyne | 3c | 2b(B16) | 1541.89 | C | 1.85 |
| 9 | RHI_A1_B1_B29_tris-Urea_B26_PTAD PhO-propyne | 3c | 2b(B26) | 1542.75 | C | 1.86 |
| 10 | RHI_A1_B29_bis-Acyl_B1_H_B16_PTAD PhO-propyne | 3e | 2b(B16) | 1531.45 | C | 2.24 |
| 11 | RHI_A1_B29_bis-Acyl_B1_H_B26_PTAD PhO-propyne | 3e | 2b(B26) | 1531.46 | C | 2.27 |
| 12 | Lispro_A14_PTAD PhO-propyne | 3g | 2b(A14) | 1510.65 | C | 2.09 |
| 13 | Lispro_B16_PTAD Me | 3g | 2e(B16) | 1481.04 | D | 8.08 (15 min method) |
| 14 | Lispro_A14_PTAD Me | 3g | 2e(A14) | 1480.74 | D | 8.08 (15 min method) |
| 15 | RHI_A1_H_B1_B29_bis-COCH$_2$OCH$_2$CO$_2$H_A14_PTAD PhO-propyne | 3d | 2b(A14) | 1568.43 | C | 2.44 |
| 16 | RHI_A1_B1_B29_tris-PhAc_A14_PTAD PhO-propyne | 3f | 2b(A14) | 1598.93 | C | 2.33 |
| 17 | RHI_A1_B1_bis-Urea_B29_H_A14_PTAD PhOCF$_3$ | 3b | 2c(A14) | 1538.2 | C | 1.95 |
| 18 | RHI_A1_B1_bis-Urea_B29_H_A14_PTAD PhOCF$_3$_A19_PTAD PhO-propyne | 3b | 2c(A14)/ 2b(A19) | 1595.85 | C | 1.97 |
| 19 | RHI_A1_B1_bis-Urea_B29_H_A14_PTAD PhOCF$_3$_B16_PTAD PhO-propyne | 3b | 2c(A14)/ 2b(B16) | 1596.20 | C | 1.97 |
| 20 | RHI_A1_B1_bis-Urea_B29_H_A14_PTAD PhOCF$_3$_B26_PTAD PhO-propyne | 3b | 2c(A14)/ 2b(B26) | 1596.56 | C | 2.00 |
| 21 | RHI_A1_B1_bis-Urea_B29_H_A14_PTAD PhOC$_5$H$_{11}$ | 3b | 2d(A14) | 1540.02 | C | 2.03 |
| 22 | RHI_A1_B1_bis-Urea_B29_H_A14_PTAD PhOC$_5$H$_{11}$_B26_PTAD PhO-propyne | 3b | 2d(A14)/ 2b(B26) | 1597.02 | C | 2.08 |
| 23 | RHI_A1_B1_B29_H_A14_PTAD PhOC$_5$H$_{11}$ | 3a | 2d(A14) | 1517.83 | C | 1.59 |
| 24 | RHI_A1_B1_B29_H_A14_PTAD PhOCH$_2$CH$_2$N$_3$ | 3a | 2h(A14) | 1517.91 | C | 1.44 |
| 25 | RHI_A1_B1_B29_H_A14_PTAD PhO-propyne | 3a | 2b(A14) | 1509.73 | C | 1.43 |

COMPOUND 1
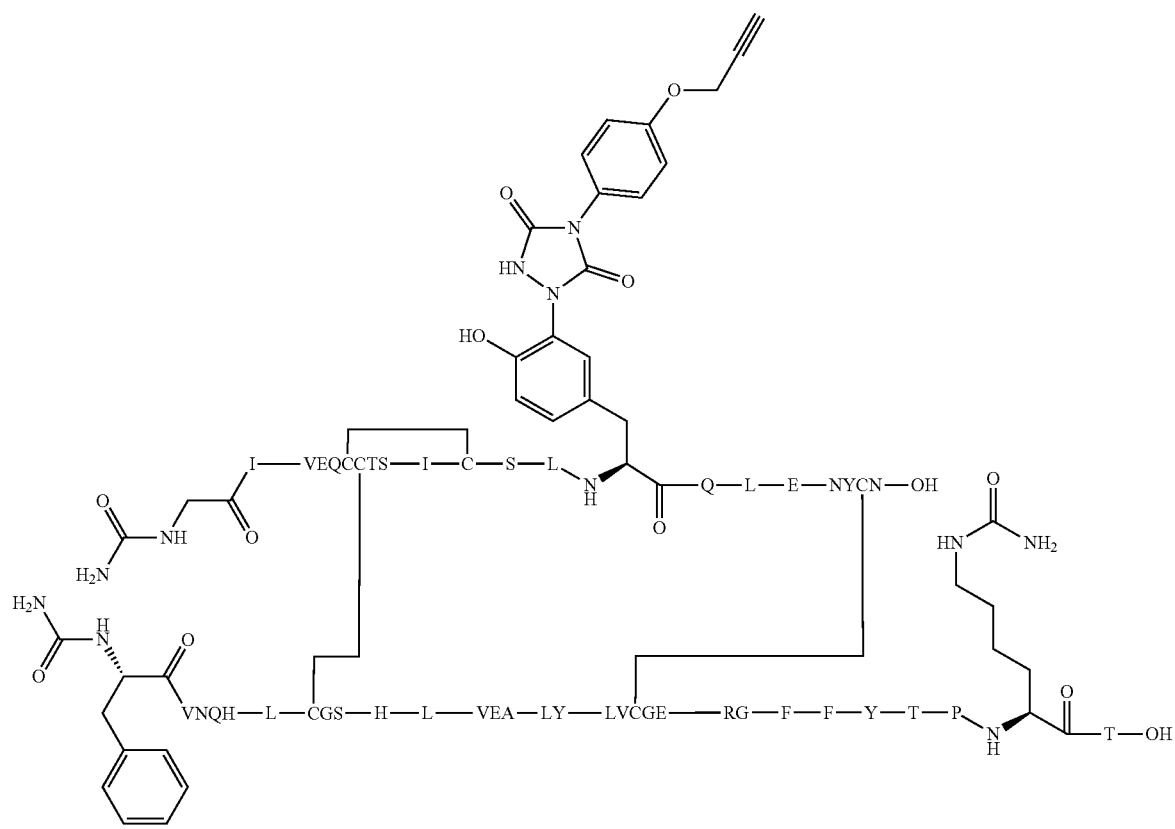
(SEQ ID NOS 18 and 19, respectively)
COMPOUND 2
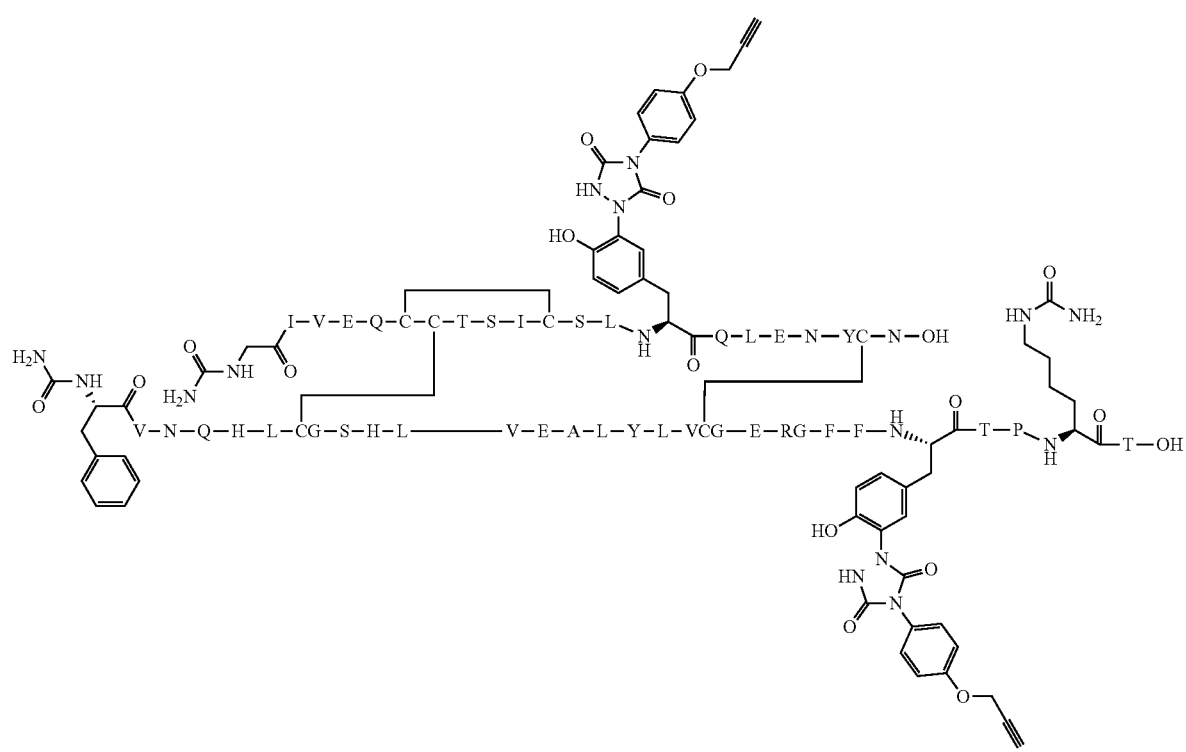
(SEQ ID NOS 18 and 20, respectively)

COMPOUND 3
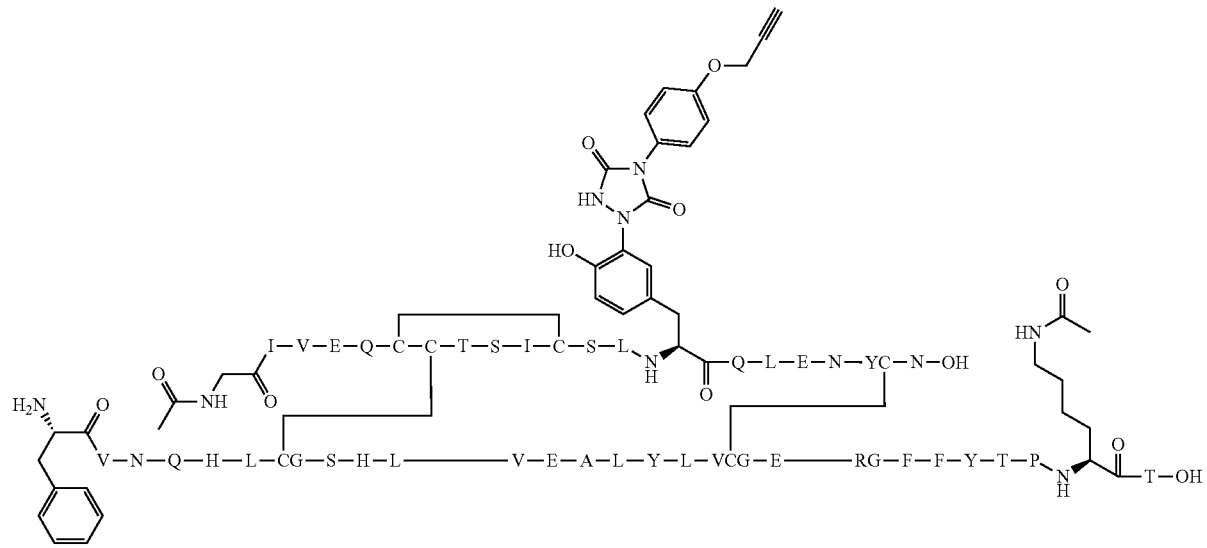
(SEQ ID NOS 21 and 22, respectively)
COMPOUND 4
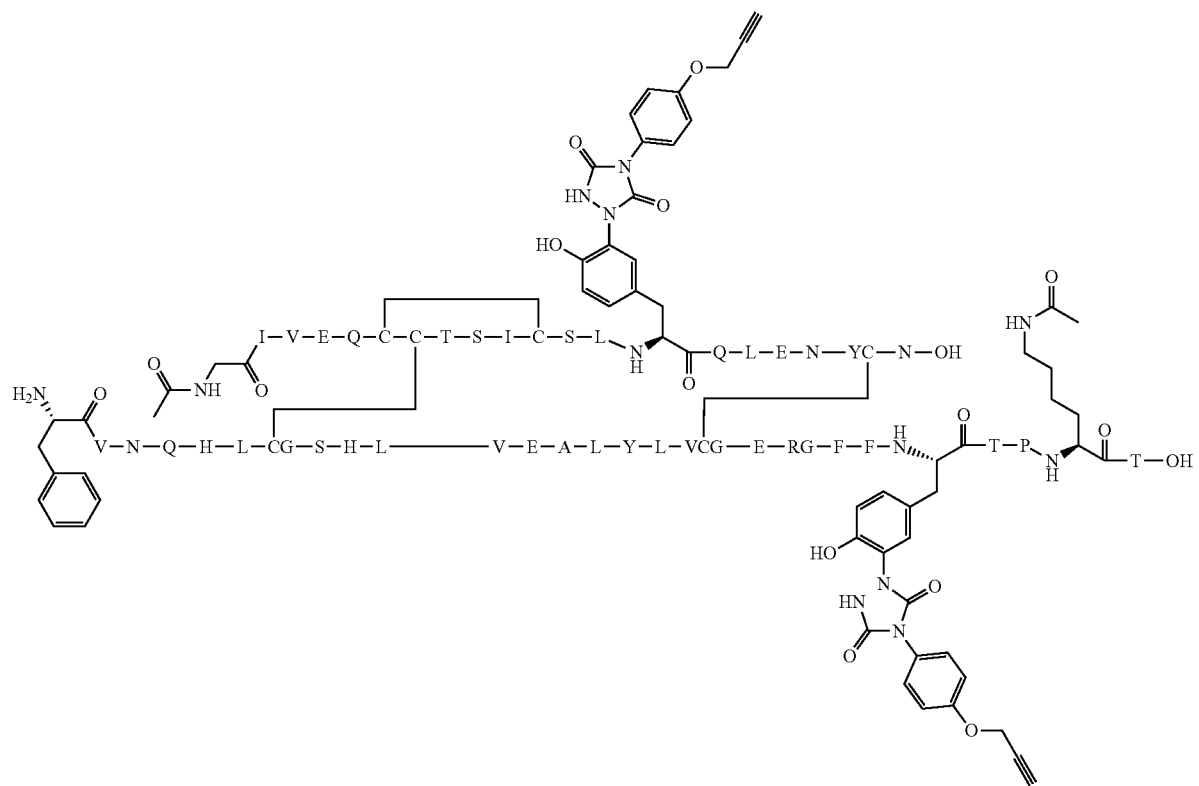
(SEQ ID NOS 21 and 23, respectively)

COMPOUND 5
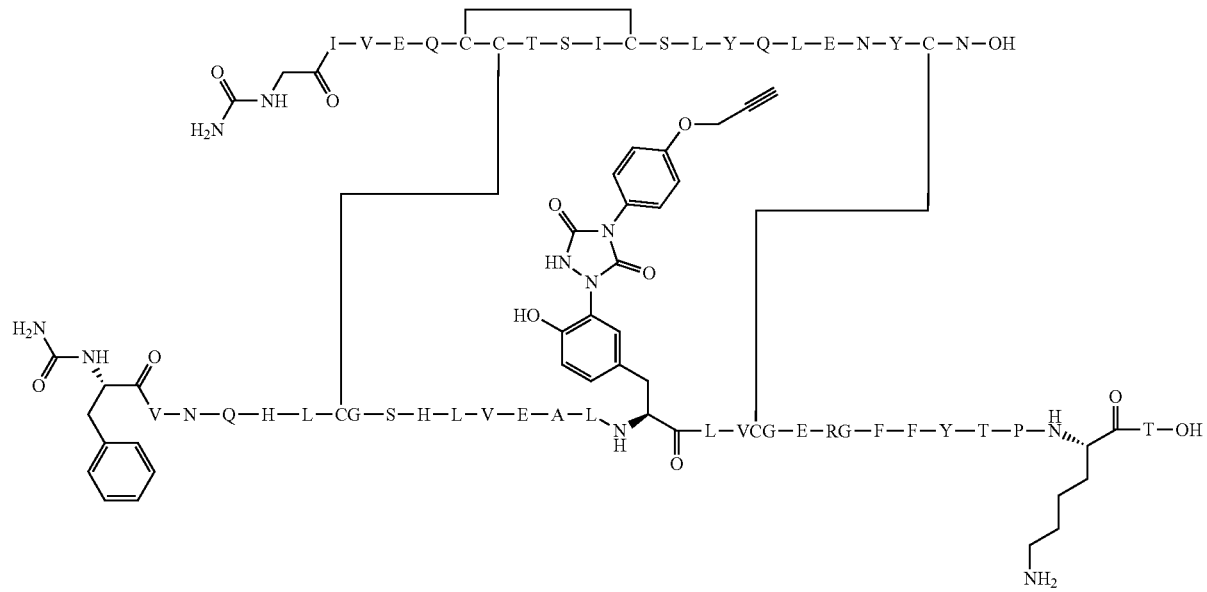
(SEQ ID NOS 24 and 25, respectively)
COMPOUND 6
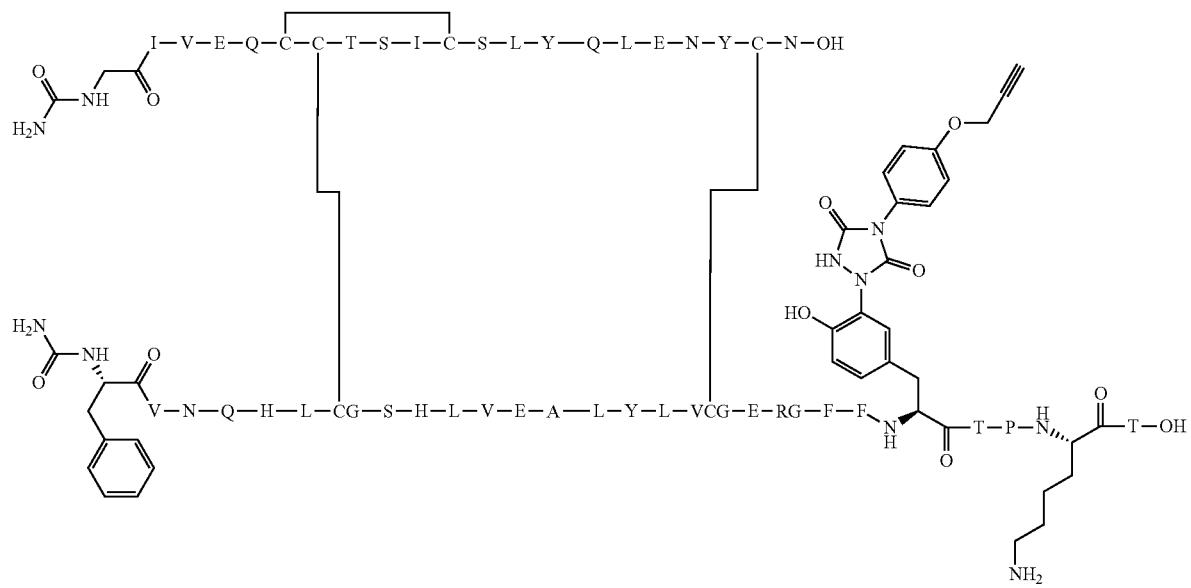
(SEQ ID NOS 24 and 26, respectively)

COMPOUND 7
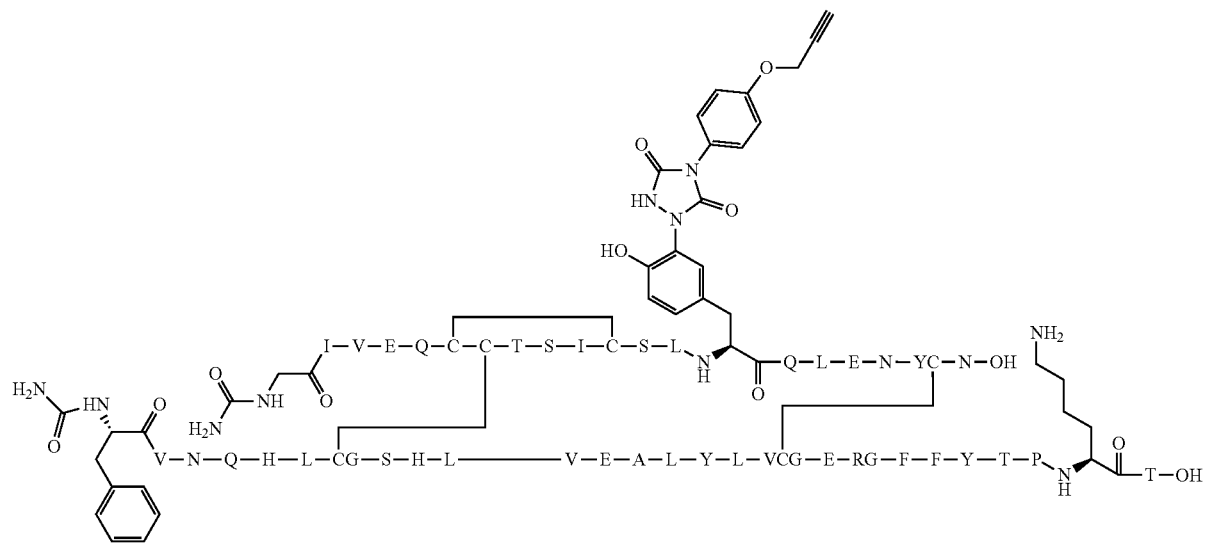
(SEQ ID NOS 18 and 27, respectively)
COMPOUND 8
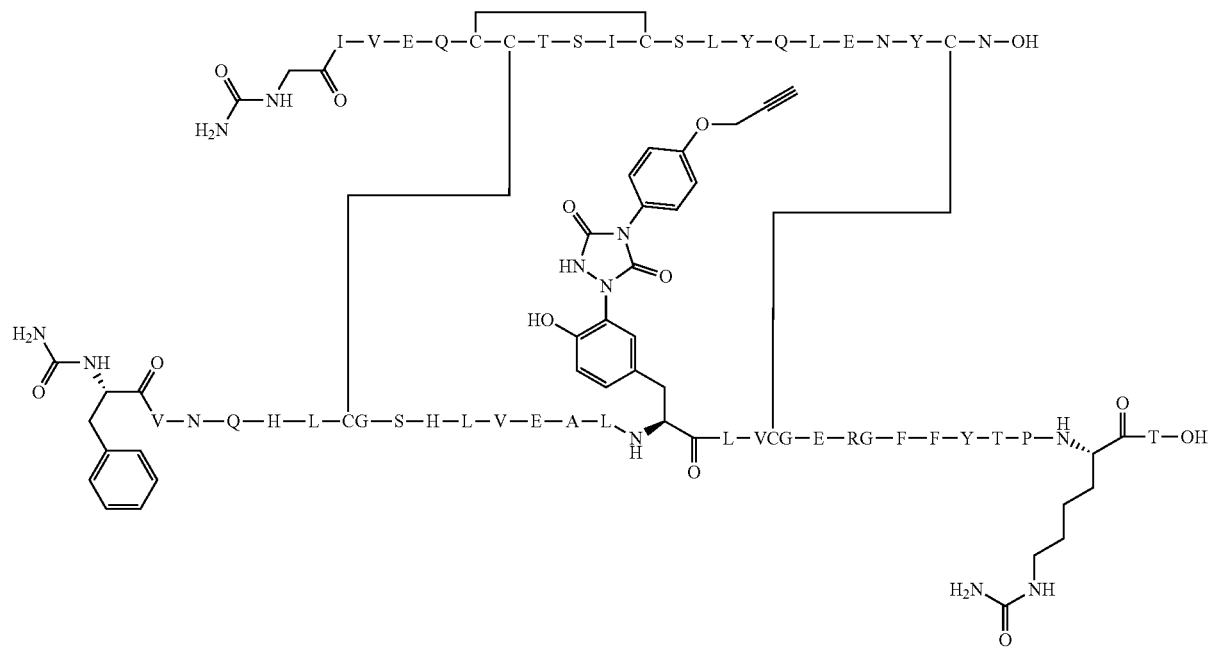
(SEQ ID NOS 24 and 28, respectively)

COMPOUND 9
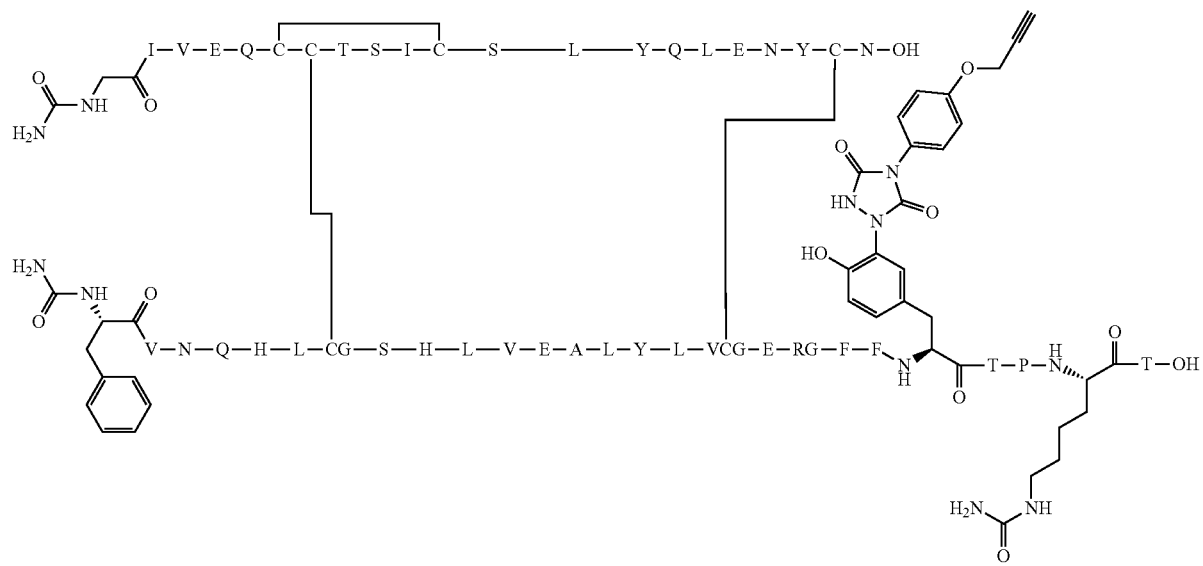
(SEQ ID NOS 24 and 20, respectively)
COMPOUND 10
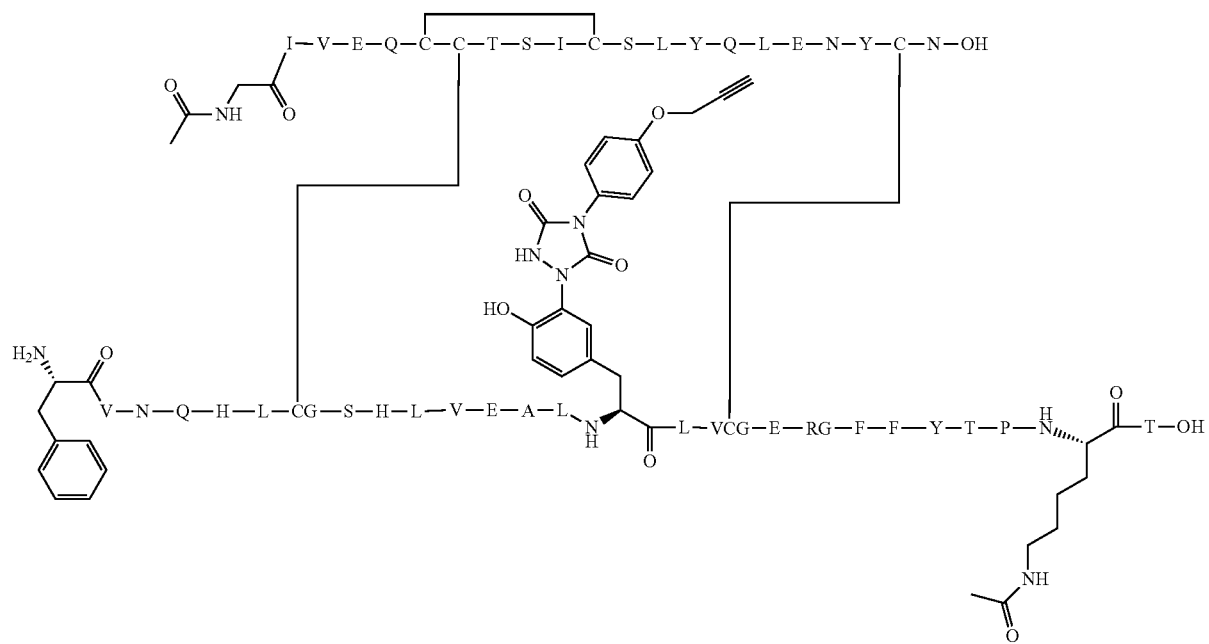
(SEQ ID NOS 29 and 30, respectively)

COMPOUND 11
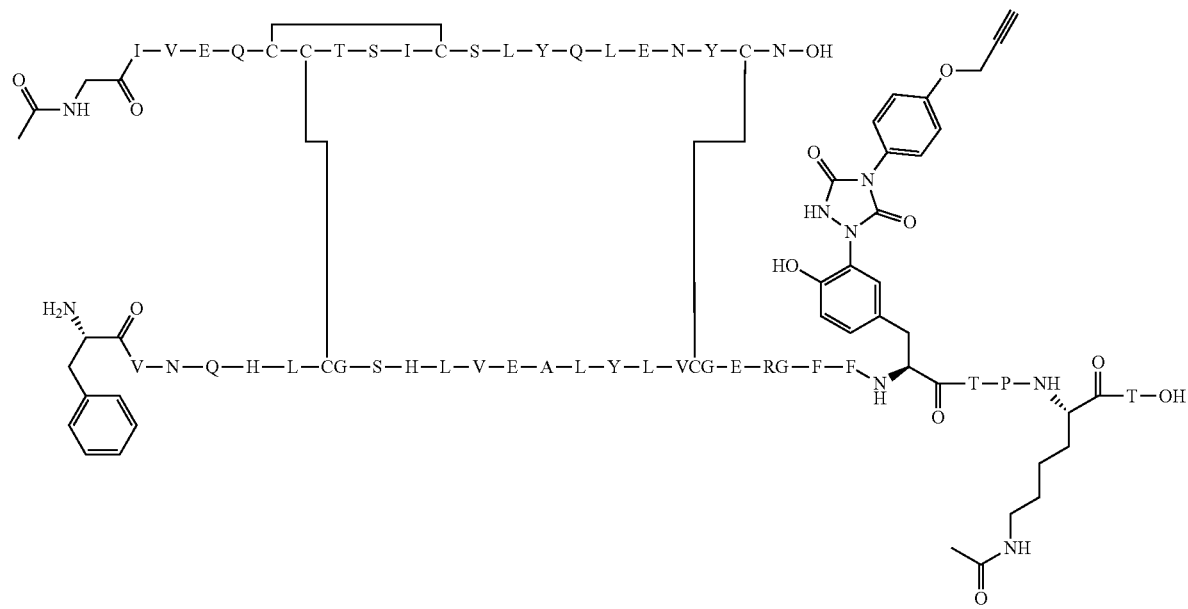
(SEQ ID NOS 29 and 23, respectively)
COMPOUND 12
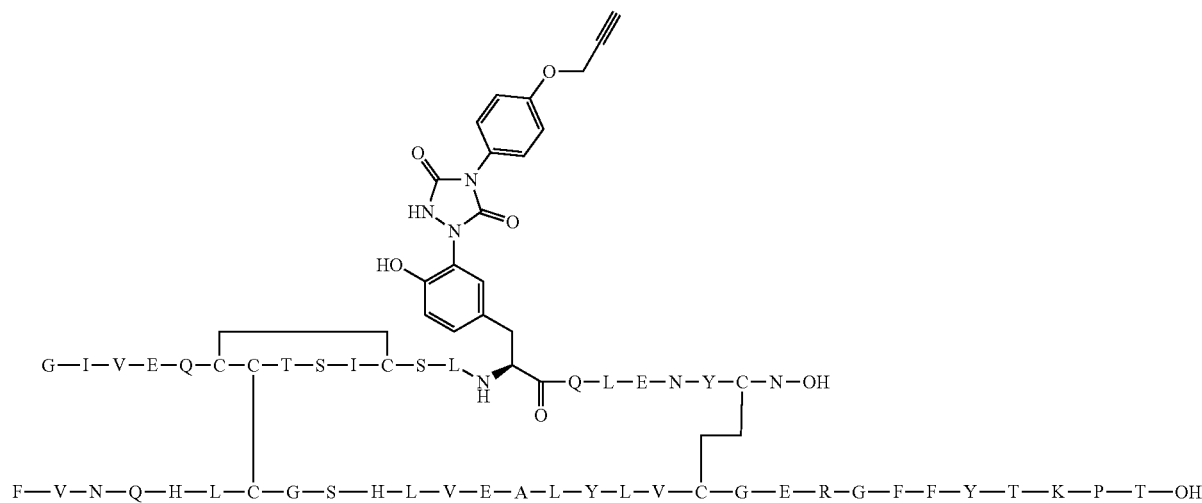
(SEQ ID NOS 31 and 4, respectively)

COMPOUND 13
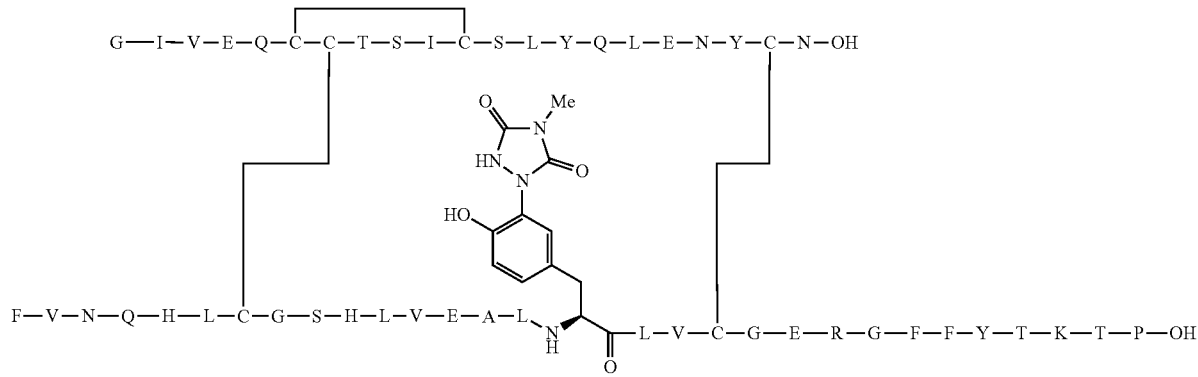
(SEQ ID NOS 1 and 32, respectively)
COMPOUND 14
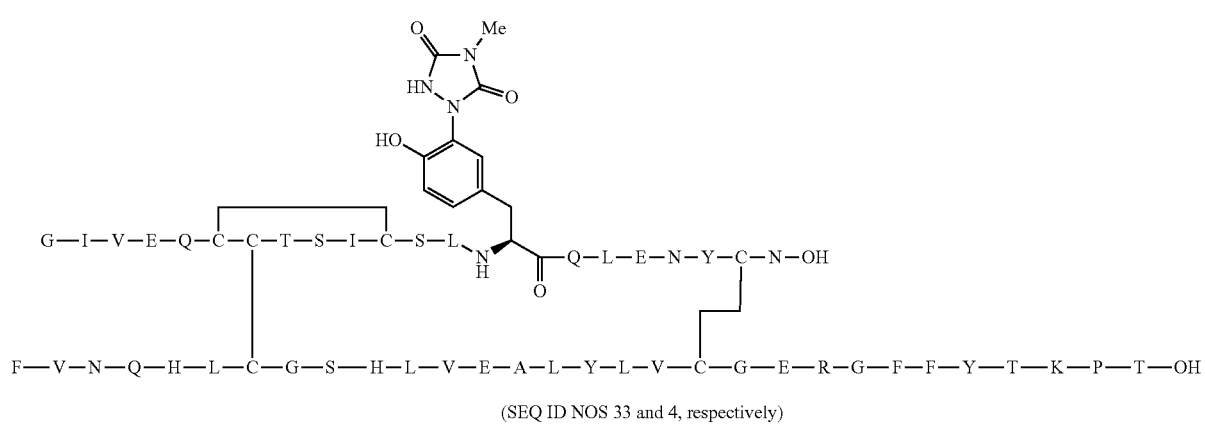
(SEQ ID NOS 33 and 4, respectively)
COMPOUND 15
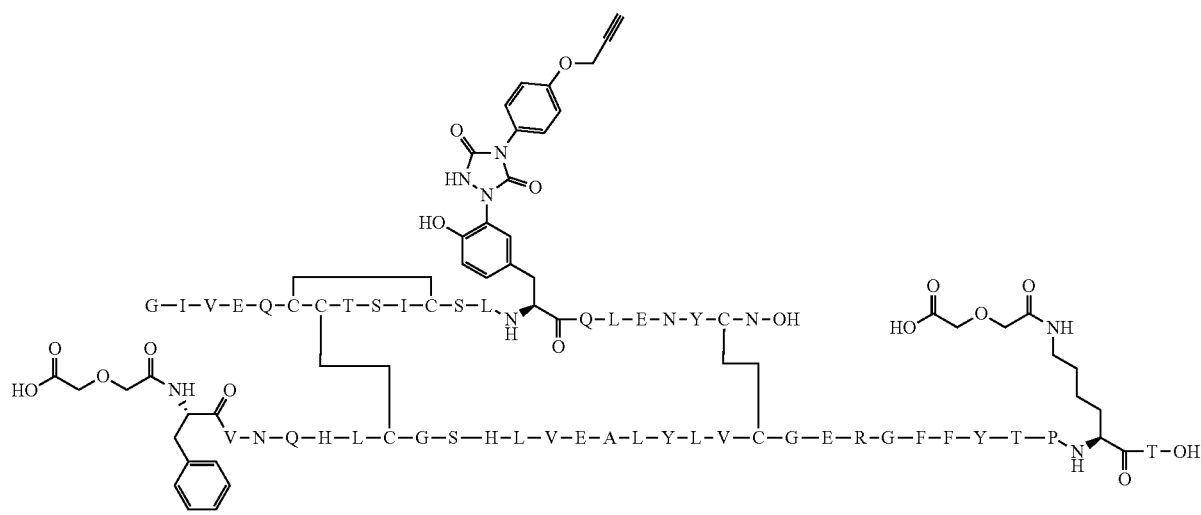
(SEQ ID NOS 31 and 34, respectively)

COMPOUND 16
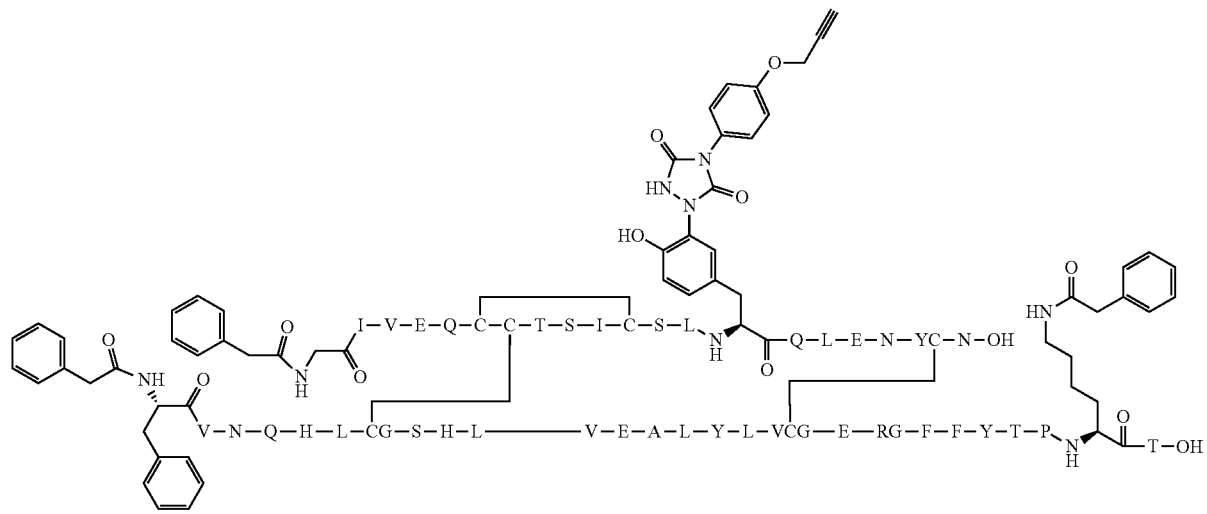
(SEQ ID NOS 35 and 36, respectively)
COMPOUND 17
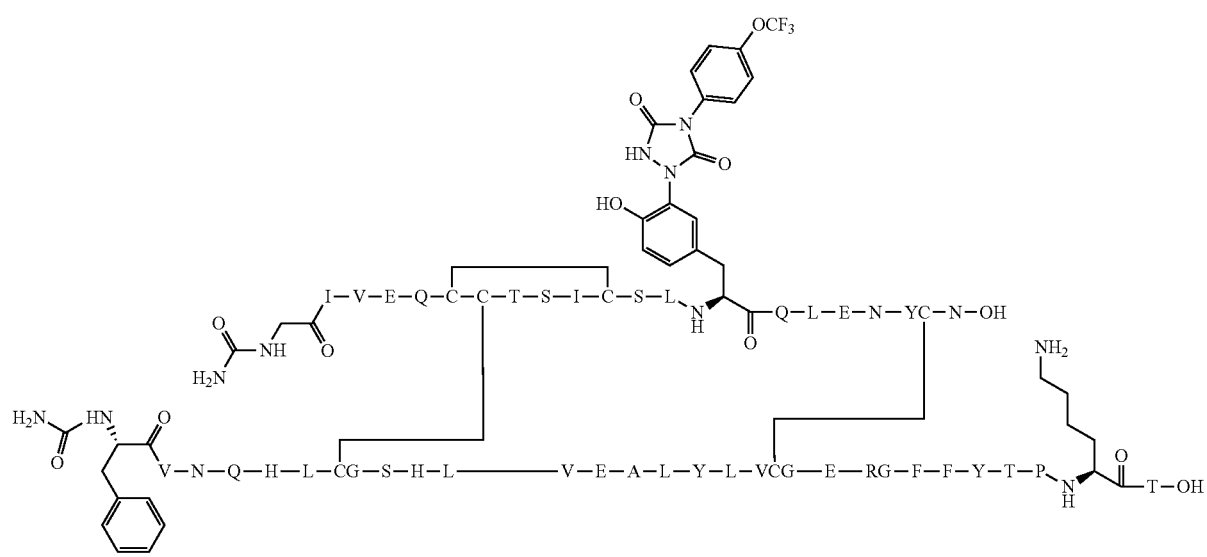
(SEQ ID NOS 37 and 27, respectively)

COMPOUND 18
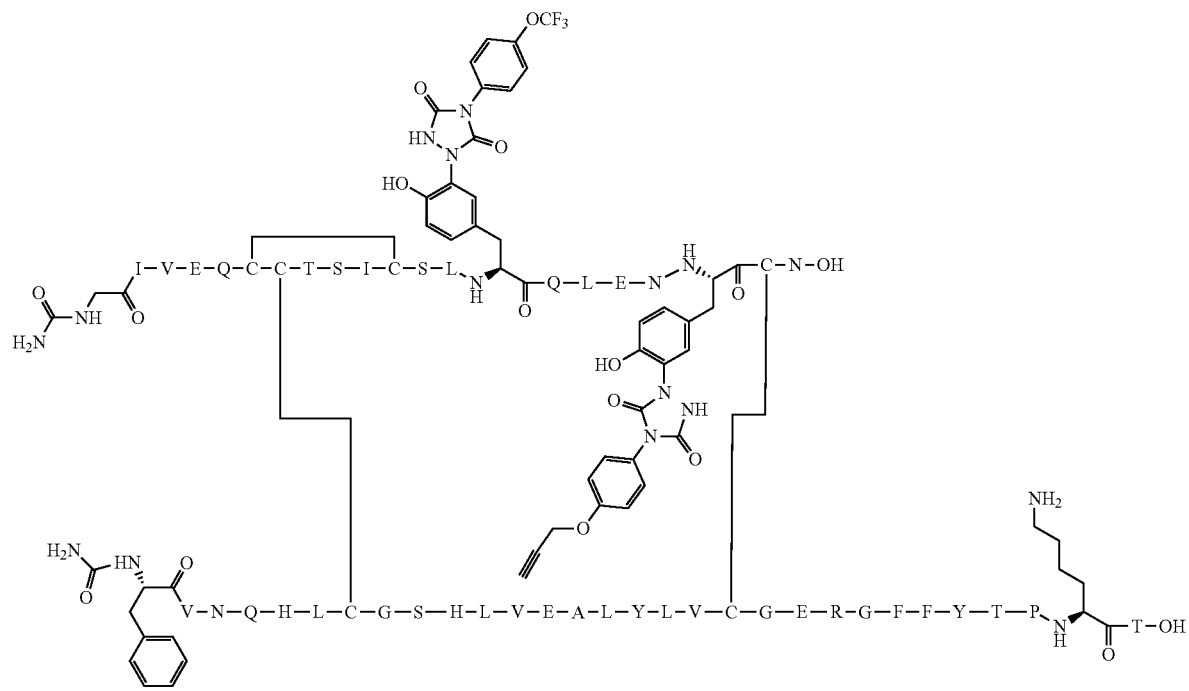
(SEQ ID NOS 38 and 27, respectively)
COMPOUND 19
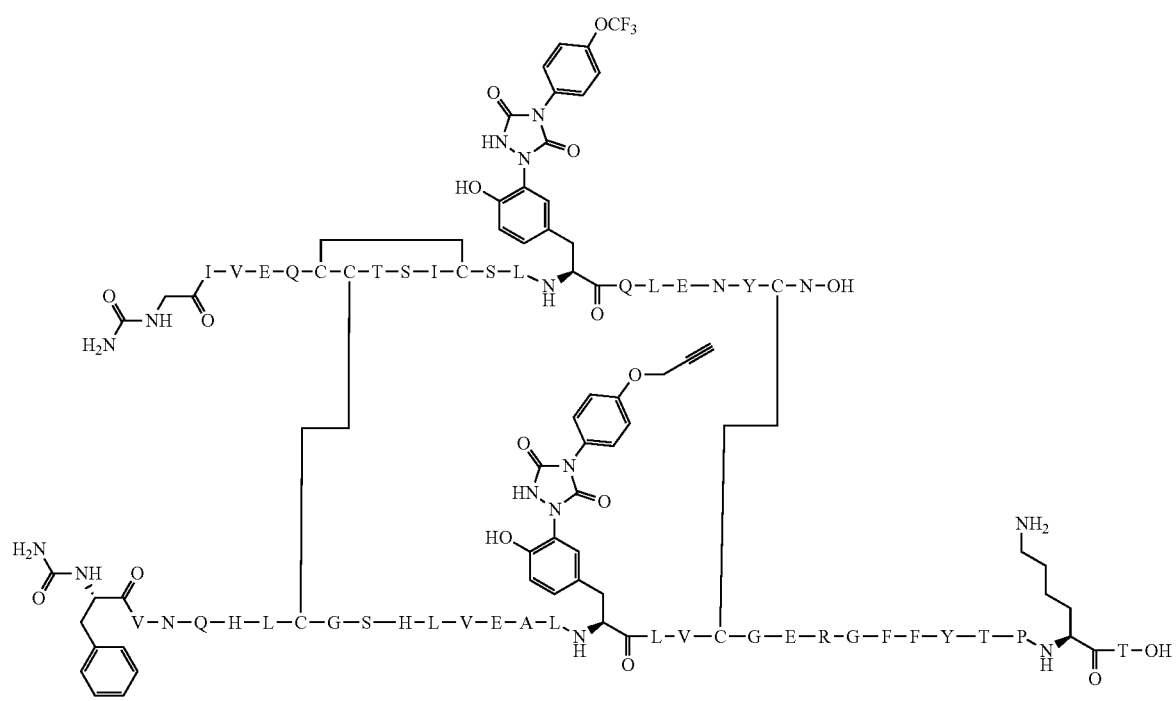
(SEQ ID NOS 37 and 25, respectively)

COMPOUND 20
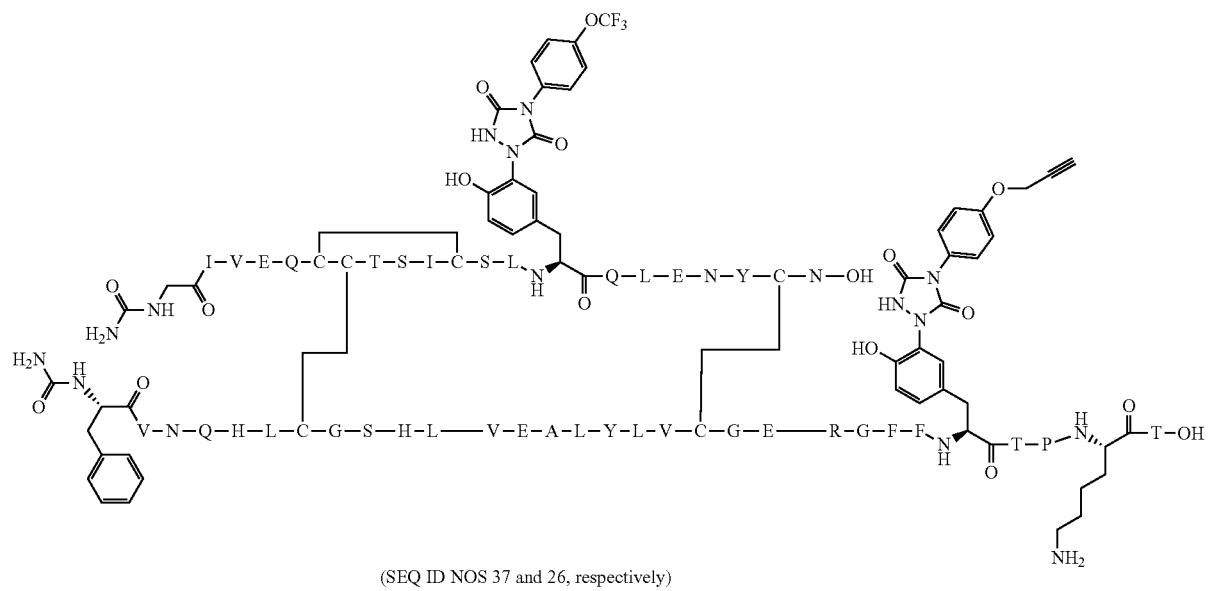
(SEQ ID NOS 37 and 26, respectively)
COMPOUND 21
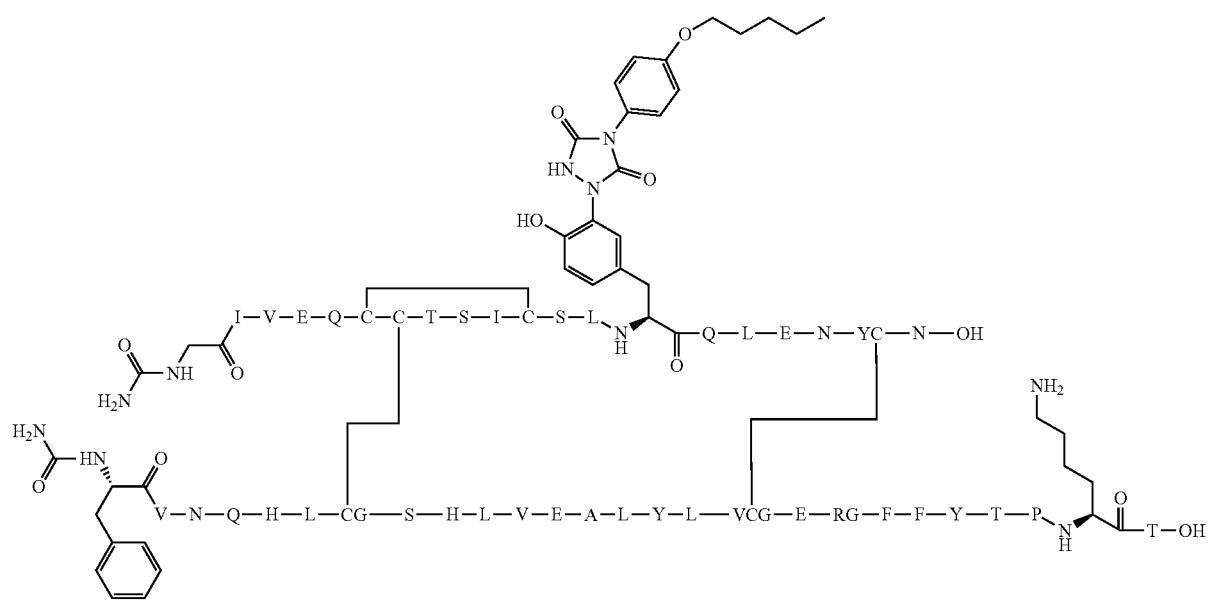
(SEQ ID NOS 39 and 27, respectively)

COMPOUND 22
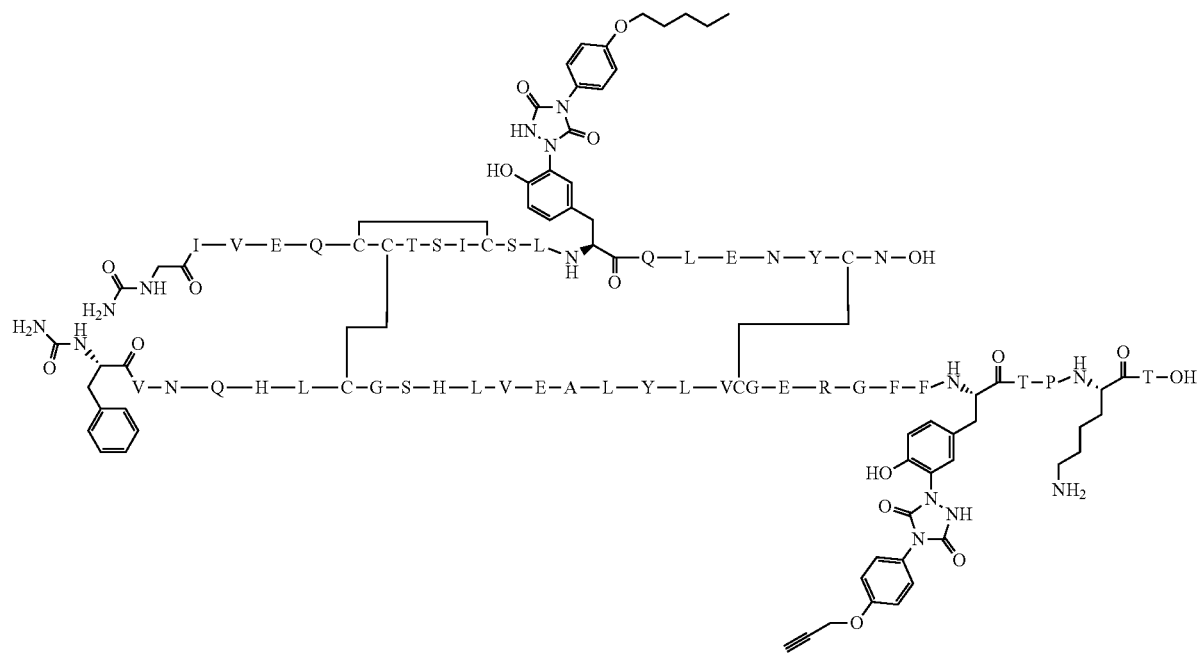
(SEQ ID NOS 39 and 26, respectively)
COMPOUND 23
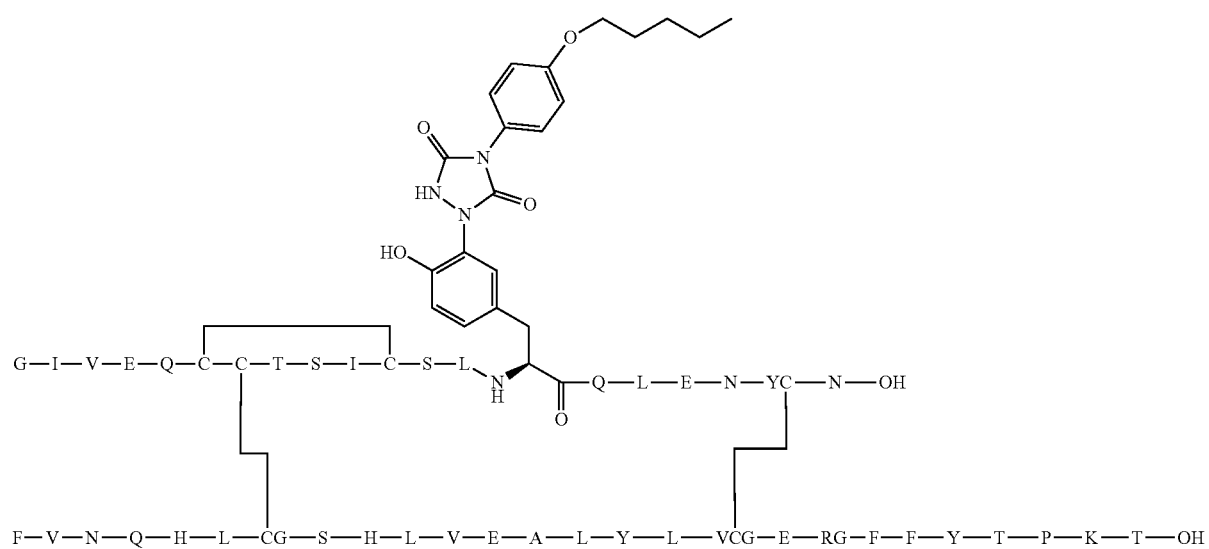
(SEQ ID NOS 40 and 2, respectively)

-continued
COMPOUND 24
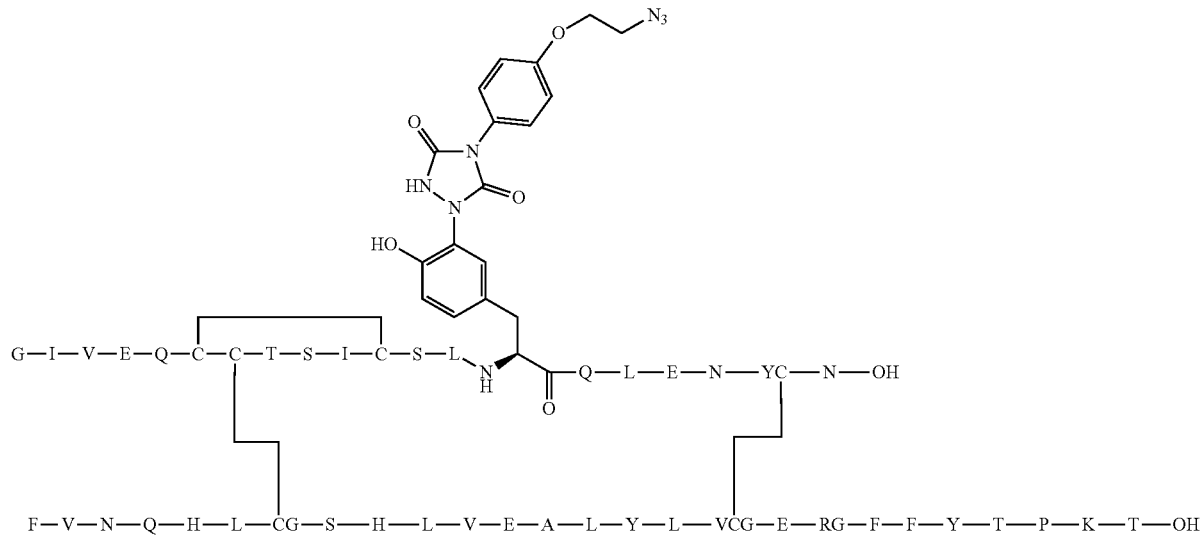
(SEQ ID NOS 41 and 2, respectively)
COMPOUND 25
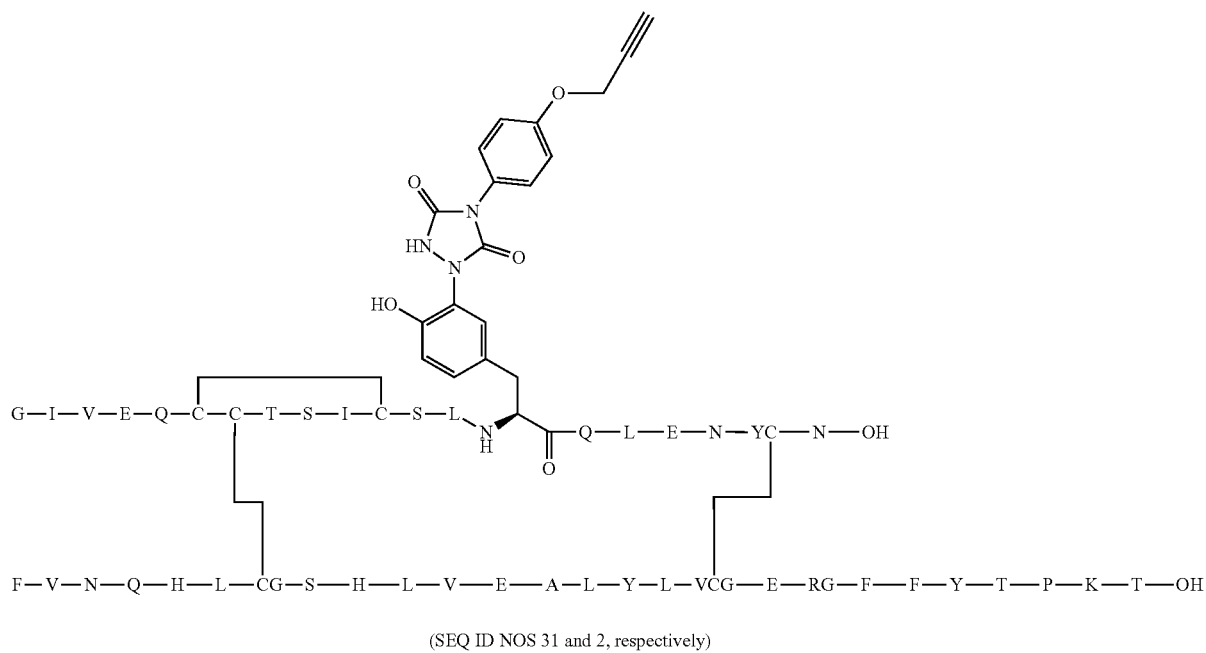
(SEQ ID NOS 31 and 2, respectively)
| POTENCY DATA TABLES | | | | |
|---|---|---|---|---|
| Compound # | Description | IR Membrane Binding, nM, % Inh | pAkt_Ec50 (nM) | pAkt_% Act |
| 1 | RHI_A1_B1_B29_tris-Urea_A14_PTAD PhO-propyne | 4.064 (89) | 0.185 | 97.9 |
| 2 | RHI_A1_B1_B29_tris-Urea_A14_B26_PTAD PhO-propyne | 11.43 (101.4) | 0.115 | 95.1 |
| 3 | RHI_A1_B29_bis-Acyl_B1_H_A14_PTAD PhO-propyne | 1.57 (58.8) | 0.220 | 92.8 |
| 4 | RHI_A1_B29_bis-Acyl_B1_H_A14_B26_PTAD PhO-propyne | 22.04 (110.6) | 0.564 | 94.2 |

What is claimed:

1. A compound, or pharmaceutically acceptable salt thereof, selected from:

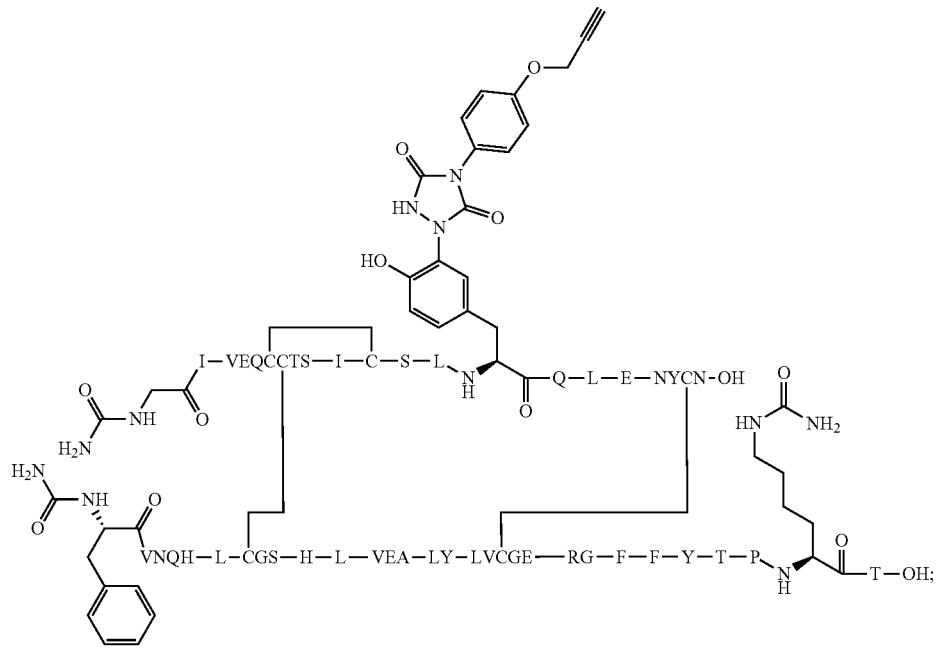

COMPOUND 1 (SEQ ID NOS 18 and 19, respectively)

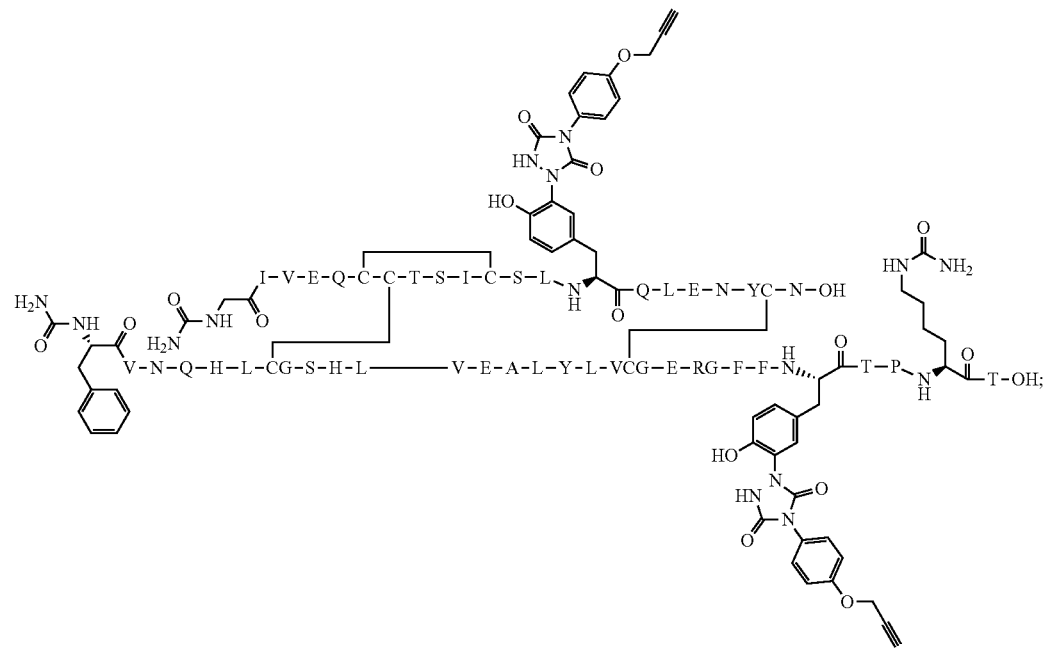
COMPOUND 2 (SEQ ID NOS 18 and 20, respectively)
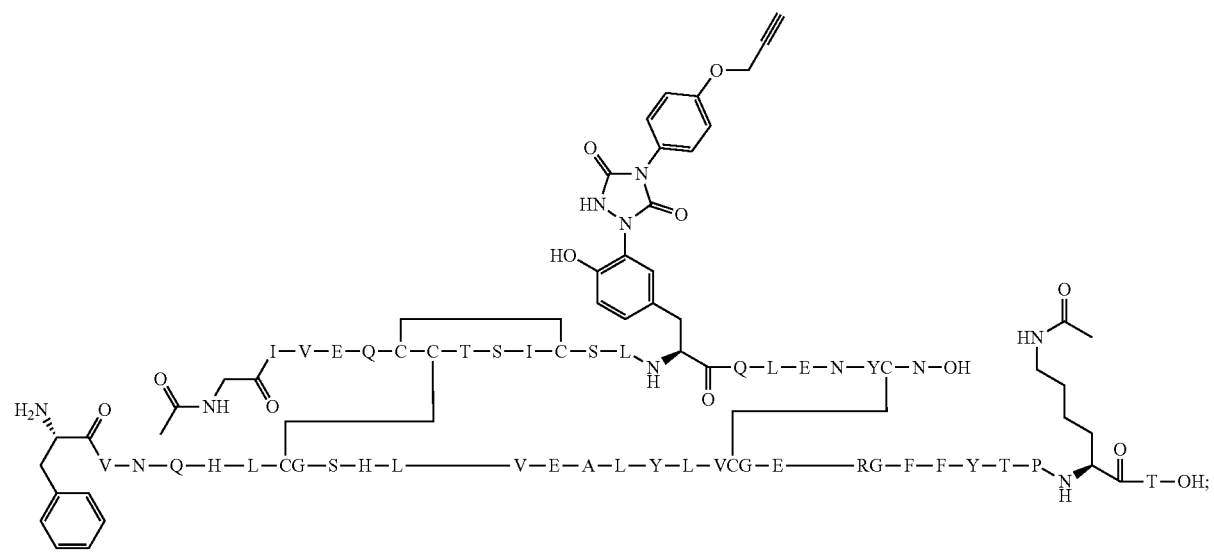
COMPOUND 3 (SEQ ID NOS 21 and 22, respectively)

-continued
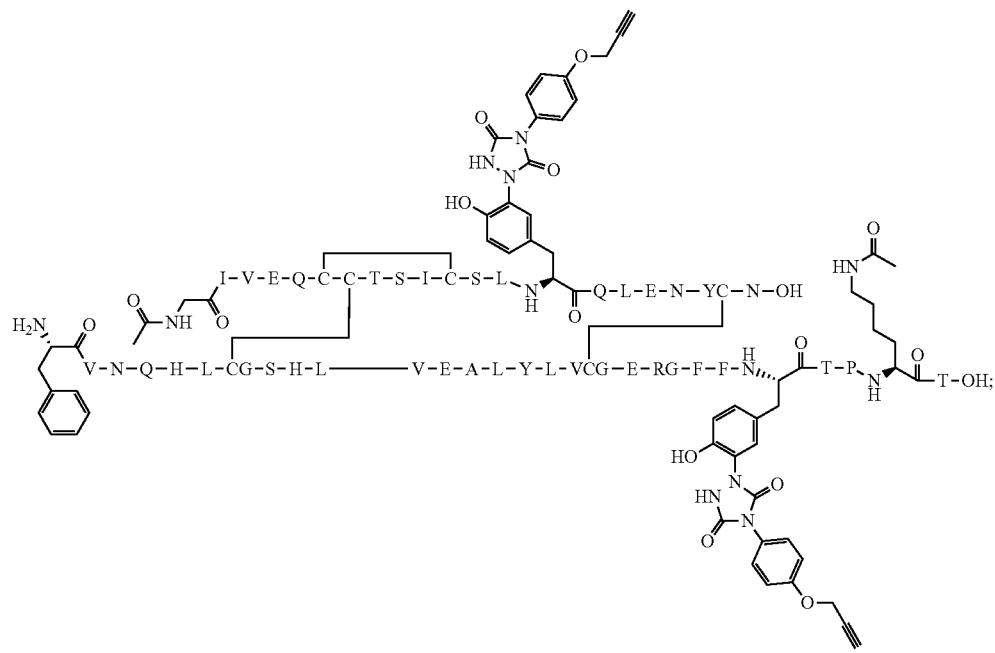
COMPOUND 4 (SEQ ID NOS 21 and 23, respectively)
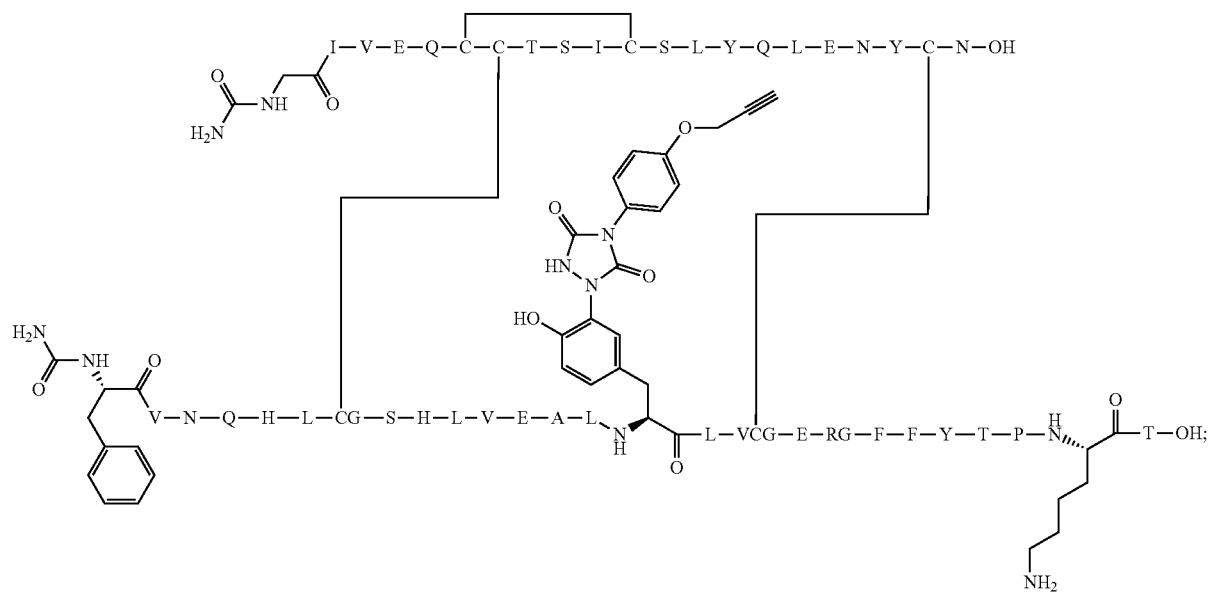
COMPOUND 5 (SEQ ID NOS 24 and 25, respectively)

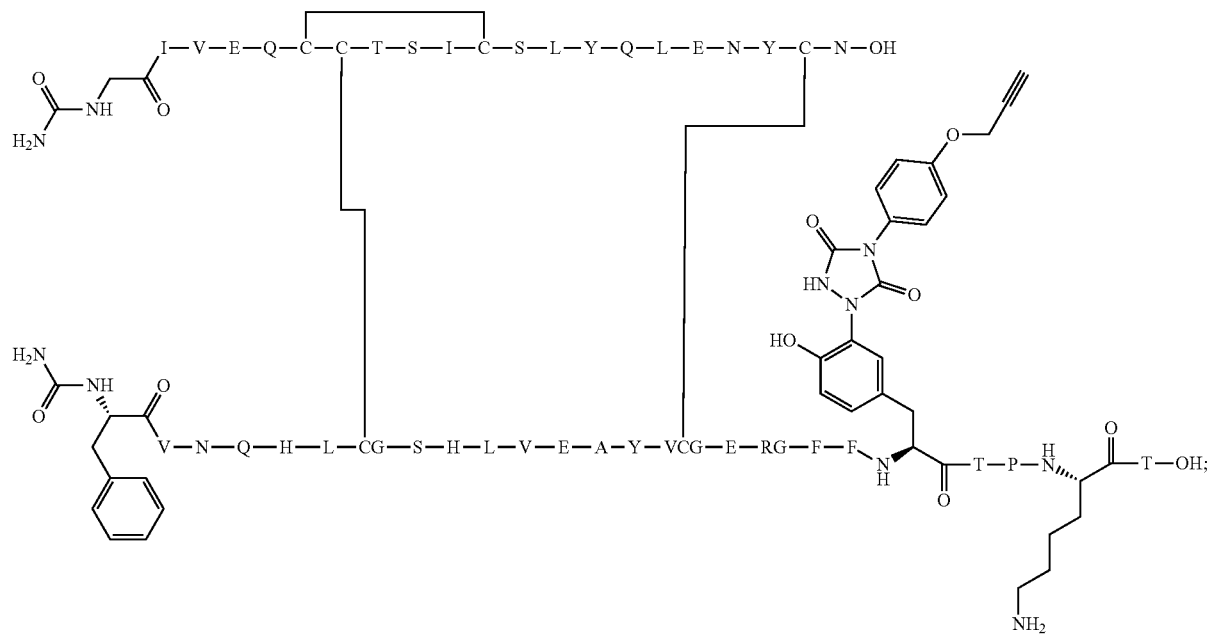
COMPOUND 6 (SEQ ID NOS 24 and 26, respectively)
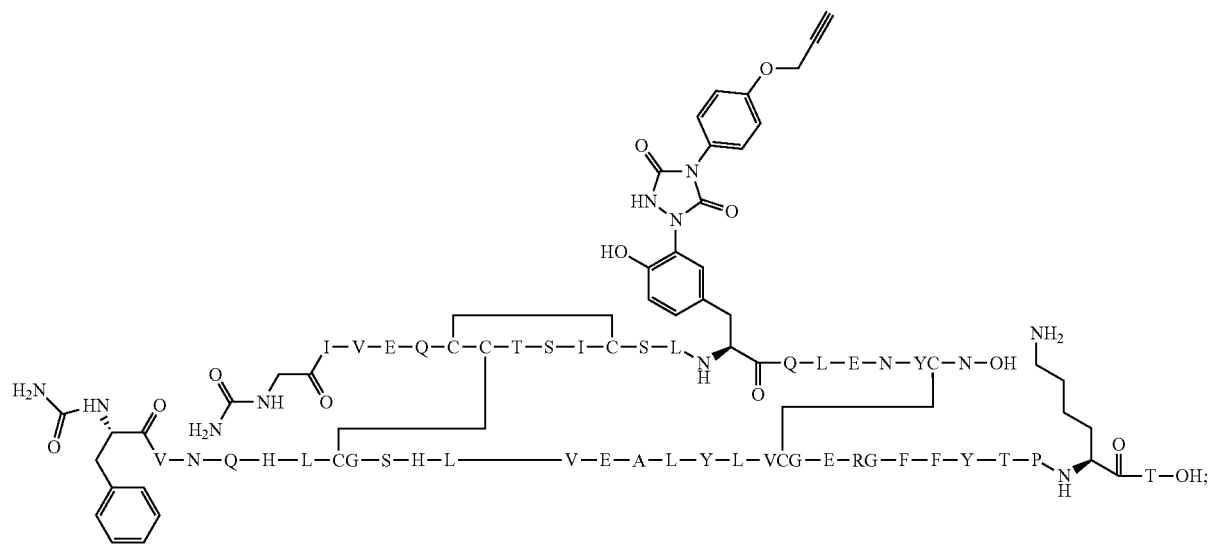
COMPOUND 7 (SEQ ID NOS 18 and 27, respectively)

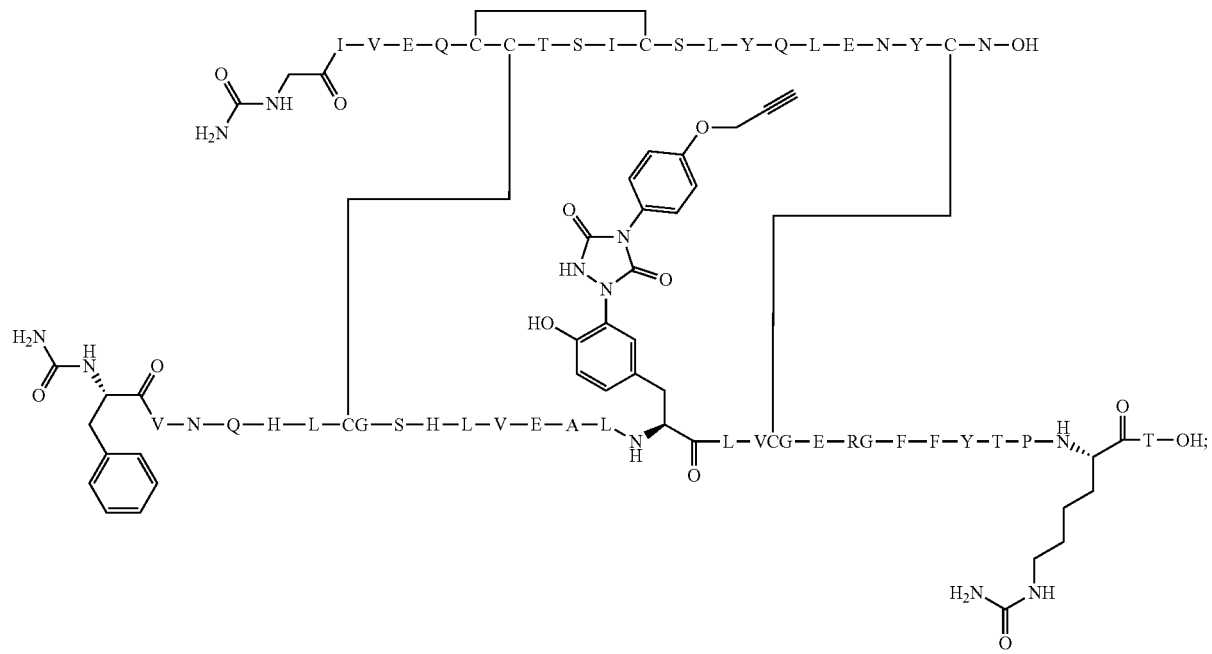
COMPOUND 8 (SEQ ID NOS 24 and 28, respectively)
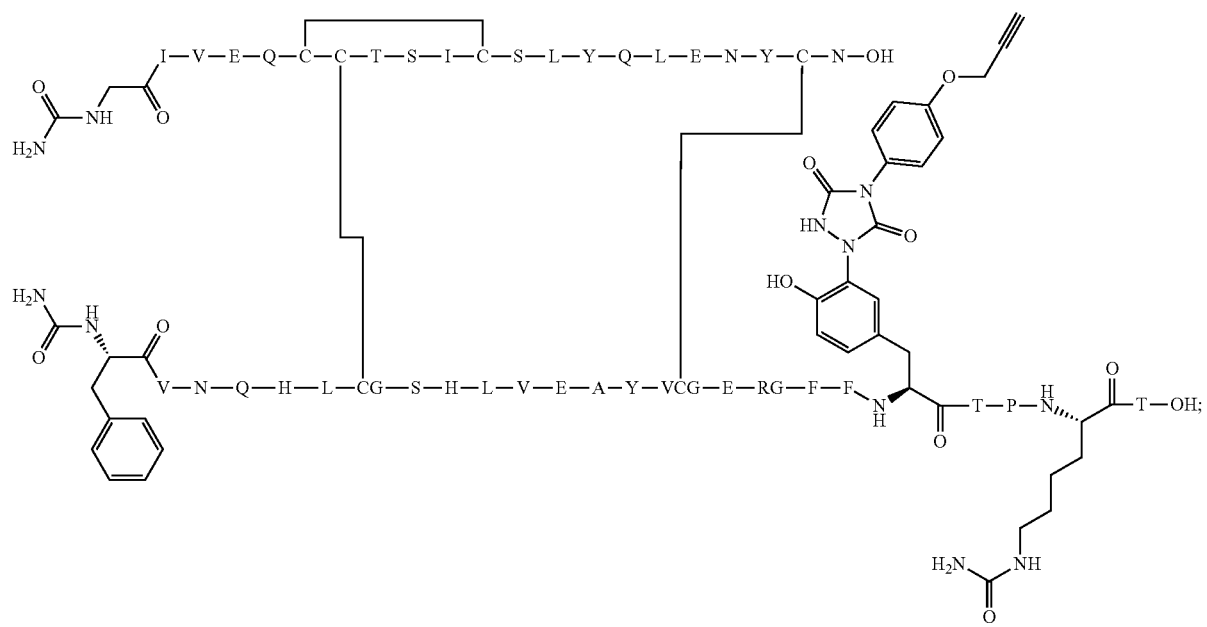
COMPOUND 9 (SEQ ID NOS 24 and 20, respectively)

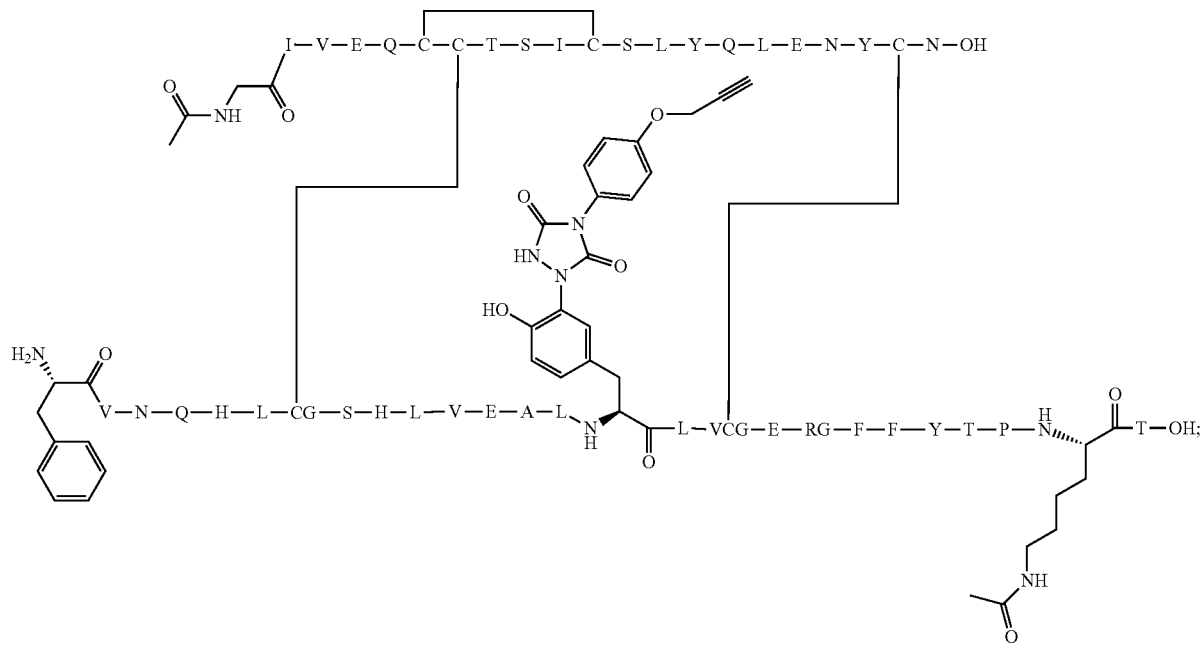
COMPOUND 10 (SEQ ID NOS 29 and 30, respectively)
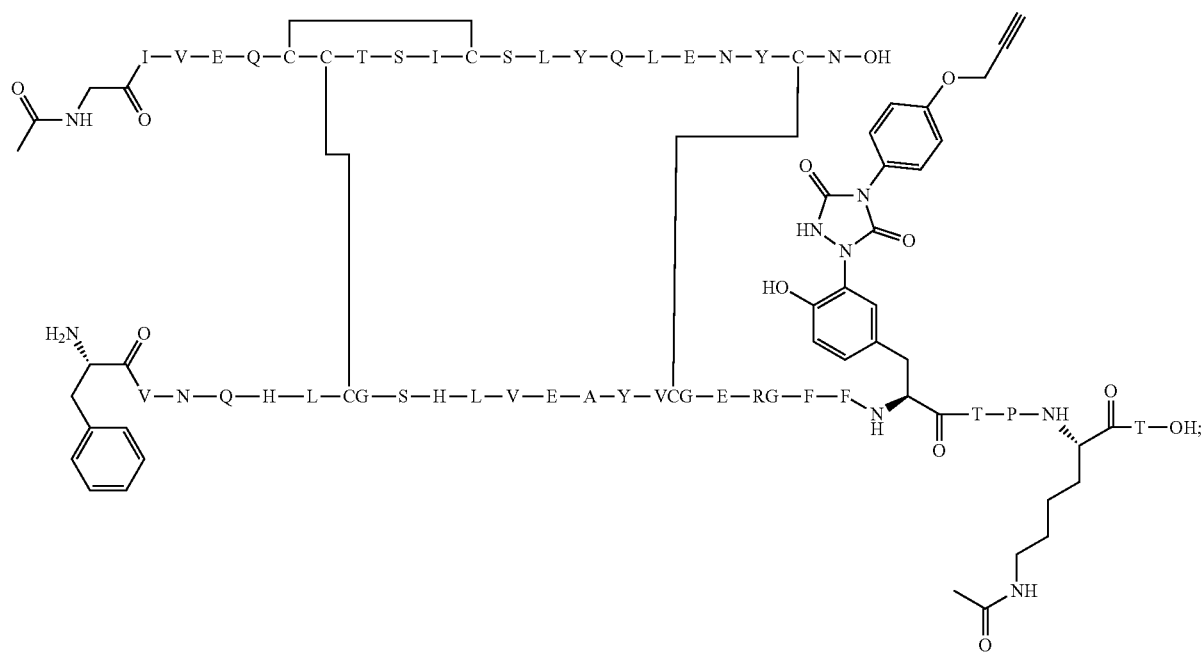
COMPOUND 11 (SEQ ID NOS 29 and 23, respectively)

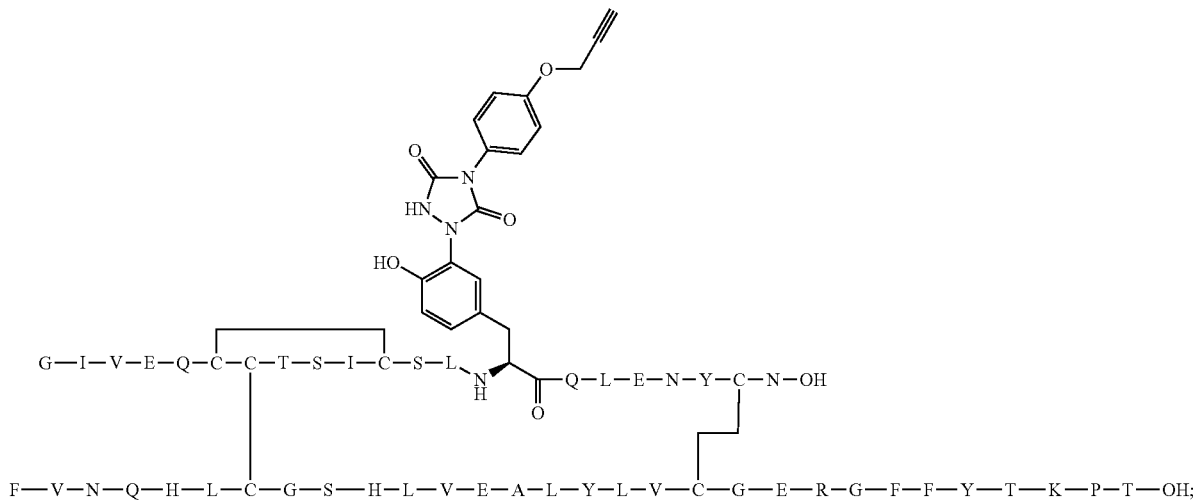
COMPOUND 12 (SEQ ID NOS 31 and 4, respectively)
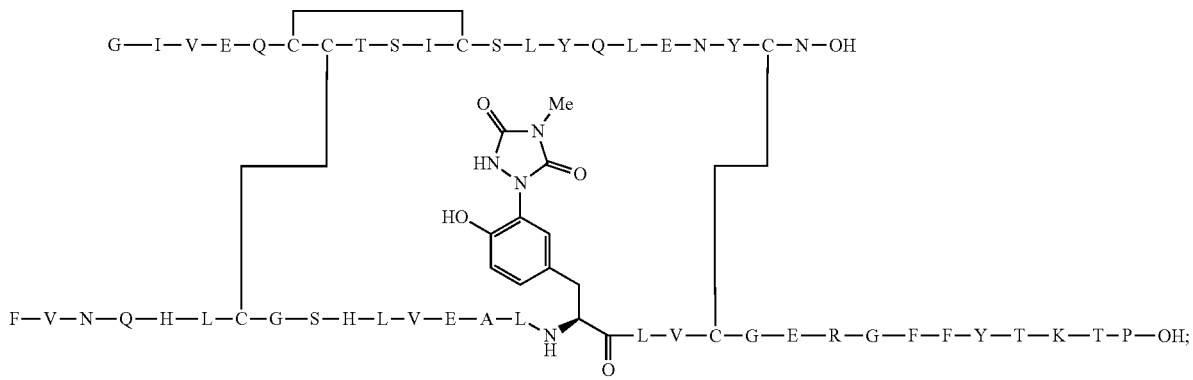
COMPOUND 13 (SEQ ID NOS 1 and 32, respectively)
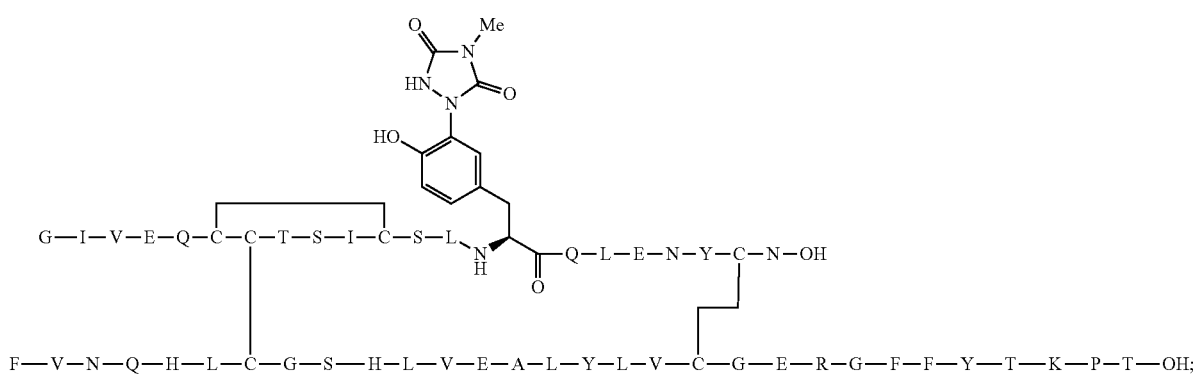
COMPOUND 14 (SEQ ID NOS 33 and 4, respectively)

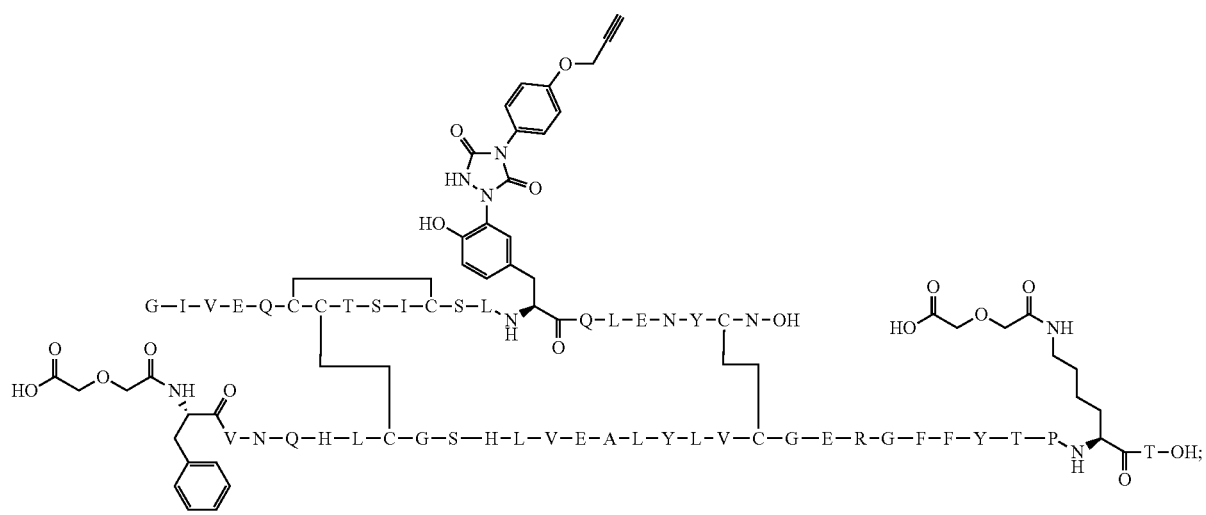
COMPOUND 15 (SEQ ID NOS 31 and 34, respectively)
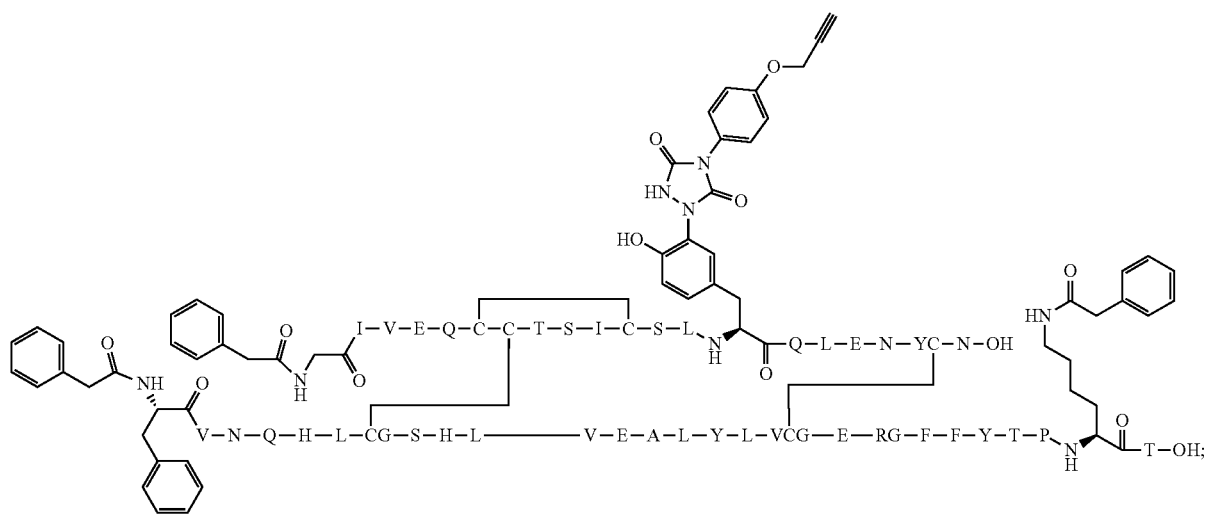
COMPOUND 16 (SEQ ID NOS 35 and 36, respectively)
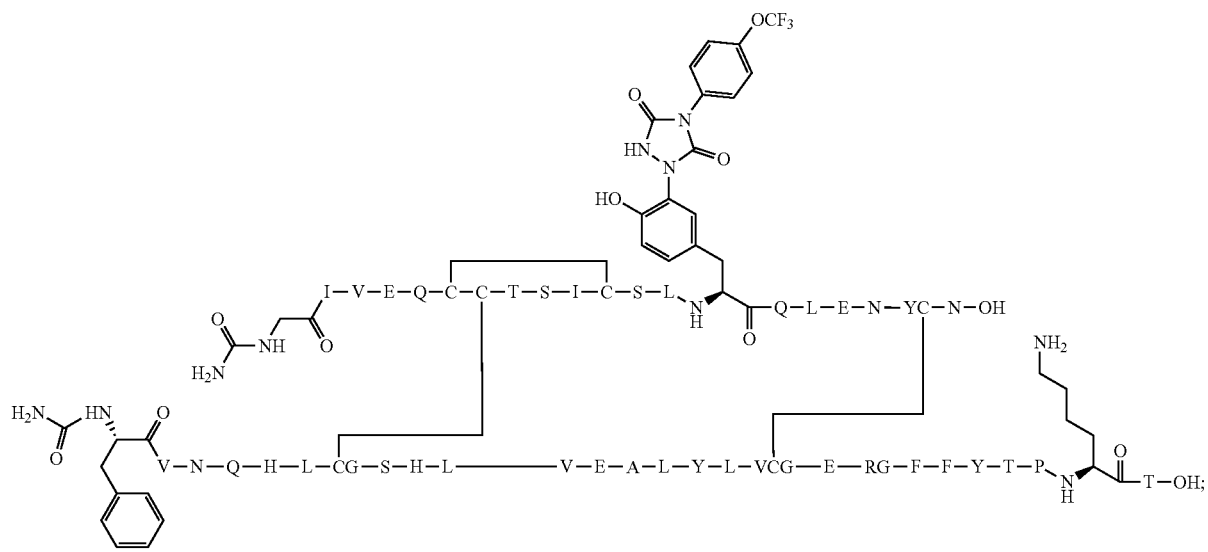
COMPOUND 17 (SEQ ID NOS 37 and 27, respectively)

-continued
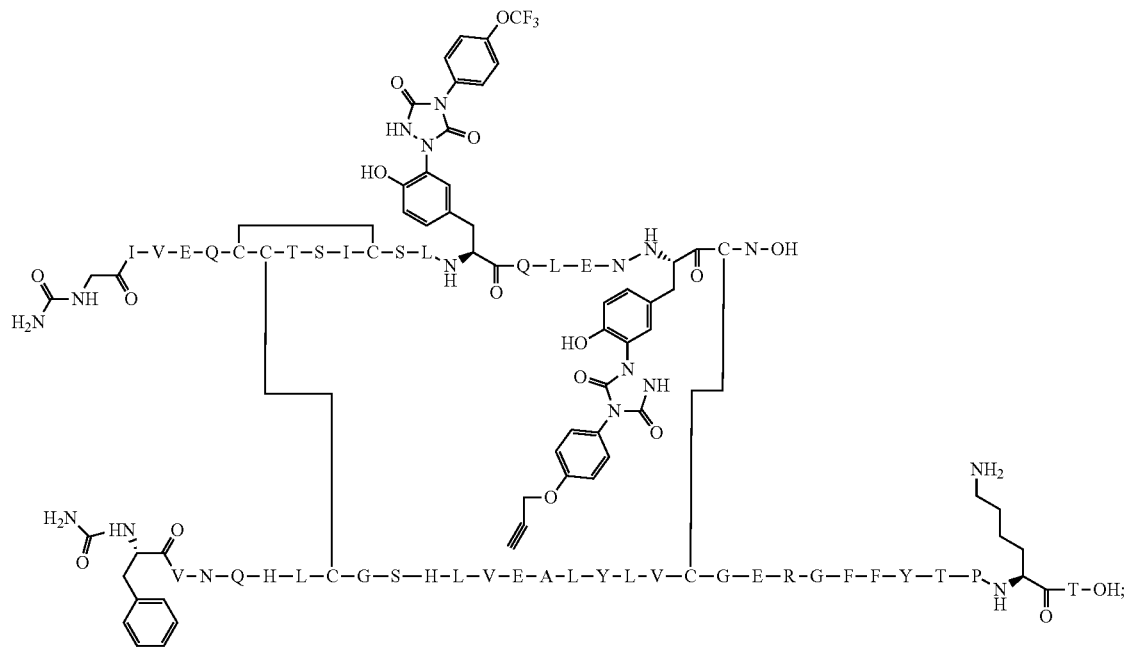
COMPOUND 18 (SEQ ID NOS 38 and 27, respectively)
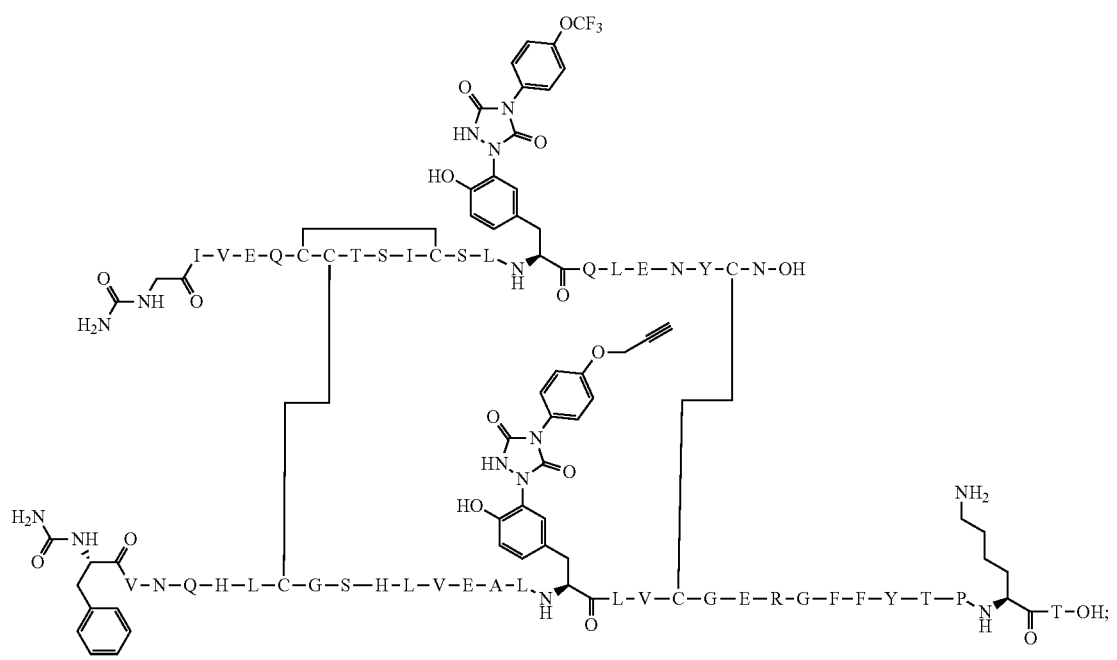
COMPOUND 19 (SEQ ID NOS 37 and 25, respectively)

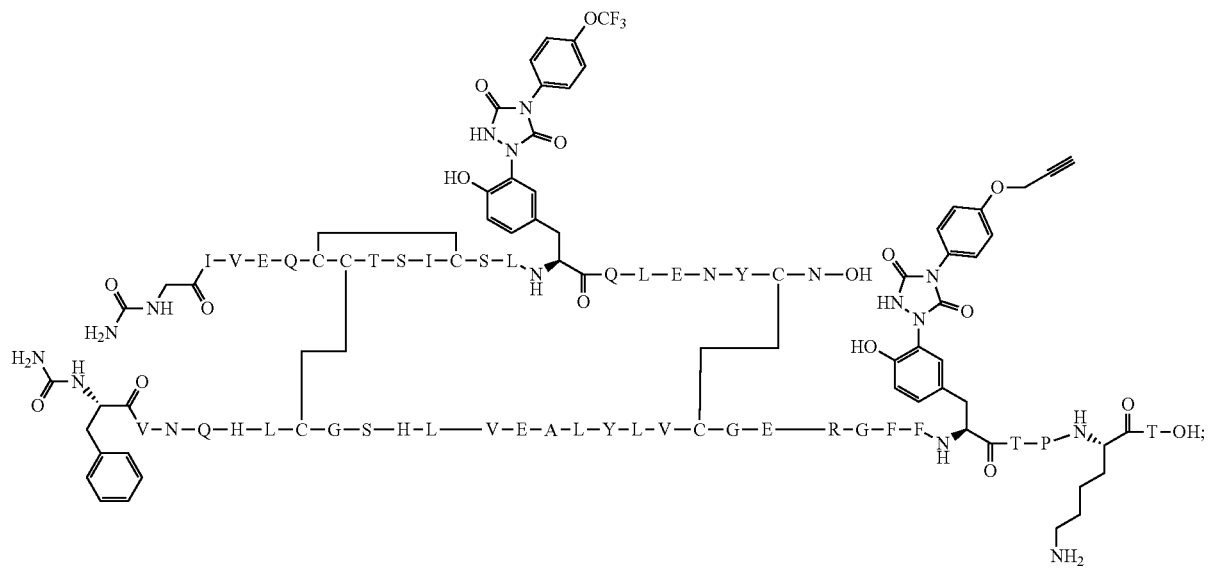
COMPOUND 20 (SEQ ID NOS 37 and 26, respectively)
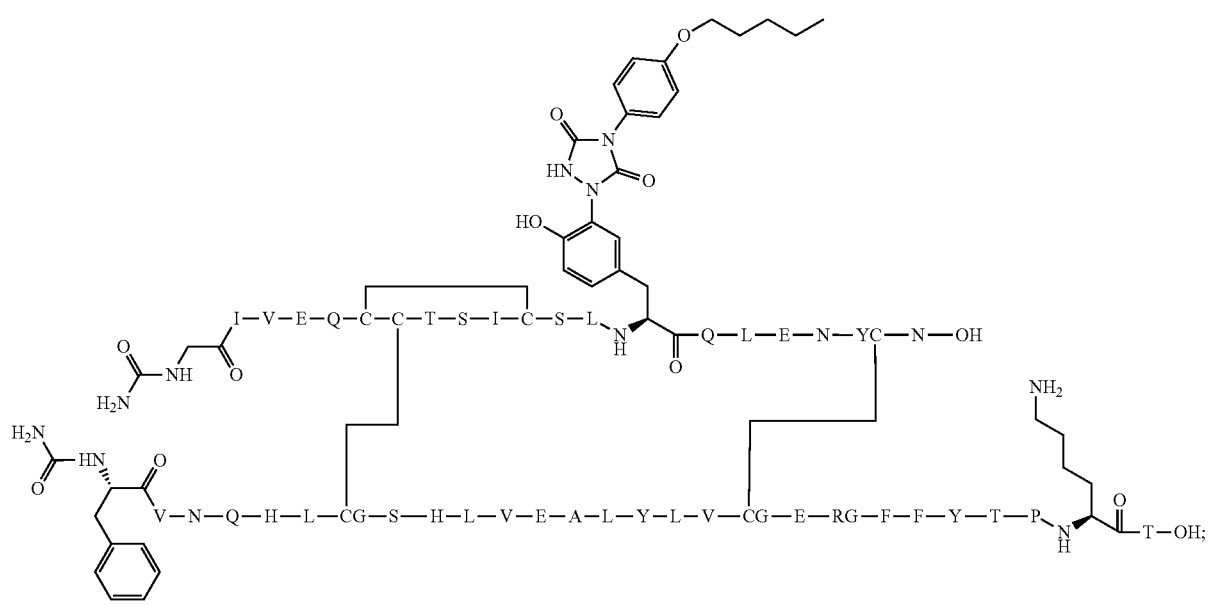
COMPOUND 21 (SEQ ID NOS 39 and 27, respectively)

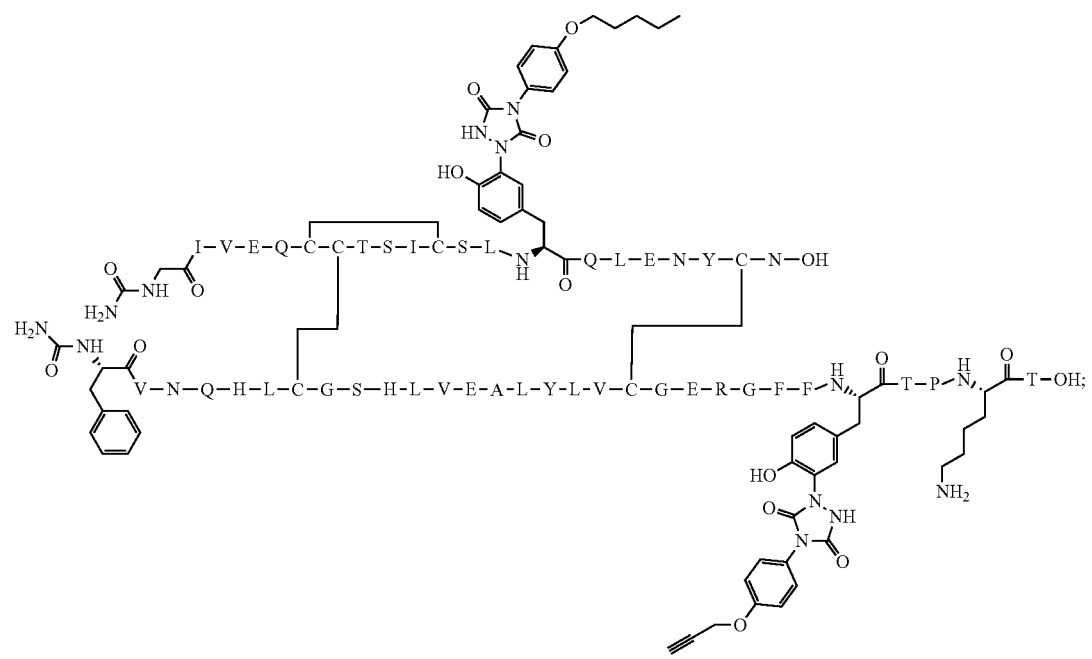
COMPOUND 22 (SEQ ID NOS 39 and 26, respectively)
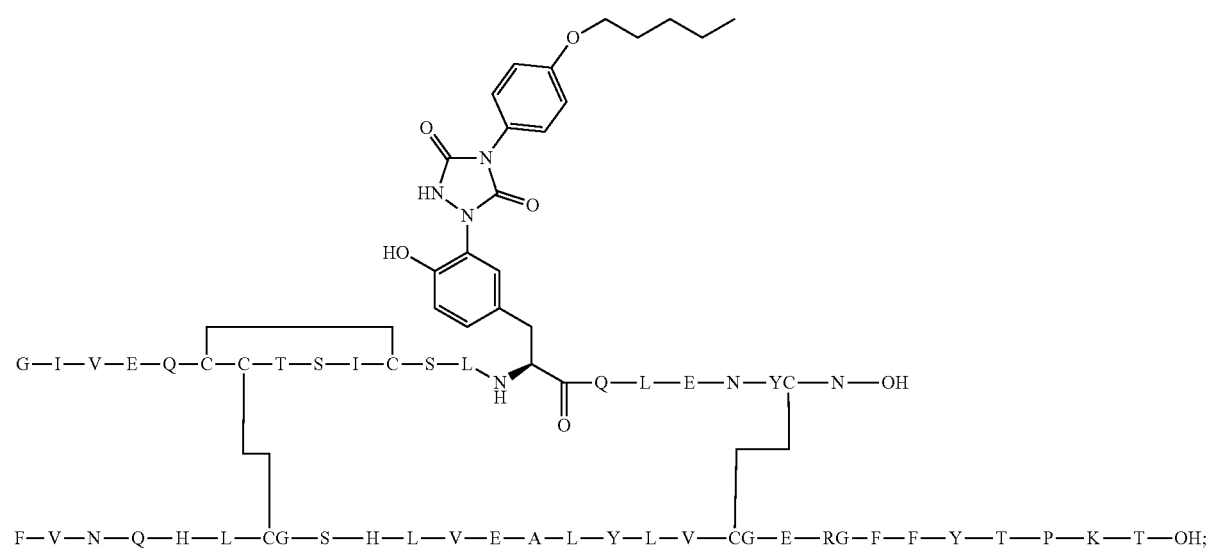
COMPOUND 23 (SEQ ID NOS 40 and 2, respectively)

-continued
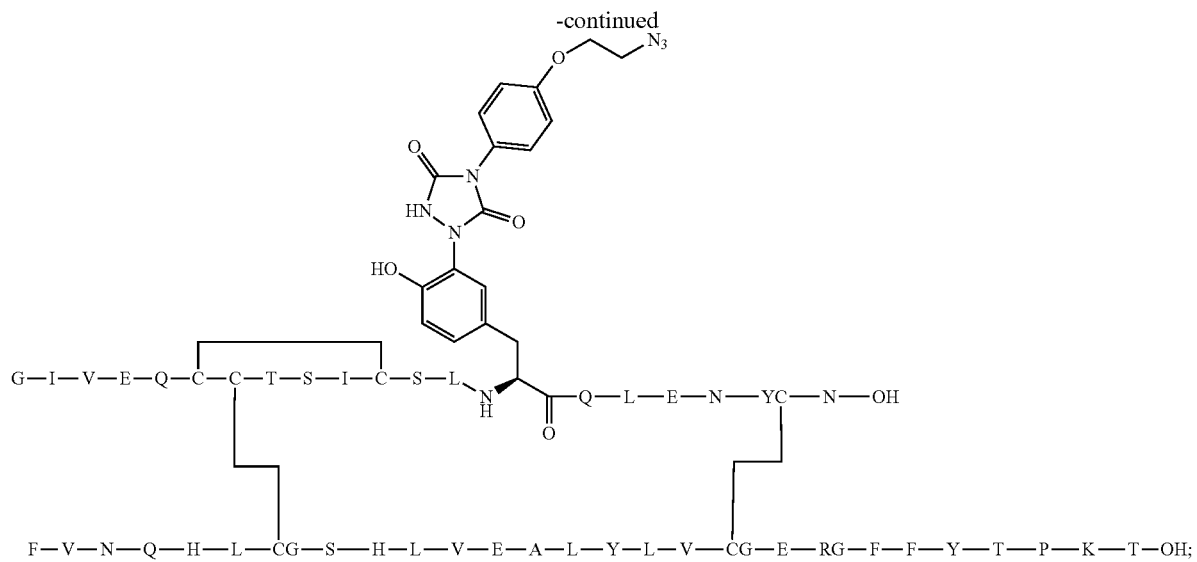
COMPOUND 24 (SEQ ID NOS 41 and 2, respectively)
and
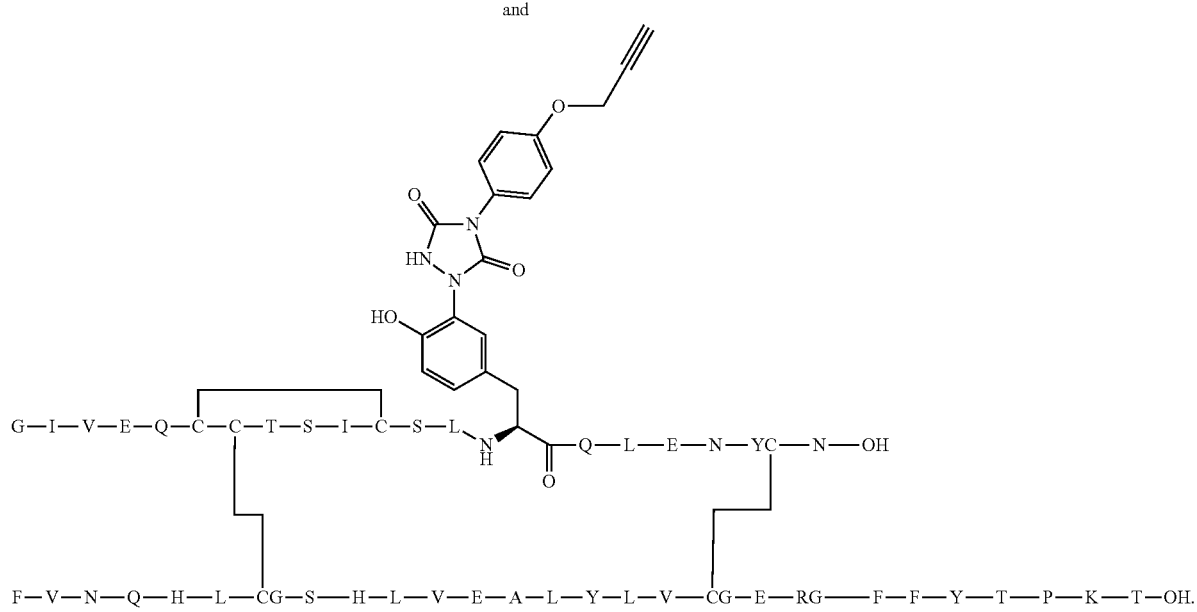
COMPOUND 25 (SEQ ID NOS 31 and 2, respectively)
* * * * *